(12) United States Patent
Chai et al.

(10) Patent No.: US 11,484,625 B2
(45) Date of Patent: Nov. 1, 2022

(54) STEM CELLS AND DEVICES FOR BONE REGENERATION

(71) Applicant: Alfred E. Mann Institute for Biomedical Engineering at the University of Southern California, Los Angeles, CA (US)

(72) Inventors: Yang Chai, Pasadena, CA (US); Yong Chen, La Canada, CA (US); Yuan Yuan, Los Angeles, CA (US); Yuxing Guo, Los Angeles, CA (US); Xiangjia Li, Los Angeles, CA (US); Zoe Johnson, Los Angeles, CA (US)

(73) Assignee: ALFRED E. MANN INSTITUTE FOR BIOMEDICAL ENGINEERING AT THE UNIVERSITY OF SOUTHERN CALIFORNIA, Los Angeles, CA (US)

( * ) Notice: Subject to any disclaimer, the term of this patent is extended or adjusted under 35 U.S.C. 154(b) by 93 days.

(21) Appl. No.: 16/762,398

(22) PCT Filed: Nov. 8, 2018

(86) PCT No.: PCT/US2018/059860
§ 371 (c)(1),
(2) Date: May 7, 2020

(87) PCT Pub. No.: WO2019/094617
PCT Pub. Date: May 16, 2019

(65) Prior Publication Data
US 2020/0276361 A1    Sep. 3, 2020

Related U.S. Application Data

(60) Provisional application No. 62/584,052, filed on Nov. 9, 2017.

(51) Int. Cl.
| | |
|---|---|
| A61L 27/38 | (2006.01) |
| A61L 27/46 | (2006.01) |
| A61L 27/54 | (2006.01) |
| A61L 27/56 | (2006.01) |
| A61F 2/28 | (2006.01) |
| C08L 67/04 | (2006.01) |

(52) U.S. Cl.
CPC ............ *A61L 27/3834* (2013.01); *A61F 2/28* (2013.01); *A61L 27/3847* (2013.01); *A61L 27/46* (2013.01); *A61L 27/54* (2013.01); *A61L 27/56* (2013.01); *A61F 2002/285* (2013.01); *A61F 2002/2817* (2013.01); *A61F 2002/2835* (2013.01); *A61L 2300/204* (2013.01); *A61L 2300/414* (2013.01); *A61L 2430/02* (2013.01); *C08L 67/04* (2013.01)

(58) Field of Classification Search
CPC .. A61L 27/3834; A61L 27/3847; A61L 27/46; A61L 27/54; A61L 27/56; A61L 2300/204; A61L 2300/414; A61L 2430/02; A61F 2/28; A61F 2002/2817; A61F 2002/2835; A61F 2002/285; C08L 67/04

See application file for complete search history.

(56) References Cited

U.S. PATENT DOCUMENTS

| | | | |
|---|---|---|---|
| 8,916,228 B2 | 12/2014 | Oh et al. | |
| 2009/0269387 A1 | 10/2009 | Zubery et al. | |
| 2012/0219535 A1 | 8/2012 | Maxson, Jr. et al. | |
| 2012/0271418 A1 | 10/2012 | Hollister et al. | |
| 2013/0236513 A1* | 9/2013 | Guelcher | |
| 2014/0178455 A1 | 6/2014 | Nukavarapu et al. | |
| 2015/0283182 A1* | 10/2015 | Guelcher | |
| 2016/0135955 A1 | 5/2016 | Henderson et al. | |
| 2016/0184190 A1 | 6/2016 | Young | |

FOREIGN PATENT DOCUMENTS

| | | |
|---|---|---|
| CN | 1403165 A | 3/2003 |
| CN | 1503683 A | 6/2004 |
| CN | 101084026 A | 12/2007 |
| CN | 102596270 A | 6/2012 |

(Continued)

OTHER PUBLICATIONS

Invitation to Pay Additional Fees dated Feb. 4, 2019 in International Application No. PCT/US2018/059860 (2 pages).
International Search Report and Written Opinion dated Apr. 3, 2019 in International Application No. PCT/US2018/059860 (15 pages).

(Continued)

*Primary Examiner* — Alma Pipic
(74) *Attorney, Agent, or Firm* — McDermott Will & Emery LLP

(57) ABSTRACT

This invention relates to a bone regeneration product comprising at least one stem cell, at least one scaffold, and at least one stem cell. The stem cells suitable for this invention may comprise stem cells suitable for a dense bone regeneration, stem cells suitable for a spongy bone regeneration, or a combination thereof. The bone regeneration product may further comprise a growth factor. This invention also relates to a bone regeneration method and treatment of any bone that has a critical size defect. This invention also relates to a scaffold. This invention further relates to a 3D printed scaffold comprising hydroxyapatite (HA) and tricalcium phosphate (TCP). This invention also relates to a scaffold comprising a polymer. The polymer of this invention may be prepared by using photocurable polymers and/or monomers. The scaffold of this invention may comprise a growth factor and a small molecule. The small molecule N may be a Smurf1 inhibitor.

21 Claims, 76 Drawing Sheets

(56) References Cited

FOREIGN PATENT DOCUMENTS

| CN | 102716515 A | 10/2012 |
|----|-------------|---------|
| CN | 103300946 A | 9/2013 |
| CN | 105770996 A | 7/2016 |
| CN | 106563160 A | 4/2017 |
| CN | 106880869 A | 6/2017 |
| WO | 2006124062 A1 | 11/2006 |

OTHER PUBLICATIONS

European Patent Office—Extended European Search Report dated Aug. 26, 2021 for corresponding European Appln. No 18875376.8, 10 pgs.

Ma, Jingling, et al., "Concise Review: Cell-Based Strategies in Bone Tissue Engineering and Regenerative Medicine," Stem Cells Translational Medicine (2014) 3:98-107, AlphaMed Press; 10 pgs.

CNIPA—Office Action dated Oct. 13, 2021 for corresponding Chinese Appln. No. 201880083414.1, Translations in both Chinese and English, 16 pgs.

\* cited by examiner (A)
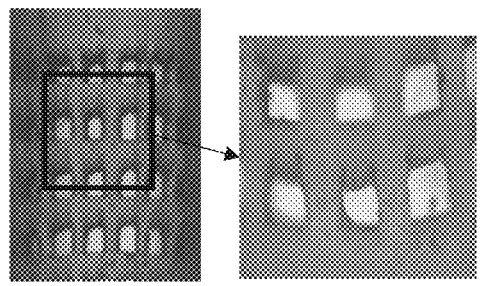
(B)
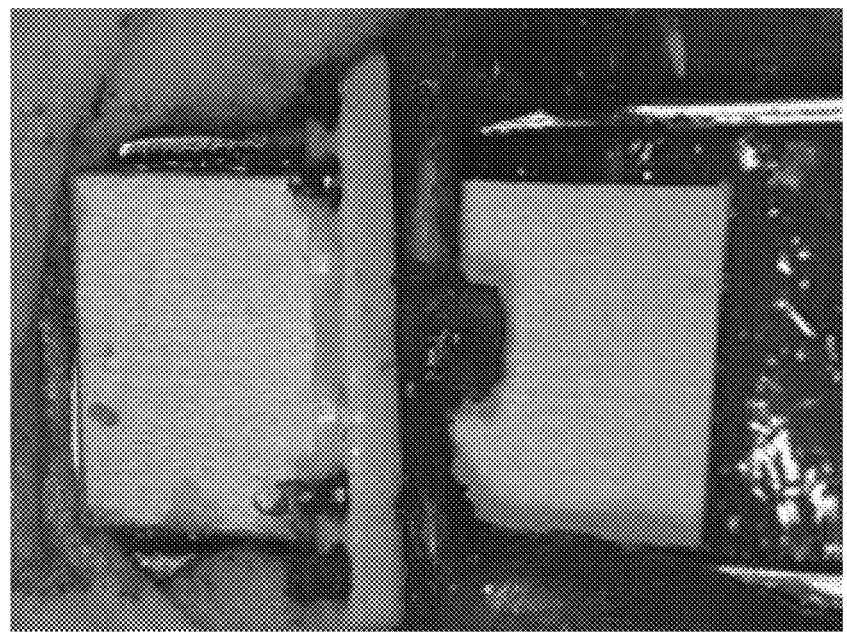
FIGS. 3 (A-B)

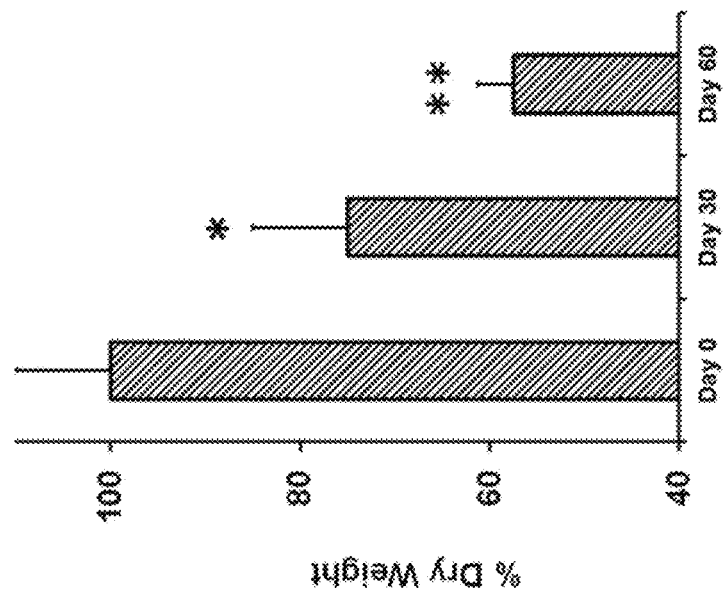
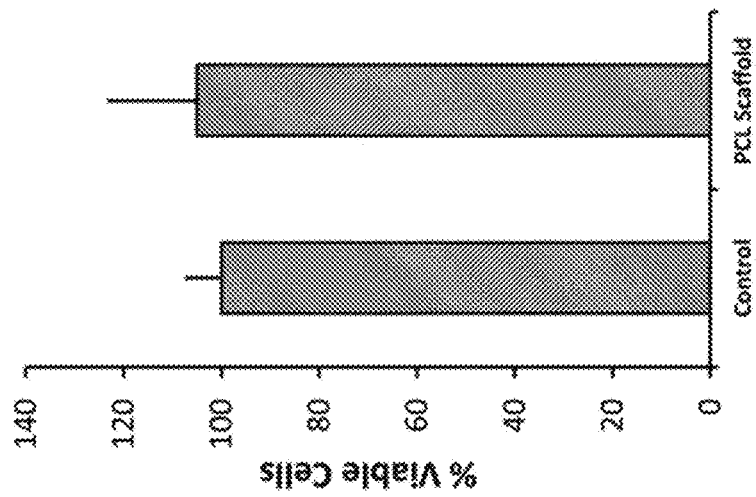
FIGS. 3 (C-D)

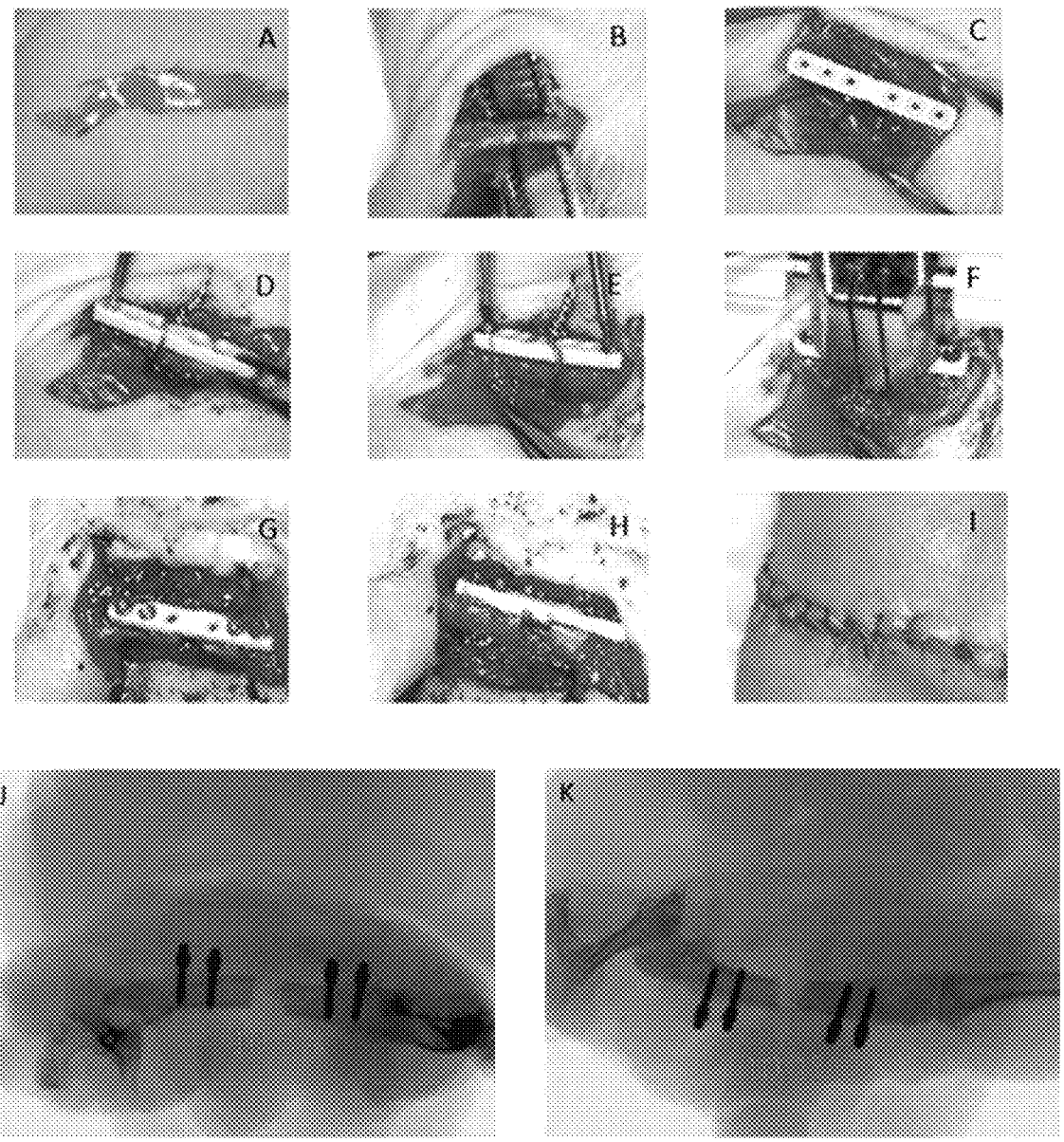
FIGS. 4 (A-K)

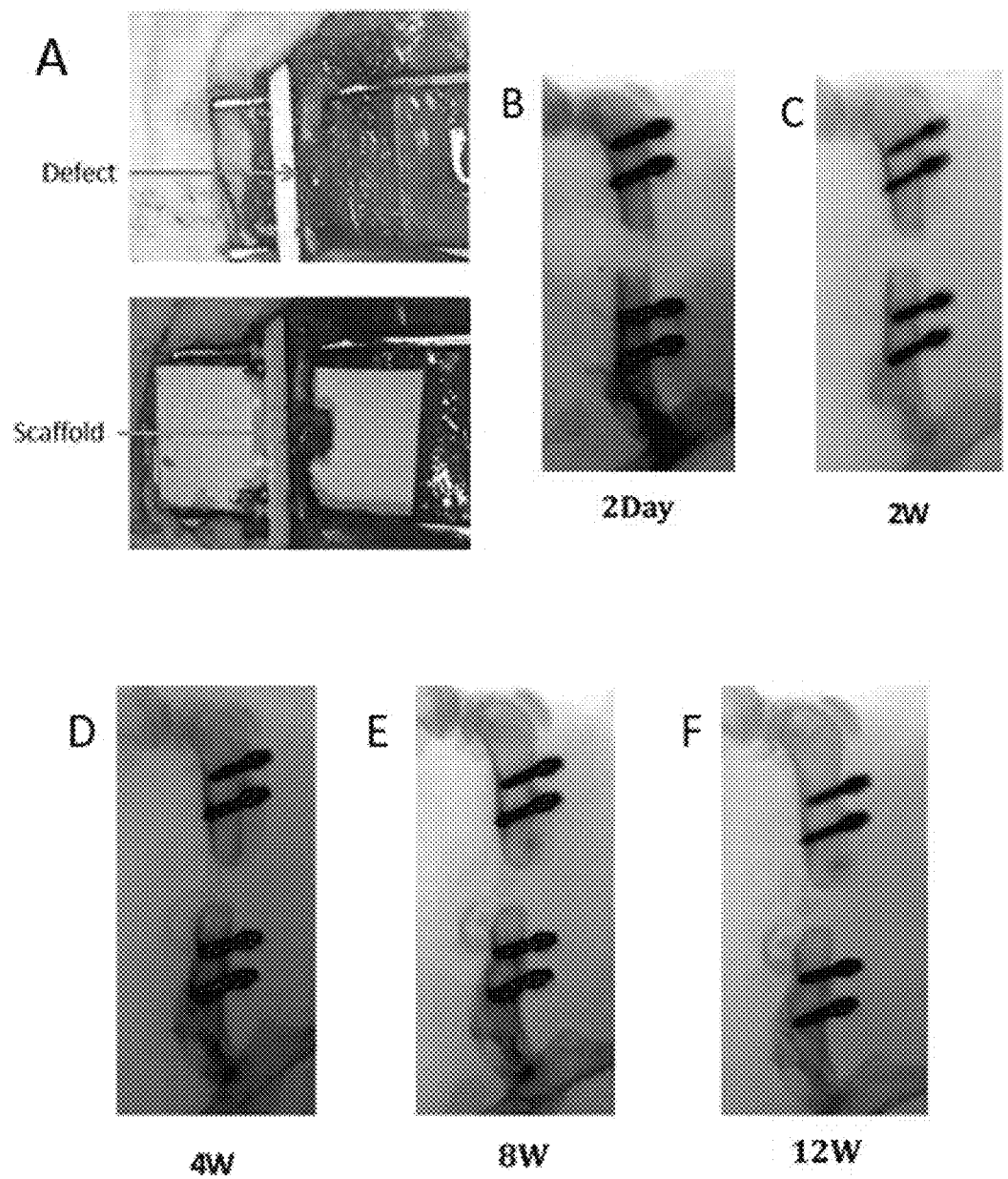
FIGS. 5 (A-F)

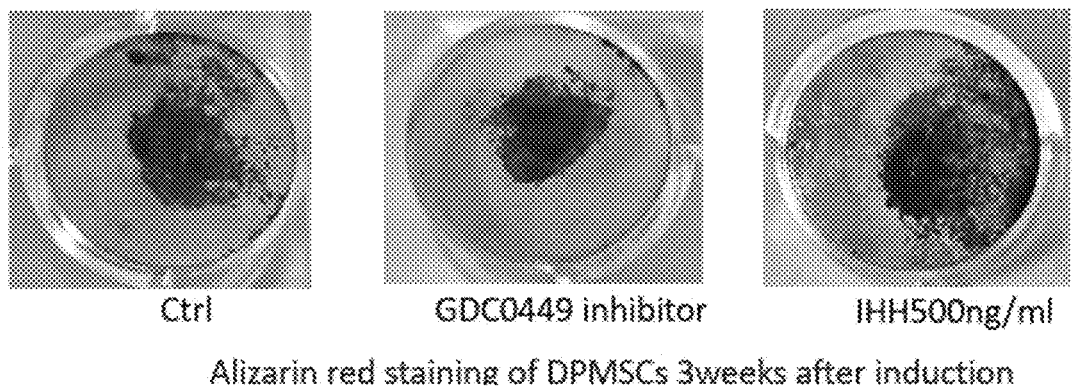
Alizarin red staining of DPMSCs 3weeks after induction
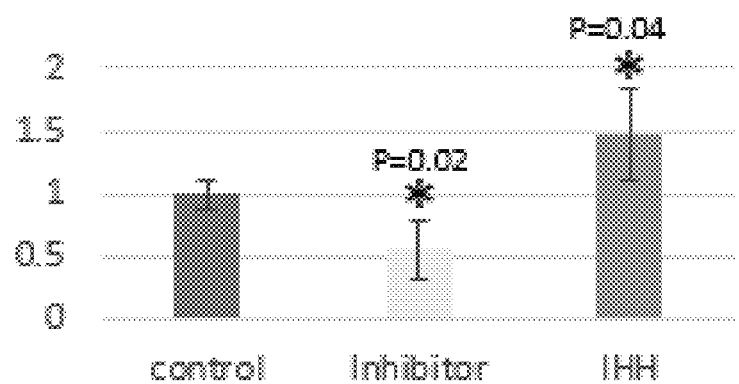
N=4
FIG. 6

FIGS. 8 (A-F)

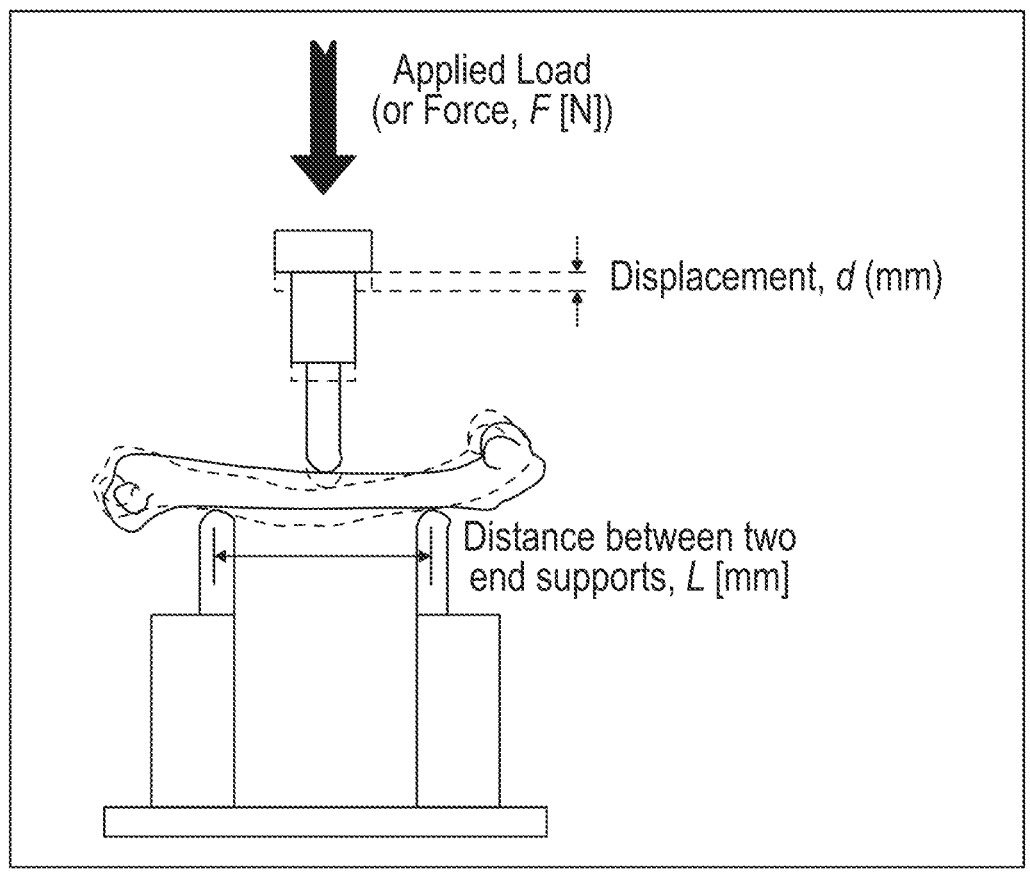
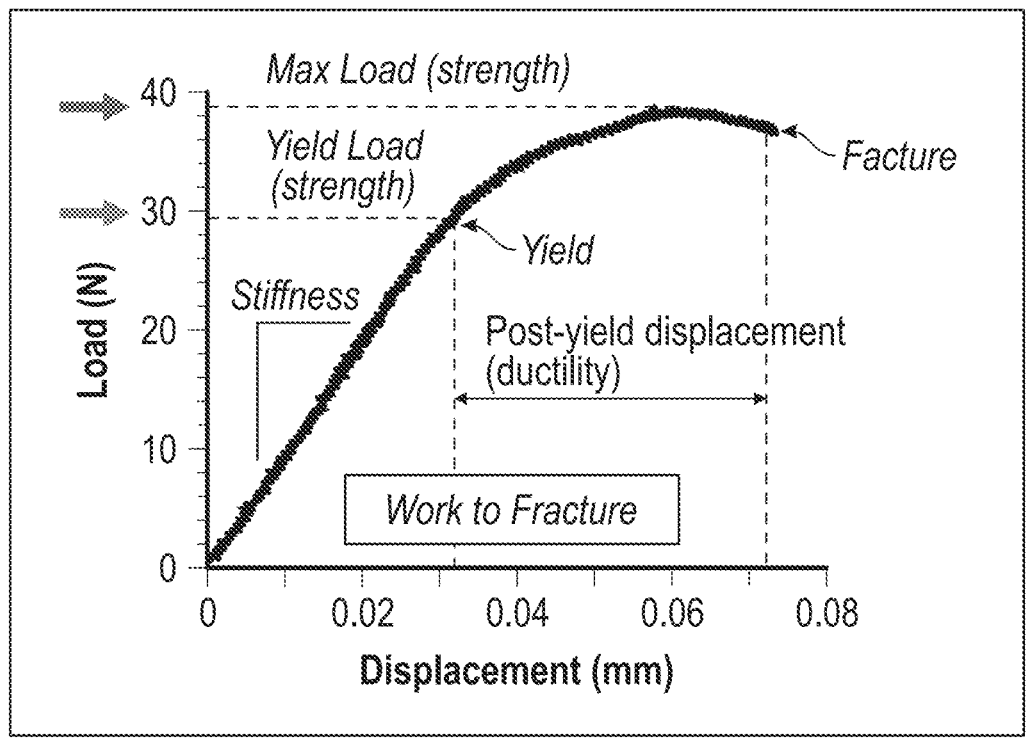
FIG. 12

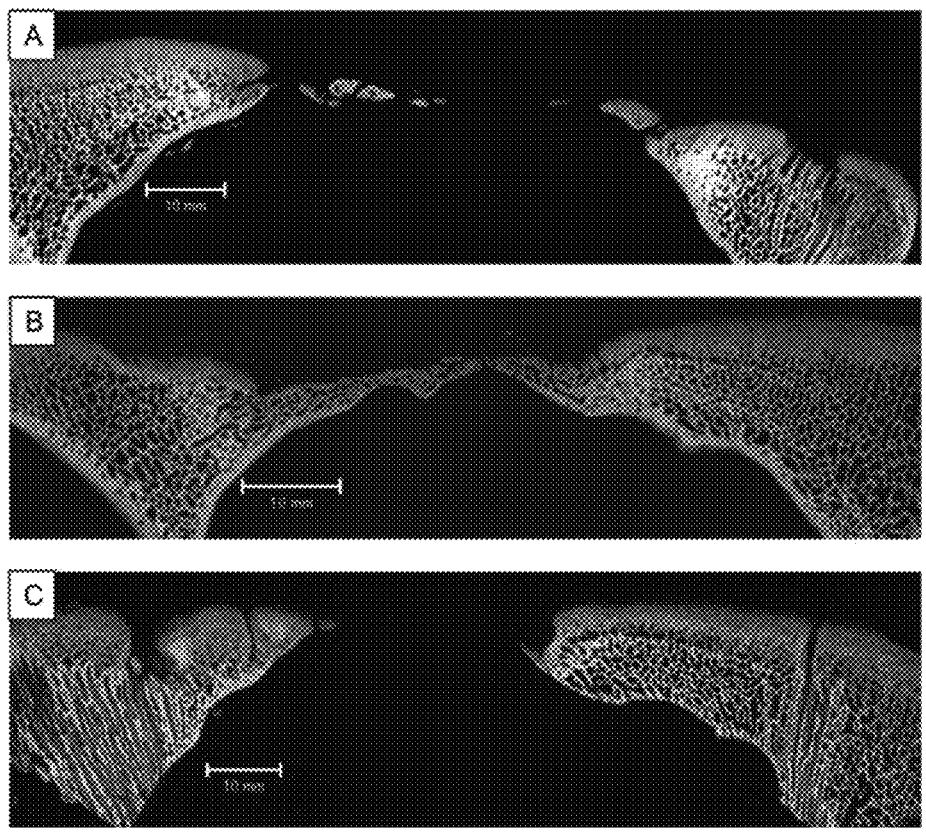
FIGS. 13 (A-C)

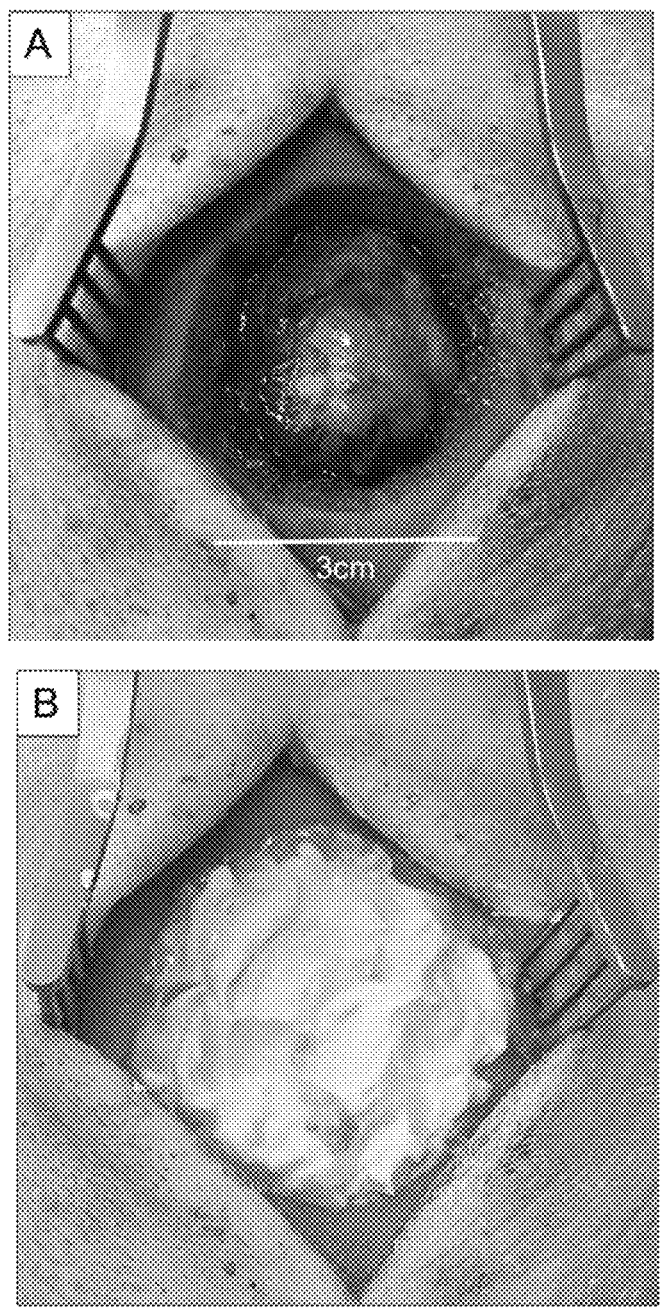
FIGS. 14 (A-B)

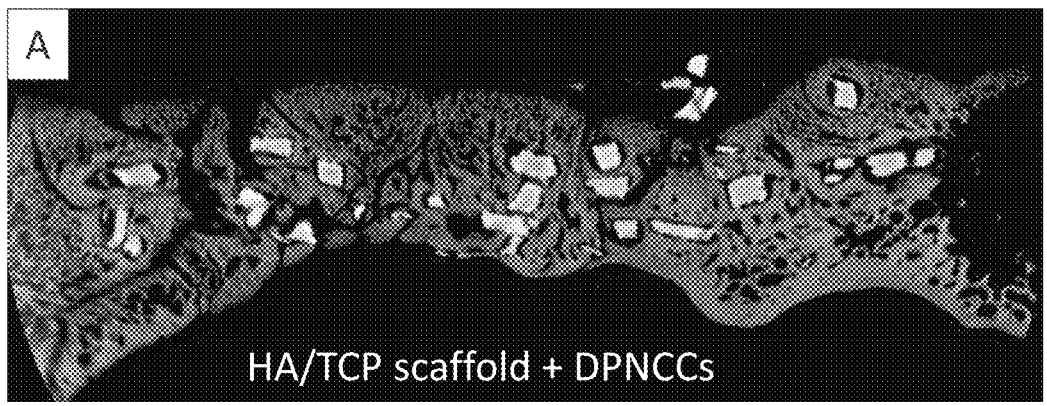
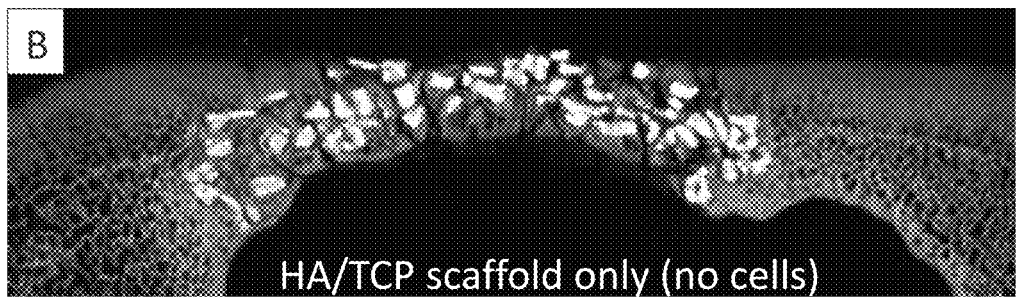
FIGS. 15 (A-B)

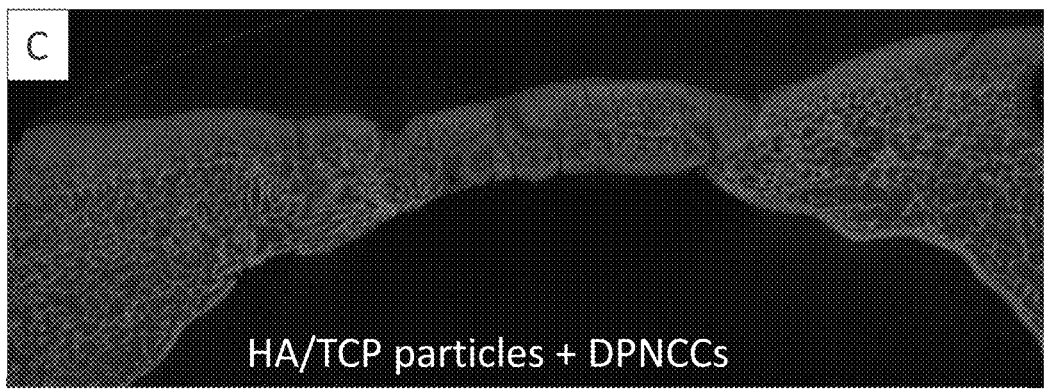
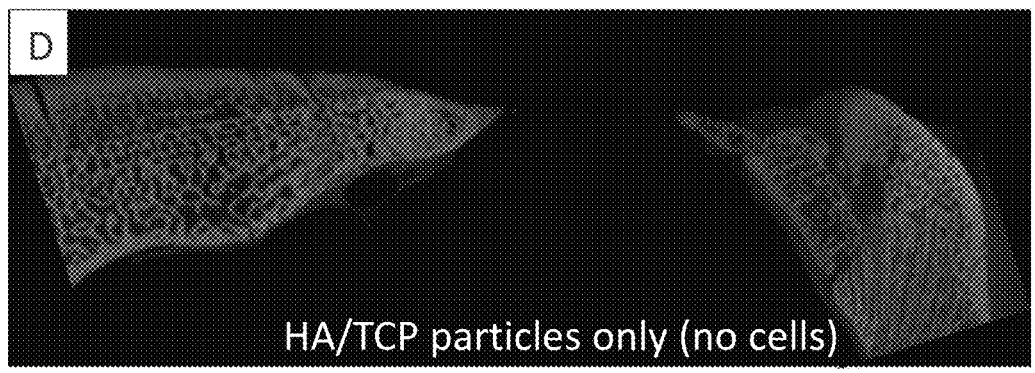
FIGS. 15 (C-D)

a     Mesh structure
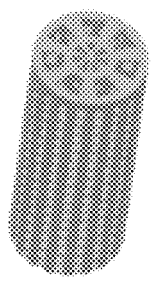
Bone Marrow Scaffold
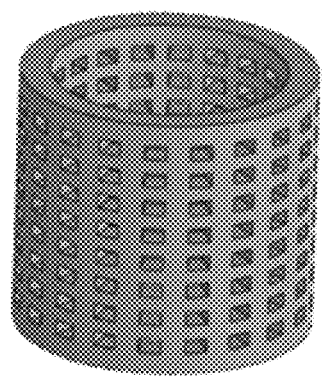
Cortical Bone Scaffold
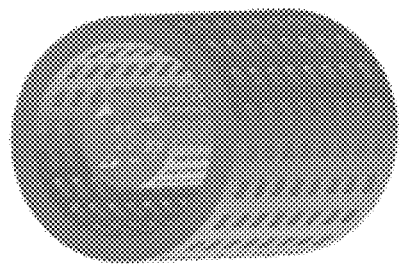
FIG. 21 (A)

b      Mcirolattice Structure
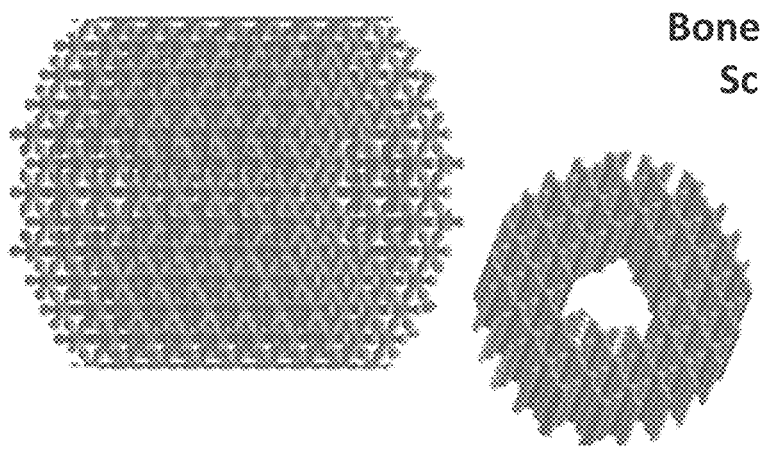
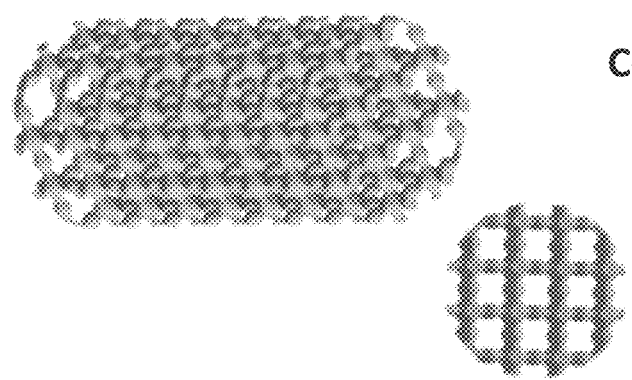
FIG. 21 (B)

C
Biomimetic Bone Structure
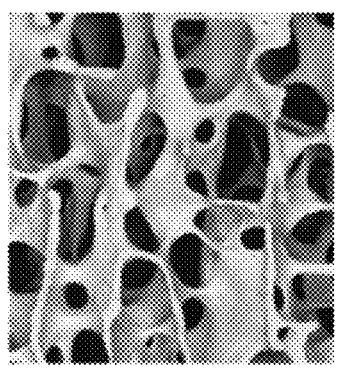
Bone Structure
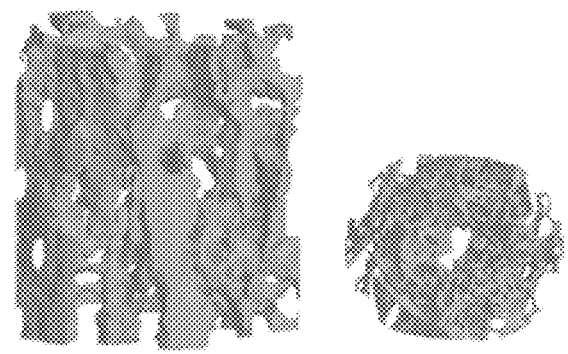
Cortical Bone Scaffold
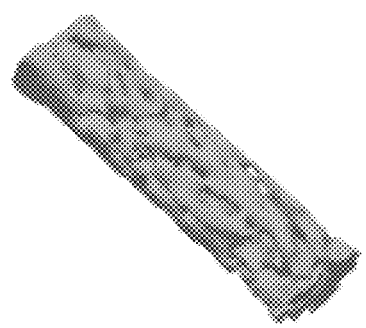
Bone Marrow Scaffold
FIG. 21 (C)

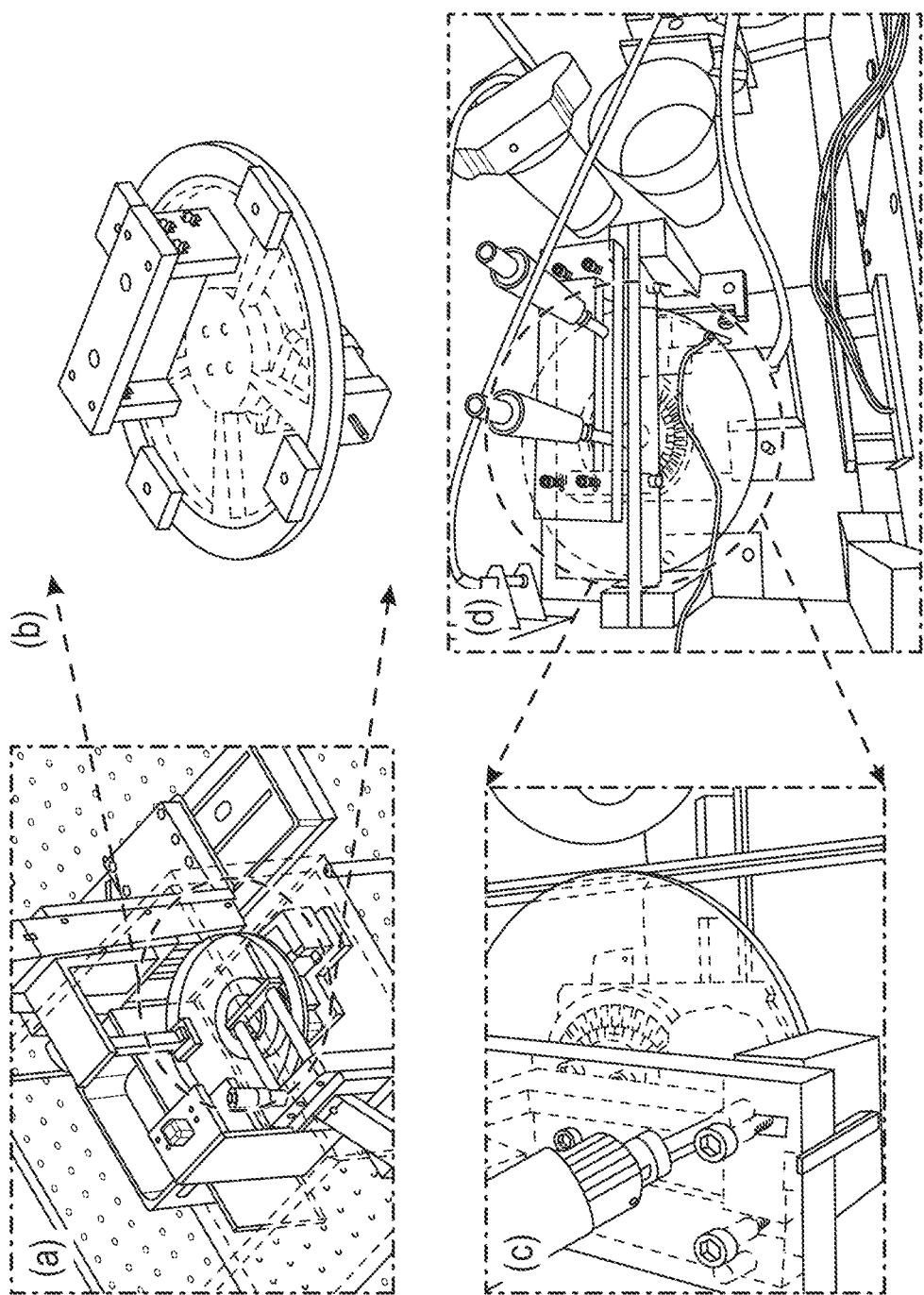
FIGS. 23 (A-D)

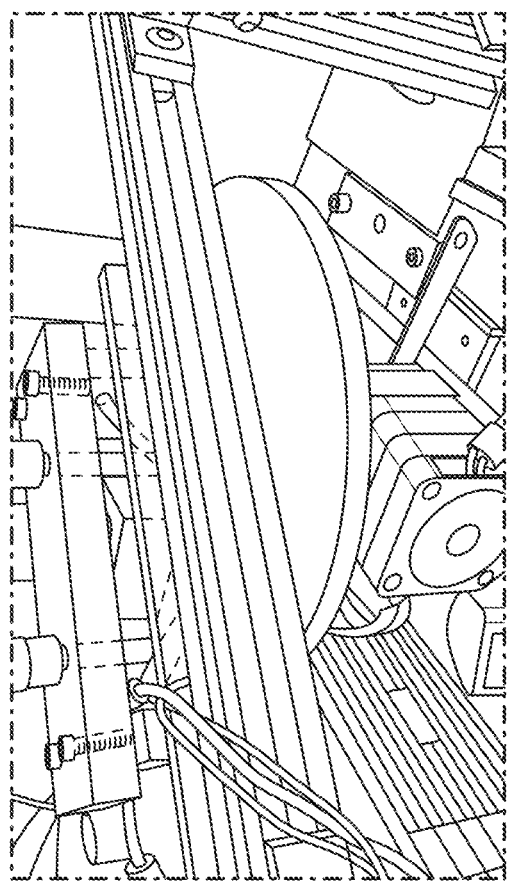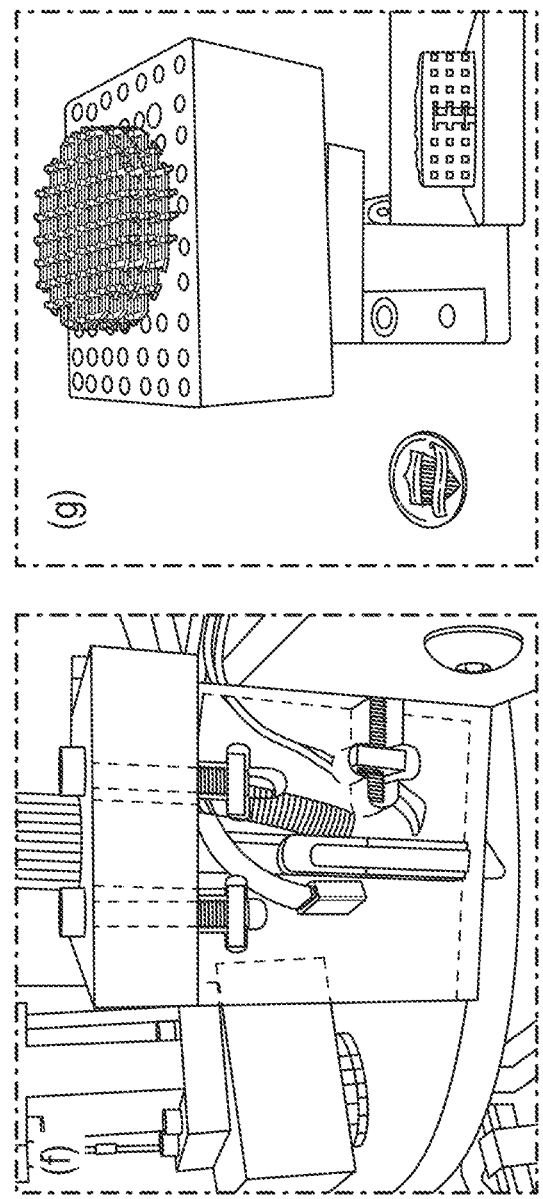
FIGS. 23 (E-G)

FIGS. 26 (A - B)

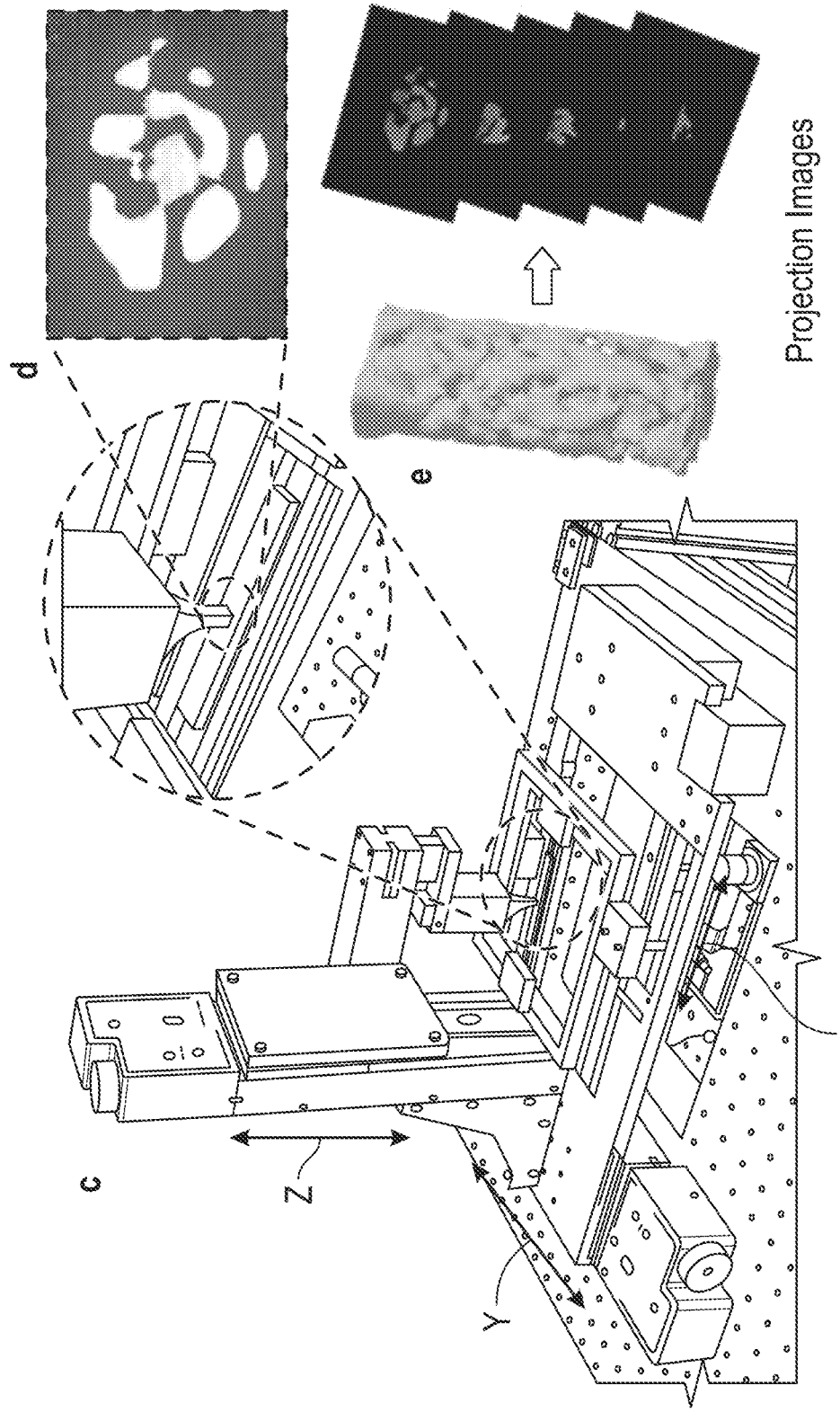
FIGS. 36 (C-E)

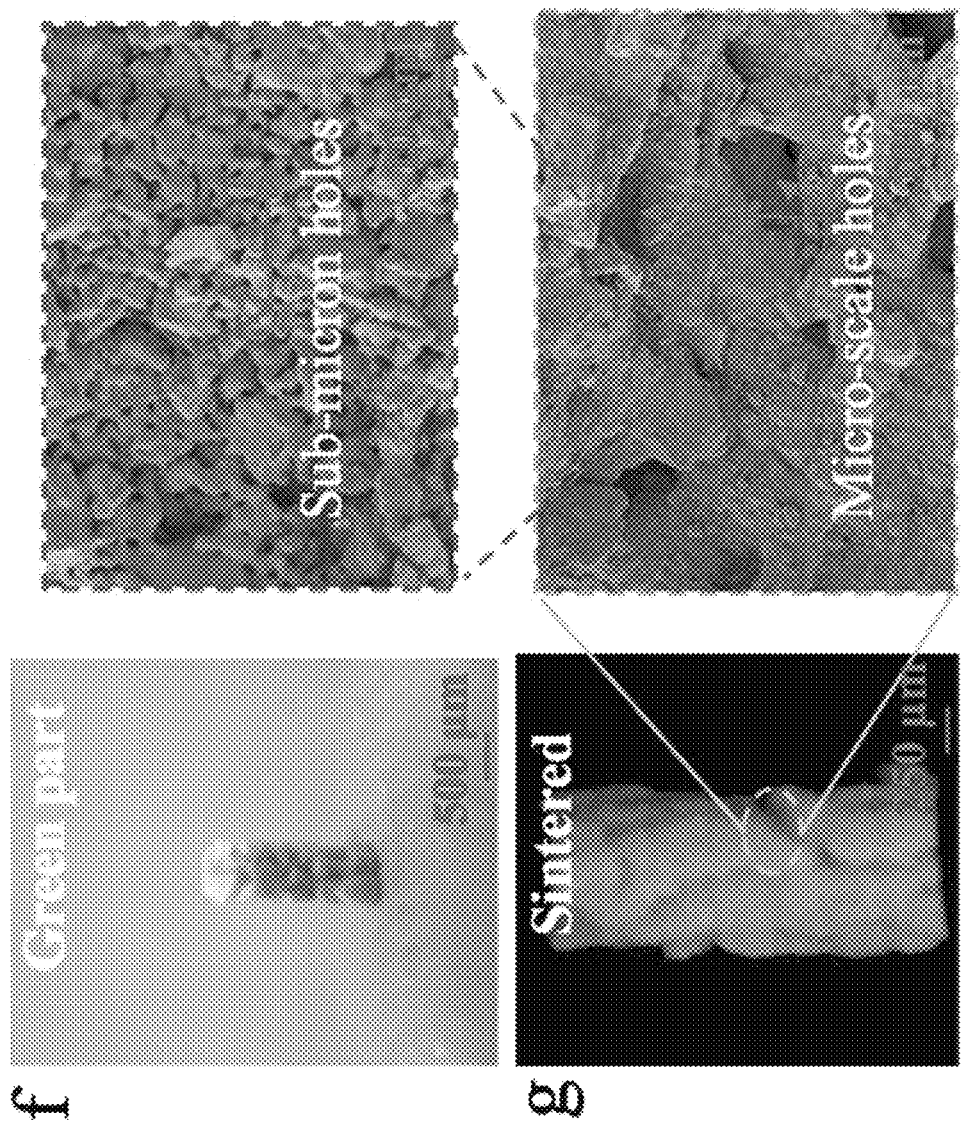
FIGS. 36 (F-G)

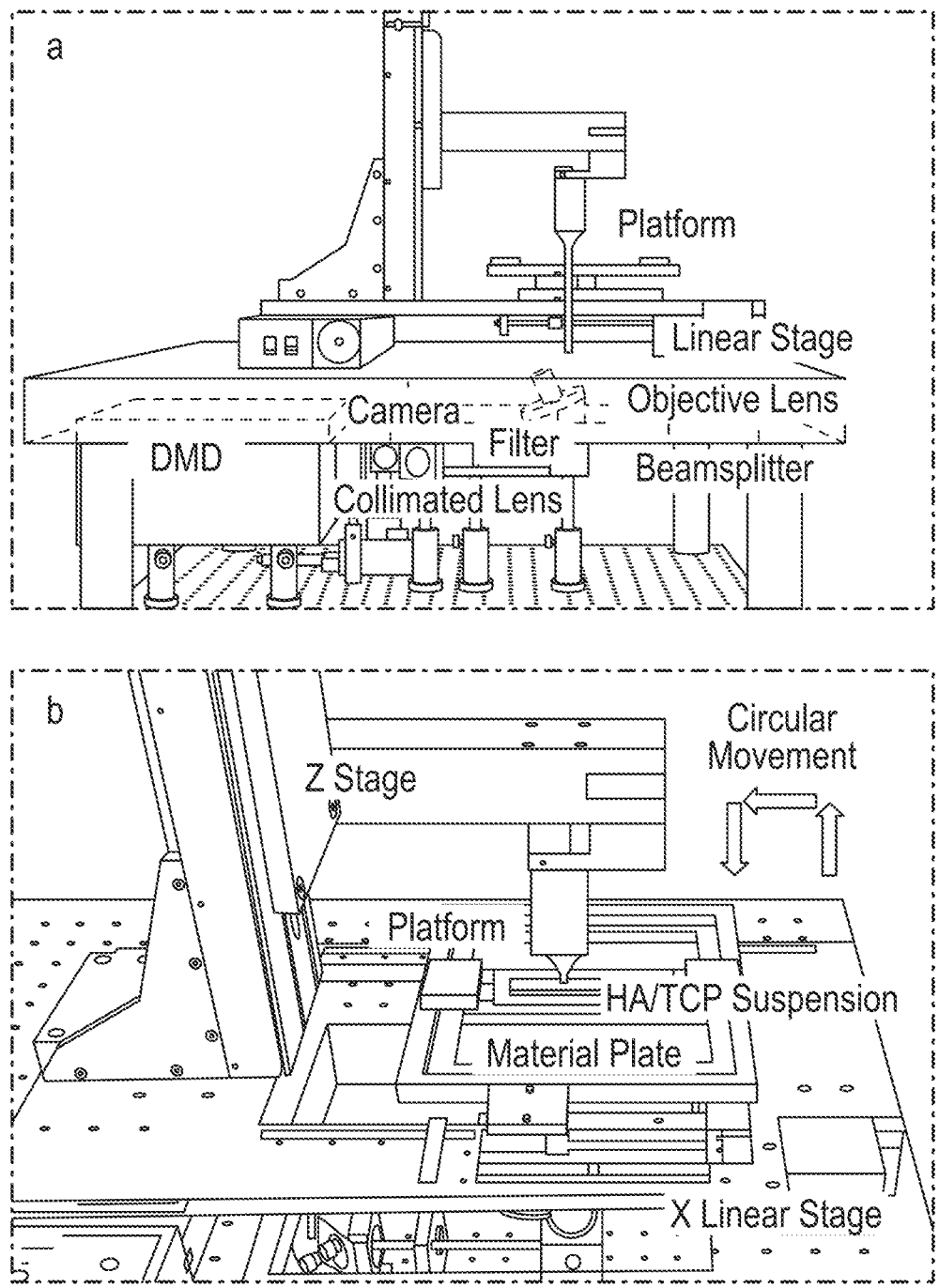
FIGS. 38 (A-B)

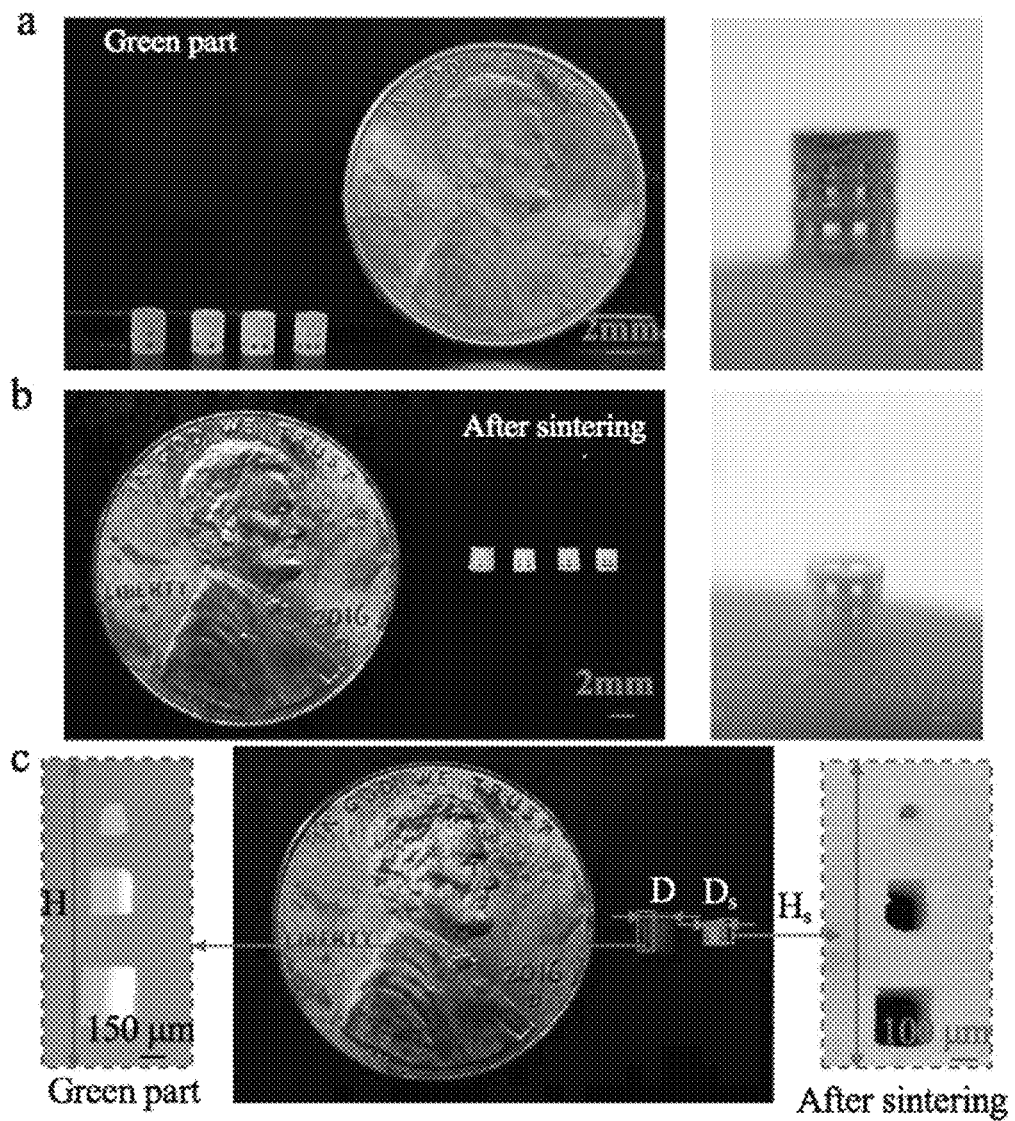
FIGS. 40 (A-C)

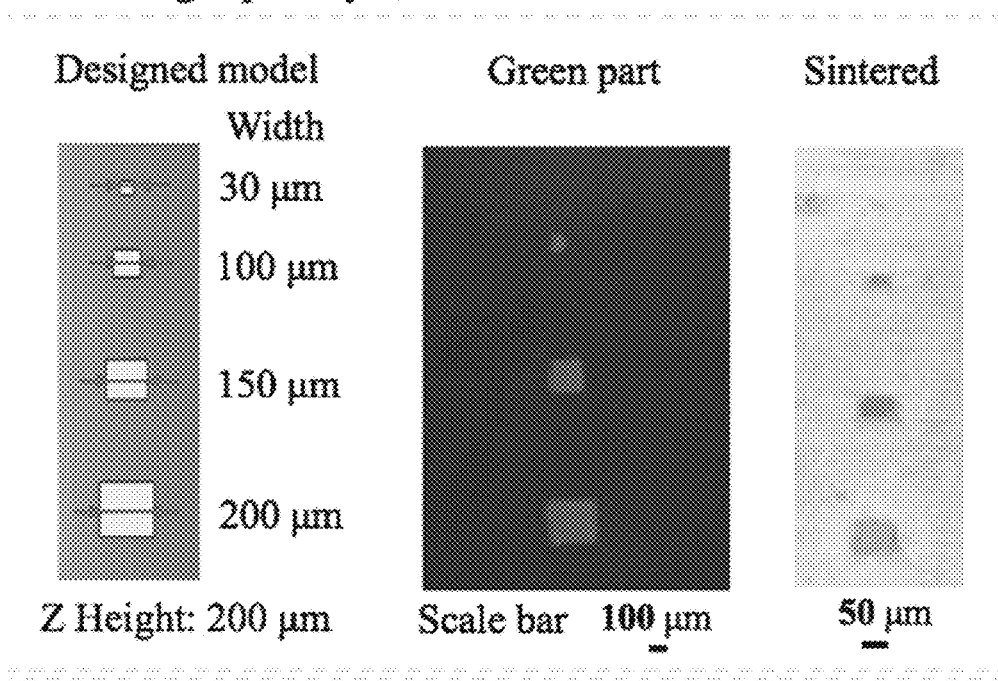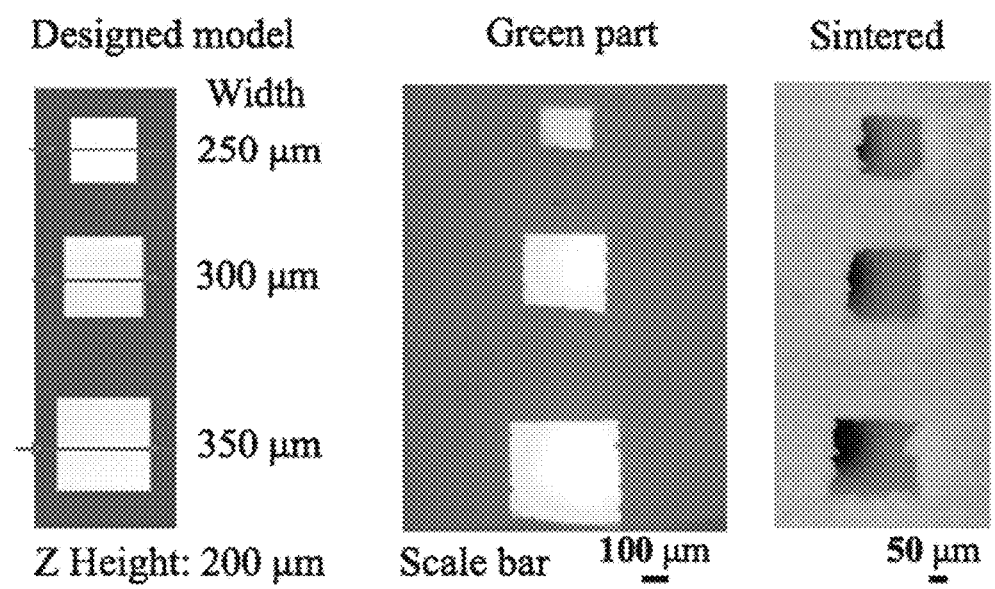
FIG. 41 (B)

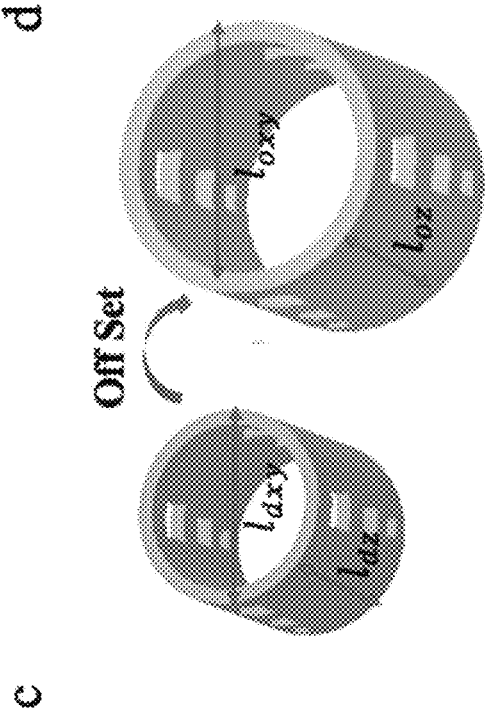
FIGS. 41 (C-D)

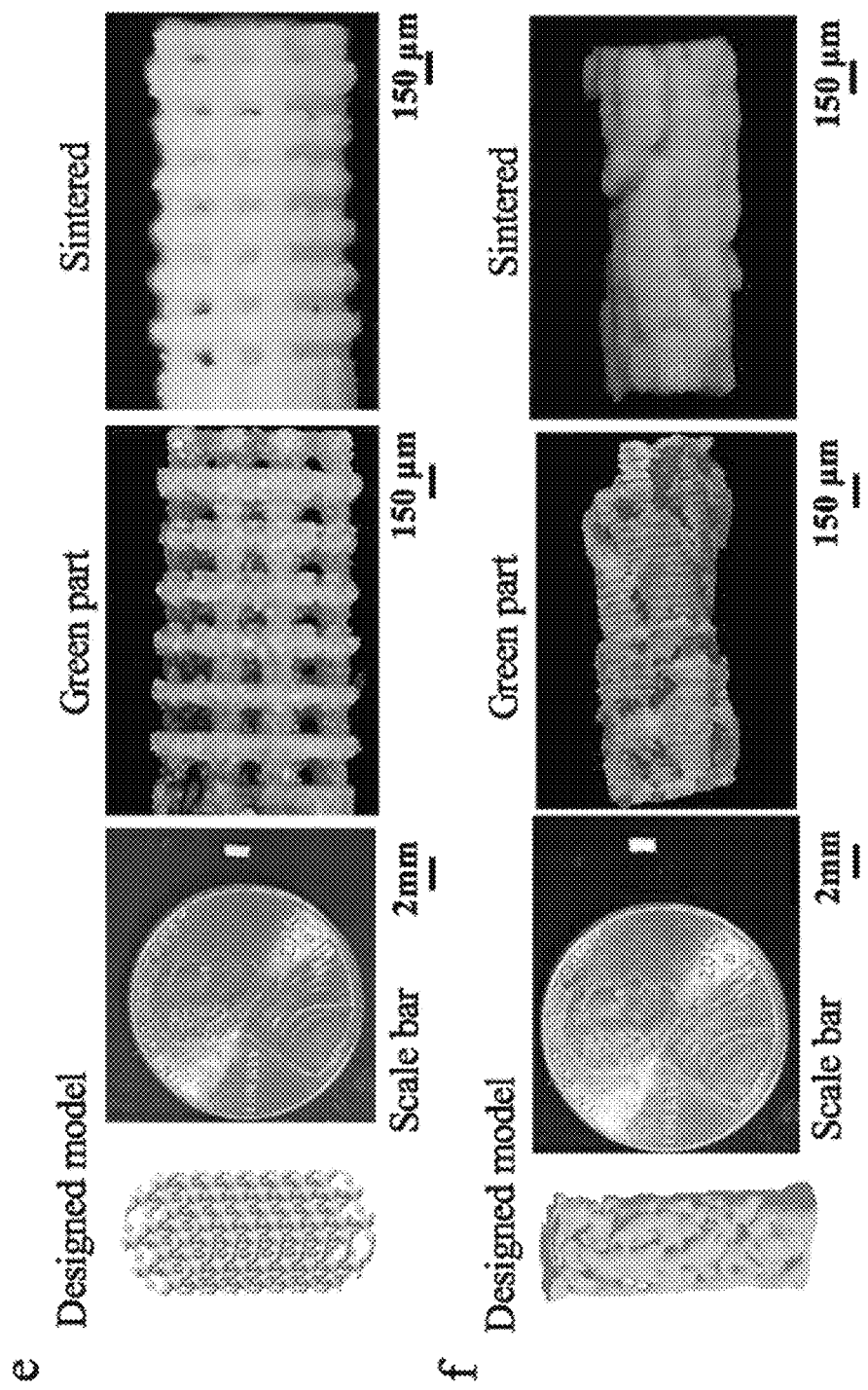
FIGS. 41 (E-F)

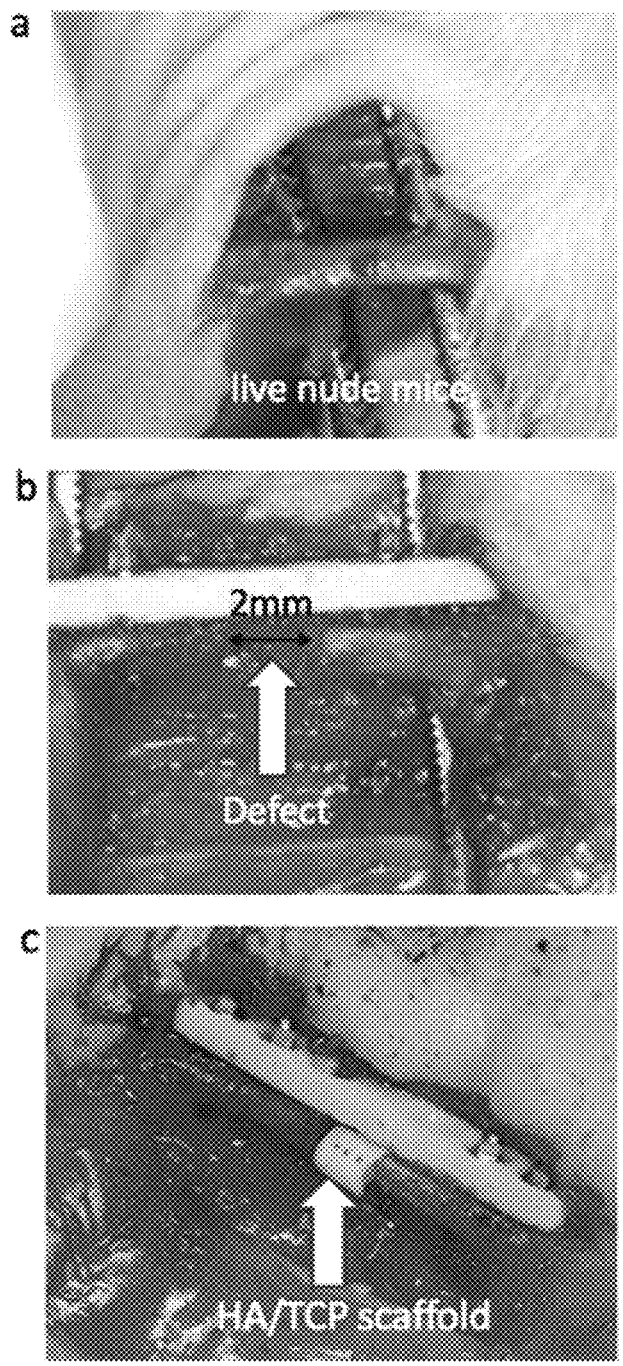
FIGS. 43 (A-C)

STEM CELLS AND DEVICES FOR BONE REGENERATION

CROSS-REFERENCE TO RELATED APPLICATIONS

The present application is a United States National Phase under 35 U.S.C. § 371 of International Application No. PCT/US2018/059860 entitled "STEM CELLS AND DEVICES FOR BONE REGENERATION" and filed on Nov. 9, 2018, which claims the benefit of U.S. provisional patent application 62/584,052, entitled "Stem Cells and Devices For Bone Regeneration," filed Nov. 9, 2017, the entire contents of both of which are incorporated herein by reference.

BACKGROUND

Technical Field

This invention relates to a bone regeneration product comprising at least one stem cell and at least one scaffold. This invention further relates to a bone regeneration product comprising at least one stem cell and at least one scaffold; wherein the scaffold comprises any scaffold suitable for carrying the at least one stem cell. This invention further relates to a bone regeneration product comprising at least one stem cell and at least one scaffold; wherein the scaffold comprises any 3D-printed scaffold suitable for carrying the at least one stem cell. This invention relates to a bone regeneration product comprising a stem cell formulation. The stem cells suitable for this invention may comprise stem cells suitable for a dense bone regeneration, stem cells suitable for a spongy bone regeneration, or a combination thereof. The bone regeneration product may further comprise a growth factor. This invention also relates to a bone regeneration method. This invention also relates to a treatment of any bone that has a critical size defect. This invention also relates to a scaffold. This invention further relates to a 3D printed scaffold. This invention also relates to a scaffold comprising hydroxyapatite (HA) and tricalcium phosphate (TCP). This invention also relates to a scaffold comprising hydroxyapatite (HA), tricalcium phosphate (TCP), and a polymer. This invention also relates to a scaffold comprising a polymer. The polymer of this invention may be prepared by using photocurable polymers and/or monomers. The scaffold of this invention may comprise a growth factor. The scaffold of this invention may comprise a growth factor and a small molecule. The small molecule may be a Smurf1 inhibitor.

Description of Related Art

Critical-size defects (CSDs) in bones caused by incidents of trauma, disease, or tumor resection are a significant challenge in the clinic. An example of a patient with a CSD is shown in Ziran and Smith, Patient Safety in Surgery 2014, 8:40. The entire content of this document is incorporated herein by reference. Patients with CSDs in long bones suffer from prolonged recovery and a compromised quality of life. In the normal bone regeneration process, healing proceeds in a well-orchestrated sequence of overlapping stages, including inflammation, proliferation, and remodeling, ultimately filling of the injury site with new bone and restoring the function of the bone tissue. In critical-size bone defects, lack of vascularity and osteoinductive factors are the major contributors to the failed healing (Stevenson, 1998).

Currently, the gold standard treatment strategy for critical-sized defects utilizes vascularized bone grafts, which provide adequate blood supply, comprising various types of cells, such as mesenchymal stem cells, osteoblasts, and osteoclasts, that contribute to remodeling ability (Soucacos et al., 2011).

However, compared to the high union rate of fibular grafts in the upper extremities, grafts in the lower extremities have fracture rates ranging from 15% to over 40%, due mainly to excessive mechanical stress or misalignment (de Boer et al., 1990; Lee et al., 2004; Minami et al., 2000). Donor site morbidity and infection are also common issues after fibular grafting (Arai et al., 2002). Due to these issues and other disadvantages of the current treatment modalities, alternative regenerative strategies are needed to improve healing outcomes and reduce complications.

Adult stem cells are well known for their regenerative capacity (Qin et al., 2014; Sponer et al., 2014). Recently, many different kinds of mesenchymal stem cells have been used in bone regeneration, such as bone marrow mesenchymal stem cells (BMMSCs) and adipose-, dental pulp-, and cranial neural crest cell (CNCC)-derived MSCs (Chung et al., 2009; Du et al., 2018; Li et al., 2016; Liu et al., 2011).

The vertebrate neural crest is a multipotent cell population derived from the lateral ridges of the neural plate. This multipotency is modified by growth factor signaling pathways and their downstream transcription factors, such that cranial neural crest derived mesenchymal stem cells (CNCCs) eventually become committed to one of a number of different cell types. Derivatives of CNCCs include sensory neurons, autonomic neurons, glia, melanocytes, adrenal medulla cells, and smooth muscle cells. During craniofacial development, CNCCs migrate ventrolaterally as they populate the branchial arches. CNCC migration from the midbrain and anterior hindbrain into the first branchial arch begins around the 4-somite stage. Eventually, those CNCCs give rise to mesenchymal structures such as bone, cartilage, and teeth, in addition to neural tissues.

Previous studies, in which individual premigratory or migratory CNCCs are labeled with dye and the fates of their descendants are then followed, have suggested that CNCCs can give rise to multiple types of derivatives from a single progenitor cell. Clonal analysis confirms this finding and demonstrates that these cells self-renew and share some of the unique characteristics of stem cells. However, some individual CNCCs give rise to only one type of derivative. Thus, it has been proposed that even at the onset of migration, the neural crest is composed of a heterogeneous population of cells with different proliferation and differentiation potentials. Interestingly, multipotent CNCCs have also been identified in adult animals where post-migratory CNCCs reside. This implies that some of the premigratory CNCCs maintain their multipotent differentiation ability and undergo self-renewal or become quiescent after migration. However, the extent to which post-migratory CNCCs maintain stem cell characteristics is unknown.

In parallel, mesenchymal stem cells (MSCs) were first identified in the bone marrow as a group of colony-forming cells with osteogenic, chondrogenic and adipogenic potential (Friedenstein et al., 1968). Subsequently, MSCs from various tissues, including skeletal muscle (Dellavalle et al., 2011), adipose tissue (Tang et al., 2008; Zuk et al., 2002), placenta (Covas et al., 2008), endometrium (Schwab and Gargett, 2007), deciduous teeth (Miura et al., 2003), and bone (Pittenger et al., 1999), have been identified. Similarities between MSCs and perivascular cells have been suggested (Covas et al., 2008; Schwab and Gargett, 2007). The most important properties of MSCs include their capacity for multi-potential differentiation and their immunomodulation abilities. MSCs are able to differentiate into different tissues including osteoblasts, chondrocytes, adipocytes or even neurons (Keating, 2012). Although MSCs have been extensively studied, their in vivo identity, physiological functions and supporting niche remain elusive. The definition of MSCs is based on a loose set of criteria including tri-lineage differentiation ability and expression of various MSC surface markers (Bianco et al., 2013; Dominici et al., 2006; Keating, 2012). Bone marrow MSCs have been shown to promote bone regeneration following injury. The entire content of each of these documents is incorporated herein by reference.

Long bone tissue is composed of cortical bone (mainly bone matrix) surrounding the soft, highly vascular bone marrow. The bone matrix provides structural support for the body, whereas bone marrow helps supply blood and related nutrient materials. Previous studies have shown that CNCCs are more robust in proliferation and produce more cortical bone when implanted in calvarial injury sites, whereas BMMSCs produce more bone marrow, suggesting that the organization and relative amounts of these components will affect the quality of new bone created with tissue engineering (Chung et al., 2009; Leucht et al., 2008).

Craniofacial bones differ from long bones in their intramembranous versus endochondral ossification, and they contain significantly less marrow space than long bones. Owing to the latter quality, the bones of the face and skull are densely cortical, in contrast to the spongy, trabecular quality of long bones. The density of craniofacial bones is crucial for the protection of important structures including the brain and the sensory organs. Thus, craniofacial bones protect our interface with the world. Damage to these bones is detrimental not only to the function of these structures, but also to the identity of the patient, as it can quite literally change the face that is presented to the world.

Due to an increase in the overall survival of neurotraumatic events such as open skull trauma, stroke, and subarachnoid hemorrhage necessitating decompressive craniectomy, the number of cranioplasties performed in the US now exceeds 5,000 each year (Ng & Nawaz, J Craniofac Surg, 2014). Incidents of head trauma, congenital defects, disease, and even tumor resection often leave patients with large or full-thickness calvarial defects that are incapable of healing on their own.

These critical-sized defects (CSDs) are currently treated by surgeons using metal or plastic implants, which are inconvenient for the patient and inferior architecturally to natural bone. Resorbable plates have tensile strength only for 3-4 weeks and often take longer than a year to resorb, decreasing opportunities for a more natural interface to develop. Furthermore, the use of implants and plates precludes the regeneration of a suture in cases where suture structure is lost (Mardas et al., J Craniofac Surg, 2002).

The suture is significant in cases of injury because it contributes mesenchymal stem cells (MSCs) that are largely responsible for injury repair of the calvarial bone (Zhao et al., Nature Cell Biology, 2015). Regenerating the suture in a calvarial defect is especially important for pediatric patients whose brains continue to grow in concert with the natural calvaria, supported by suture MSCs. Only biological materials can participate in such a process of growth and feedback.

Bone grafting is another solution offered by surgeons. For injuries of critical size, there is not enough autologous supply of bone elsewhere in the body suitable for grafting. Bone transplantation often results in tissue rejection or, particularly in pediatric patients, in resorption (Lam et al., Craniomaxillofacial Trauma Reconstruction, 2015). Bone grafting also causes additional trauma to the body, which should be avoided if possible.

Current solutions for craniofacial defects of critical size are thus unsatisfactory. There is a significant need for improved treatment of critical-size calvarial defects.

In the last decade, MSCs have become increasingly popular in injury repair studies for their ability to differentiate into osteoblasts, chondrocytes, adipocytes, myocytes, and neuron-like cells (Jiang et al., Nature, 2002). Stem cells delicately orchestrate homeostasis by proliferating in response to damaged tissue (Biteau et al., Cell Stem Cell, 2011). Ideally, cranial defects would be healed using a stem cell population that can properly regulate cortical bone homeostasis.

Recent advances in bio-printing are being explored to overcome these shortfalls of the treatment of CSDs and are presenting opportunities for biomedical engineers to design the shape of scaffold based on the requirement (Nyberg et al.). There are several solid free-form fabrication (SFF) methods for the manufacturing of 3D scaffold. Extrusion based printing process is one of the common bio-printing methods to fabricate the scaffold using thermal polymer like PLG and PLA.

Due to the printing capability, extrusion based method is hard to fabricate the scaffold with complex 3D micro-scale structures. For example, PCL/TCP and PCL/HA based composite scaffolds were fabricated by fused deposition modelling (FDM), which the fiber diameter is bigger than 200 $\mu$m (Nyberg et al.). To achieve high percentage HA/TCP, hybrid processes were developed. In such processes, HA, or TCP powder with the binder were first formed to a 3D shape ("green part") using 3D printing methods, and then the inside binder was removed by post-processing, such as high temperature sintering, and/or chemical dissolution (Leukers et al., Zeng et al., Witek, Diogo et al., He at al., Castilho et al., Zhang et al., Trombetta et al.). Only submicron pores between the HA/TCP particles were generated after the post-processing. Therefore, it is necessary to build the scaffold with micro-scale holes to promote the transportation of nutrition and cell attachment. However, only macro-scale scaffolds with hundreds micron holes were fabricated by above printing processes.

Micro-scale structures, which the feature size is smaller than 100 $\mu$m, are hard to print using extrusion based 3D printing methods due to the limitation of printing capability (Diogo et al., He at al., Castilho et al., Zhang et al., Trombetta et al., Nadeem et al.). What's more, the geometric shape of printed scaffold was relatively simple, like mesh matrix, because the extruded composite filament only can stack simple structures to avoid the support and deformation (Diogo et al., He at al., Castilho et al., Zhang et al., Trombetta et al., Nadeem et al.).

For bone regeneration, there are demands of the scaffolds with complex geometric shape and hierarchical porous structures ranging from hundreds of micrometers to less than one micrometer (Nadeem et al., DiLuca et al.). It is of great importance to develop a 3D printing process, which can fabricate composite scaffold with biomimetic hierarchical porous structures for the further study of new bone regrowth (Yang, Y et al, Holmes et al., Salerno et al., Yang, J. Z. et al.).

For in detail discussion of tissue regeneration products, for example, see: Sherwood et al. "Composites for tissue regeneration and methods of manufacture thereof" U.S. Pat. No. 6,454,811; Teoh et al. "Three-dimensional bioresorbable scaffolds for tissue engineering applications" U.S. Pat. No. 7,968,026; Lin et al. "Engineered scaffolds for intervertebral disc repair and regeneration and for articulating joint repair and regeneration" U.S. Pat. No. 8,275,594; Xuenong et al. "Orthopaedic implant for supporting tissue growth and methods of forming the implant and tissue" U.S. Pat. No. 8,895,046; Roeder et al. "Tissue scaffolds having bone growth factors" U.S. Pat. No. 9,550,012; Xuenong et al. "Bone tissue engineering by ex vivo stem cells ongrowth into three-dimensional trabecular metal" U.S. Patent Application Publication No. 2005/0272153; Pasini et al. "Bone replacement implants with mechanically biocompatible cellular material" U.S. Patent Application Publication No. 2014/0363481; Biris "Bone regeneration using biodegradable polymeric nanocomposite materials and applications of the same" U.S. Patent Application Publication No. 2015/0039097; Zhang et al. "Multi-step method for fabricating tissue engineering bone".S. Patent Application Publication No. 2016/0058911; Grayson, "Bone regeneration using stromal vascular fraction, platelet-derived growth factor-rich hydrogel, three-dimensional printed poly-epsilon-caprolactone scaffolds" U.S. Patent Application Publication No. 2016/0095958; and Cox et al. "Crosslinkable 3d printed biomaterial-based implants and methods of manufacture thereof" U.S. Patent Application Publication No. 2016/0184480. The entire content of each of these documents is incorporated herein by reference.

Natural bone tissue is composed of honeycomb-like hierarchical porous structures that support cells for their growth, provide space for nutrition transportation, and endure different type of ambient load (Basu et al.). Traditionally, the medical treatment to deal with critical defects of bone is to implant a biocompatible bone graft, which is made by tough but light materials including metal, composite or bio-ceramics (Wang et al., Petit et al.). However, these inserted implantations cannot fully serve functions as human natural bone (Basu et al., Wang et al.). To heal the bone critical defects, a potential solution is to regenerate bone tissue by utilizing three-dimensional (3D) scaffold cultured with patient's cell (Wang et al.). During the degradation of scaffold, new bone tissue can gradually grow back to heal defects by culturing bioactive cells with sufficient nutrition supply (refer to FIG. 36(a)). For 3D scaffold, the porous structure provides sufficient space for cells to attach on, and the crisscrossed inner pore network enables blood vessel to easily deliver the nutrition anywhere within the scaffold (Wang et al.). Besides, the material of scaffold also has effects on the bone tissue regeneration, and is required to be biocompatible, biological nontoxic and biodegradable. Overall, both material and structures of scaffold play critical roles in the healing of bone defects (Bose et al., Rengier et al.).

Hydroxyapatite (HA) nanopowder showed promising properties in tissue application because it is able to promote adhesion and proliferation of bone-forming cells by incorporating in the biodegradable polymer composite (Kim et al.) or depositing on biocompatible substrates (Sato et al.). Tricalcium phosphate (TCP), one main constituent of natural human bone, is one kind of biodegradable bio-ceramic that is widely used to fabricate bone graft substitute for bone treatment and orthopedic surgery (Wang et al., Petit et al, Ho et al., Shao et al.).

Many different techniques, such as solvent casting, particulate leaching, phase separation, melt molding, high-pressure pressing, and forging, have been developed to fabricate HA/TCP based 3D scaffolds (Macchetta et al., Miao et al.). However, geometrical structures of HA/TCP scaffolds fabricated by these methods are regularly simple, setting limitations for the study of cell cultivation scaffold and bone tissue regeneration (Wang et al., Ho et al.).

Recent advances in bio-printing may show the possibility to overcome these shortfalls, and reveal the potential for biomedical engineers to design customized scaffolds based on surgery requirements (Ho et al., Kim et al.). Several 3D printing methods were developed for the manufacturing of HA/TCP scaffold with specially designed geometric structures (Shao et al., Nyberg et al, Leukers et al., Leukers et al., Zeng et al. Cox et al., Wu et al., Kon et al., Kim et al., Witek et al.). For example, PCL/TCP and PCL/HA based composite scaffolds were fabricated by fused deposition modelling (FDM), where the fiber diameter is bigger than 200 μm (Nyberg et al.).

A hybrid process was developed to achieve high percentage of HA/TCP concentration. Specifically, HA or TCP powder mixed with the binder was used in the 3D printing process to form 3D object (named green part), and then inside binder was removed by post-processing, such as high temperature sintering or chemical dissolution (Leukers et al., Leukers et al., Zeng et al. Witek et al., Diogo et al., He et al, Castilho et al., Zhang et al.). For instance, β-TCP paste, consisting of β-TCP powder and PVA solution, was firstly accumulated to 3D mesh matrix using injection based printing method, and final mesh shaped bare β-TCP scaffold was obtained after sintering at 1100 Celsius (Wu et al.).

Similarly, HA/TCP scaffold was fabricated by the extrusion based printing process, and the polymeric additives inside were burned out after heating over 625 Celsius (Witek et al.). After the post-processing, only submicron pores were generated between HA/TCP particles (Zeng et al., Witek et al., Diogo et al., He et al, Castilho et al., Zhang et al., Trombetta et al., Castilho et al.), and such inner structure is too dense to provide cell with necessary space for the exchange of nutrition and metabolism during its growth. Therefore, it is necessary to build HA/TCP scaffold with hierarchical porous structure ranging from hundreds of microns to submicron level, to maintain stabilized nutrition transportation and cell metabolism.

However, most 3D printing processes can only fabricate macro-scale HA/TCP scaffolds with holes at hundreds micron level. Due to the limitation on printing resolution, micro-scale features whose sizes are smaller than 100 μm are difficult to be fabricated by them (Kim et al., Witek et al., Diogo et al., He et al, Castilho et al., Zhang et al., Trombetta et al., Castilho et al., Nadeem et al.). Furthermore, geometrical shape limitations exist for the HA/TCP scaffold fabricated by the extrusion based 3D printing process, because HA/TCP slurry filiment can only be stacked layer by layer to avoid distortion and support addition (Kim et al., Witek et al., Diogo et al., He et al, Castilho et al., Zhang et al., Trombetta et al.).

To address the increasing demands of HA/TCP scaffolds with complex geometric shapes and hierarchical porosity for the study of bone tissue regeneration (Nadeem et al., Di Luca et al.), it is of great importance to develop a 3D printing process that can fabricate HA/TCP scaffold with biomimetic hierarchical porous structures for further study of issues in bone tissue regeneration (Yang, Y. et al., Holmes et al., Salerno et al., Yang, J. Z. et al., Yang, Y. et al.).

Compared with most other 3D printing methods, mask image projection based stereolithography (MIP-SL) has the capability of fabricating freeform surface model with relatively complex inner structures (Li et al., Yang, Y. et al., Zhou, C. et al., Li et al, Zhou et al.). Using the macro-scale MIP-SL process, photopolymers mixed with bio-ceramic can be firstly solidified by high resolution light projection, and later the photo-curable polymer is completely burned out after high temperature sintering process (Zeng et al., Song et al. (2015), Son et al. (2017)). The processing resolution of macro-scale MIP-SL, however, cannot fulfil the requirement of micro-scale features fabrication.

RELATED ART REFERENCES

The following publications are related art for the background of this disclosure.

Arai, K., Toh, S., Tsubo, K., Nishikawa, S., Narita, S., and Miura, H. (2002). Plast Reconstr Surg 109, 2301-6.

Basu, Bikramjit 2017, Biomaterials for Musculoskeletal Regeneration. Springer, 45-85.

Biteau B, Hochmuth C E, Jasper H. Maintaining tissue homeostasis: dynamic control of somatic stem cell activity. Cell stem cell. 2011; 9(5):402-411. doi:10.1016/j.stem.2011.10.004.

Boccaccini, A. R., and Trusty, P. A. 1998, Materials characterization 41(4) 109-121 Surname A and Surname B 2009 Journal Name 23 544.

Bose, S., Vahabzadeh, S., and Bandyopadhyay, A. 2013, Materials today 16(12) 496-504.

Castilho, M., Moseke, C., Ewald, A., Gbureck, U., Groll, J., Pires, I., . . . & Vorndran, E 2014 Biofabrication 6(1) 015006.

Chung, I. H., Yamaza, T., Zhao, H., Choung, P. H., Shi, S., and Chai, Y. (2009). Stem Cells 27, 866-77.

Cooper G M, Mooney M P, Gosain A K, Campbell P G, Losee J E, Huard J. Testing the critical size in calvarial bone defects: revisiting the concept of a critical-size defect. Plast Reconstr Surg. 2010 June; 125(6):1685-92. doi: 10.1097/PRS.0b013e3181cb63a3. PubMed PMID: 20517092; PubMed Central PMCID: PMC2946111.

Cox, S. C., Thornby, J. A., Gibbons, G. J., Williams, M. A., Mallick, K. K. 2015, Materials Science and Engineering: C 47 237-247.

de Boer, H. H., Wood, M. B., and Hermans, J. (1990). Int Orthop 14, 121-8.

Deng, X. G., Wang, J. K., Zhang, H. J., Liu, J. H., Zhao, W. G., Huang, Z., and Zhang, S. W. 2016, Advances in Applied Ceramics 115(4) 204-209.

Di Luca, A., Longoni, A., Criscenti, G., Mota, C., van Blitterswijk, C., & Moroni, L 2016 Biofabrication 8(4) 045007.

Diogo, G. S., Gaspar, V. M., Serra, I. R., Fradique, R., & Correia, I. J 2014 Biofabrication 6(2) 025001.

Du, J., Xie, P., Lin, S., Wu, Y., Zeng, D., Li, Y., and Jiang, X. (2018). ACS Appl Mater Interfaces.

Frisch, Uriel, Brosl Hasslacher, and Yves Pomeau. 1986, Physical review letters 56.14 1505.

Griffith, Michelle L., and John W. Halloran. 1996, Journal of the American Ceramic Society 79.10 2601-2608.

He, F., Qian, G., Ren, W., Li, J., Fan, P., Shi, H., Ye, J 2017 Biofabrication 9(2) 025005.

Heunisch, A., Dellert, A., and Roosen, A. 2010, Journal of the European Ceramic Society 30(16) 3397-3406.

Ho, C. M. B., Ng, S. H., and Yoon, Y. J. 2015, International Journal of Precision Engineering and Manufacturing 16(5) 1035-1046.

Hollister, S. J. 2009, Advanced materials 21(32-33) 3330-3342.

Holmes, B., Bulusu, K., Plesniak, M., & Zhang, L. G 2016 Nanotechnology 27(6) 064001.

Jacobs, Paul Francis. 1992, Society of Manufacturing Engineers.

Jiang Y, Jahagirdar B N, Reinhardt R L, Schwartz R E, Keene C D, Ortiz-Gonzalez X R, Reyes M, Lenvik T, Lund T, Blackstad M, Du J, Aldrich S, Lisberg A, Low W C, Largaespada D A, Verfaillie C M (2002). "Pluripotency of mesenchymal stem cells derived from adult marrow". Nature. 418 (6893): 41-49. doi:10.1038/nature00870. PMID 12077603.

Jordan, M. M., Montero, M. A., Meseguer, S., and Sanfeliu, T. 2008, Applied Clay Science 42(1-2) 266-271.

Kim, J., McBride, S., Tellis, B., Alvarez-Urena, P., Song, Y. H., Dean, D. D., and Hollinger, J. O. 2012, Biofabrication 4(2) 025003.

Kim, S. S., Park, M. S., Jeon, O., Choi, C. Y., Kim, B. S. 2006, Biomaterials 27(8) 1399-1409.

Kon, E., Muraglia, A., Corsi, A., Bianco, P., Marcacci, M., Martin, I., and Giardino, R. 2000, Journal of Biomedical Materials Research: An Official Journal of The Society for Biomaterials and The Japanese Society for Biomaterials 49(3) 328-337.

Lee, K. S., Han, S. B., and Baek, J. R. (2004), J. Reconstr Microsurg 20, 277-84.

Leucht, P., Kim, J. B., Amasha, R., James, A. W., Girod, S., and Helms, J. A. (2008). Development 135, 2845-54.

Leukers, B., Mikan, H., Irsen, S. H., Milz, S., Tille, C., Schieker, M., & Seitz, H 2005 Journal of Materials Science: Materials in Medicine 16(12) 1121-1124.

Li, X., Chen, Y. 2017, Journal of Manufacturing Processes 28 531-540.

Li, X., Xie, B., Jin, J., Chai, Y., Chen, Y. 2018, Procedia Manufacturing 26 1023-1033.

Li, Y., Zhao, S., Nan, X., Wei, H., Shi, J., Li, A., and Gou, J. 2016, Stem Cell Research & Therapy 7, 141.

Lim, K. S., Levato, R., Costa, P. F., Castilho, M. D., Alcala-Orozco, C. R., van Dorenmalen, K. M., and Woodfield, T. B. 2018, Biofabrication 10(3) 034101.

Liu, Y., Wang, L., Kikuiri, T., Akiyama, K., Chen, C., Xu, X., Yang, R., Chen, W., Wang, S., and Shi, S. (2011). Nat Med 17, 1594-601.

Macchetta, A., Turner, I. G., Bowen, C. R. 2009, Acta Biomaterialia 5(4) 1319-1327.

Mardas N, Kostopoulos L, Karring T. Bone and suture regeneration in calvarial defects by e-PTFE-membranes and demineralized bone matrix and the impact on calvarial growth: an experimental study in the rat. J Craniofac Surg. 2002 May; 13(3):453-62; discussion 462-4. PubMed PMID: 12040218.

Miao, X., Tan, D. M., Li, J., Xiao, Y., and Crawford, R. 2008, Acta Biomaterialia 4(3) 638-645.

Minami, A., Kasashima, T., Iwasaki, N., Kato, H., and Kaneda, K. (2000). J Bone Joint Surg Br 82, 1022-5.

Nadeem, D., Smith, C. A., Dalby, M. J., Meek, R. D., Lin, S., Li, G., & Su, B 2015 Biofabrication 7(1) 015005.

Ng Z Y, Nawaz I. Computer-designed PEEK implants: a peek into the future of cranioplasty? J Craniofac Surg. 2014 January; 25(1):e55-8. doi: 10.1097/SCS.0b013e3182a2f7b6. PubMed PMID: 24406603.

Nyberg, E., Rindone, A., Dorafshar, A., & Grayson, W. L 2017 Tissue Engineering Part A 23(11-12) 503-514.

Pan, Y., Zhou C., Chen, Y. 2012, ASME Journal of Manufacturing Science and Engineering, 134(5) 051011.

Park S, Zhao H, Urata M, Chai Y. Sutures Possess Strong Regenerative Capacity for Calvarial Bone Injury. Stem Cells Dev. 2016 Dec. 1; 25(23):1801-1807. Epub 2016 Oct. 24. PubMed PMID: 27762665; PubMed Central PMCID: PMC5124738.Li, Y., Zhao, S., Nan, X., Wei, H., Shi, J., Li, A., and Gou, J. (2016). Stem Cell Research & Therapy 7, 141.

Petit, R. 1999, European Journal of Orthopaedic Surgery & Traumatology 9(2) 71-74.

Qin, Y., Guan, J., and Zhang, C. (2014). Postgrad Med J 90, 643-7.

Rice, R. W. 1993, Journal of materials science 28.8 2187-2190.

Rengier, F., Mehndiratta, A., Von Tengg-Kobligk, H., Zechmann, C. M., Unterhinninghofen, R., Kauczor, H. U., and Giesel, F. L. 2010, International journal of computer assisted radiology and surgery 5(4) 335-341.

Salerno, A., Diéguez, S., Diaz-Gomez, L., GOrnez-Amoza, J. L., Magariños, B., Concheiro, A., . . . & Garcia-González, C. A 2017 Biofabrication 9(3) 035002.

Sato, M., Sambito, M. A., Aslani, A., Kalkhoran, N. M., Slamovich, E. B., and Webster, T. J. 2006, Biomaterials 27(11) 2358-2369.

Shao, H., Ke, X., Liu, A., Sun, M., He, Y., Yang, X., and Xu, S. 2017, Biofabrication 9(2) 025003.

Song, X., Chen, Y., Lee, T., Wu, Sh., Cheng, L. 2015, SME Journal of Manufacturing Processes, 20 456-464.

Song, X., Chen, Z., Lei, L. Shung, K., Zhou, Q., Chen, Y. 2017, Rapid Prototyping Journal 23(1).

Song, X., Zhang, Z., Chen, Z., Chen, Y. 2016, ASME Journal of Manufacturing Science and Engineering, 139(3), 031015.

Soucacos, P. N., Korompilias, A. V., Vekris, M. D., Zoubos, A., and Beris, A. E. (2011). Microsurgery 31, 190-7.

Sponer, P., Kucera, T., Diaz-Garcia, D., and Filip, S. (2014). Eur J Orthop Surg Traumatol 24, 257-62.

Stevenson, S. (1998). ClinOrthopRelat Res, S239-46.

Tabachnick, B. G., Fidell, L. S. 2007, Thomson/Brooks/Cole.

Trombetta, R., Inzana, J. A., Schwarz, E. M., Kates, S. L., & Awad, H. A 2017 Annals of biomedical engineering 45(1) 23-44.

Wang, Q., Xu, J., Jin, H., Zheng, W., Zhang, X., Huang, Y., Qian, Z. 2017, Chinese Chemical Letters 28 (9) 1801-1807.

Witek, Lukasz 2015 Oklahoma State University.

Wu, C., Xia, L., Han, P., Xu, M., Fang, B., Wang, J., and Xiao, Y. 2015, Carbon 93 116-129.

Xu, K., Kwok, T., Zhao Zh., Chen, Y. 2017, ASME Journal of Computing and Information Science in Engineering, 17(2) 021009.

Yang, J. Z., Hu, X. Z., *Sultana*, R., Day, R. E., & Ichim, P 2015 Biomedical Materials 10(4) 045006.

Yang, Y., Li, X., Zheng, X., Chen, Z., Zhou, Q., Chen, Y. 2018, Advanced Materials 30(9) 1704912.

Yang, Y., Song, X., Li, X., Chen, Z., Zhou, C., Zhou, Q., & Chen, Y 2018 Advanced Materials 1706539.

Ye Li, Shu-Kui Chen, Long Li, Ling Qin, Xin-Luan Wang, Yu-Xiao Lai. Bone defect animal models for testing efficacy of bone substitute biomaterials. Journal of Orthopaedic Translation. 2015 July; Volume 3, Issue 3, 95-104. https://doi.org/10.1016/j.jot.2015.05.002.

Zeng, Y., Yan, Y., Yan, H., Liu, C., Li, P., Dong, P., . . . & Chen, J 2018 Journal of Materials Science 53(9) 6291-6301.

Zhang, Y., Zhai, D., Xu, M., Yao, Q., Zhu, H., Chang, J., & Wu, C 2017 Biofabrication 9(2) 025037.

Zhao H, Feng J, Ho T V, Grimes W, Urata M, Chai Y. The suture provides a niche for mesenchymal stem cells of craniofacial bones. Nat Cell Biol. 2015 April; 17(4):386-96. doi: 10.1038/ncb3139. Epub 2015 Mar. 23. PubMed PMID: 25799059; PubMed Central PMCID: PMC4380556.

Zhou, C., Chen, Y., Waltz, R. A. 2009, Journal of Manufacturing Science and Engineering, 131(6) 061004.

Zhou, C., Chen, Y., Yang, Z., Khoshnevis, B., 2013, Rapid Prototyping Journal, 19(3) 153-165.

Zissi, S., Bertsch, A., Jezequel, J. Y., Corbel, S., Lougnot, D. J., and Andre, J. C. 1996, Microsystem technologies 2(2) 97-102.

The entire content of each of above publications is incorporated herein by reference.

SUMMARY

This invention relates to a bone regeneration product comprising at least one stem cell and at least one scaffold. This invention further relates to a bone regeneration product comprising at least one stem cell and at least one scaffold; wherein the scaffold comprises any scaffold suitable for carrying the at least one stem cell. This invention further relates to a bone regeneration product comprising at least one stem cell and at least one scaffold; wherein the scaffold comprises any 3D-printed scaffold suitable for carrying the at least one stem cell. This invention relates to a bone regeneration product comprising a stem cell formulation. The stem cells suitable for this invention may comprise stem cells suitable for a dense bone regeneration, stem cells suitable for a spongy bone regeneration, or a combination thereof. The bone regeneration product may further comprise a growth factor. This invention also relates to a bone regeneration method. This invention also relates to a treatment of any bone that has a critical size defect. This invention also relates to a scaffold. This invention further relates to a 3D printed scaffold. This invention also relates to a scaffold comprising hydroxyapatite (HA) and tricalcium phosphate (TCP). This invention also relates to a scaffold comprising hydroxyapatite (HA), tricalcium phosphate (TCP), and a polymer. This invention also relates to a scaffold comprising a polymer. The polymer of this invention may be prepared by using photocurable polymers and/or monomers. The scaffold of this invention may comprise a growth factor. The scaffold of this invention may comprise a growth factor and a small molecule. The small molecule may be a Smurf 1 inhibitor.

The bone regeneration products and methods of this disclosure may comprise a scaffold; a scaffold and a growth factor; a scaffold, a growth factor and a Smurf 1 inhibitor; stem cells; or stem cells and a scaffold; or stem cells, a scaffold and a growth factor; or stem cells, a scaffold, a growth factor, and a Smurf 1 inhibitor. The scaffolds of this disclosure may be suitable in hosting these cells and/or a growth factor and/or a Smurf 1 inhibitor.

In this disclosure, the bone regeneration product may comprise a mesenchymal stem cell (MSC) formulation, and a scaffold. The MSC formulation may comprise a stem cell mixture. The stem cell mixture may comprise dense bone regenerating stem cells (DBR-SCs), spongy bone regenerating stem cells (SBR-SCs), or a mixture thereof.

In this disclosure, the DBR-SCs may comprise dental pulp stem cells, dental pulp tissue derived neural crest cells, stem cells from human exfoliated deciduous teeth, periodontal ligament stem cells, dental follicle stem cells, tooth germ progenitor cells, stem cells from the apical papilla, oral epithelial progenitor/stem cells, gingiva-derived mesenchymal stem cells, suture stem cells, or a mixture thereof. The DBR-SCs may comprise cranial neural crest derived mesenchymal stem cells (CNCCs), dental pulp derived stem cells (DPSCs), or a mixture thereof. The SBR-SCs may comprise bone marrow derived mesenchymal stem cell (BMMSCs), adipose tissue derived mesenchymal stem cells (AMSCs), or a mixture thereof. The SBR-SCs may comprise bone marrow derived mesenchymal stem cell (BMMSCs).

In this disclosure, the stem cell mixture may comprise DBR-SCs and SBR-SCs. The DBR-SCs may comprise dental pulp stem cells, stem cells from human exfoliated deciduous teeth, periodontal ligament stem cells, dental follicle stem cells, tooth germ progenitor cells, stem cells from the apical papilla, oral epithelial progenitor/stem cells, gingiva-derived mesenchymal stem cells, suture stem cells, or a mixture thereof; and SBR-SCs comprise bone marrow derived mesenchymal stem cell (BMMSCs), adipose tissue derived mesenchymal stem cells (AMSCs), or a mixture thereof. The MSC formulation may comprise DBR-SCs and SBR-SCs. The DBR-SCs may comprise DPSCs, CNCCs, or a mixture thereof; and SBR-SCs may comprise BMMSCs.

In this disclosure, DBR-SC concentration in the stem cell mixture may be in the range of 50% to 100% (i.e. SBR-SCs may be in the range of 0% to 50%), or in the range of 51% to 100%, or in the range of 60% to 100%, or in the range of 70% to 100%, or in the range of 80% to 100%, or in the range of 85% to 95%, or 90%. This bone regeneration product comprising such stem cell ratios (i.e. stem cell concentrations) may be particularly suitable for producing more bone matrix (i.e. denser bones) as compared to the bone regeneration product that may comprise a stem cell mixture with, for example, a DBR-SC:SBR-SC ratio of less than 1.

In this disclosure, SBR-SC concentration in the stem cell mixture may be in the range of 50% to 100% (i.e. DBR-SCs may be in the range of 0% to 50%), or in the range of 51% to 100%, or in the range of 60% to 100%, or in the range of 70% to 100%, or in the range of 80% to 100%, or in the range of 85% to 95%, or 90%. This bone regeneration product comprising such stem cell ratios (i.e. ratios) may be particularly suitable for producing bone matrix with less density (i.e. spongy bones) as compared to the bone regeneration product that may comprises a stem cell mixture with, for example, a DBR-SC:SBR-SC ratio of greater than 1.

In this disclosure, the bone regeneration product may further comprise a growth factor. In this disclosure, the stem cell formulation may further comprise a growth factor. In this disclosure, the scaffold may further comprise a growth factor. In this disclosure, the bone regeneration product may further comprise a growth factor and a Smurf 1 inhibitor. In this disclosure, the stem cell formulation may further comprise a growth factor and a Smurf 1 inhibitor. In this disclosure, the scaffold may further comprise a growth factor and a Smurf 1 inhibitor.

In this disclosure, the growth factor may comprise bone morphogenic protein (BMP), Indian hedgehog (IHH), transforming growth factor β (TGFβ); bone morphogenetic proteins (BMPs); fibroblast growth factors (FGFs); Wnt ligands and β-catenin; insulin-growth factors (IGFs); collagen-1; Runx2; osteopontin; osterix; vascular endothelial growth factor (VEGF); platelet derived growth factor (PDGF); osteoprotegerin (OPG); NEL-like protein 1 (NELL-1); or a mixture thereof. In this disclosure, the growth factor may comprise BMP, IHH, or a mixture thereof.

In this disclosure, the Smurf 1 inhibitor may comprise A01, A02, A03, A04, A05, A06, A07, A08, A09, A10, A11, A14, A15, A17, A18, A25, A54, A63, A75, phenamil, the like, or a combination thereof. In this disclosure, the Smurf 1 inhibitor may comprise A01, A17, phenamil, or a combination thereof. In this disclosure, the Smurf 1 inhibitor may comprise phenamil.

In this disclosure, the scaffold may comprise an article produced from a formulation comprising polycaprolactone (PCL), polycaprolactone dimethacrylate (PCLDA), calcium phosphate, hydroxyapatite (HA), tricalcium phosphate (TCP), polyethylene glycol diacrylate (PEGDA), gelatin methacryloyl (GeIMA), or a mixture thereof.

In this disclosure, the scaffold may comprise an article produced from a formulation comprising a polymer that is prepared by using a photo-curable monomer, a photo-curable polymer, hydroxyapatite (HA), tricalcium phosphate (TCP), or a mixture thereof. In this disclosure, the scaffold may comprise polycaprolactone (PCL), polycaprolactone dimethacrylate (PCLDA), or a mixture thereof.

In this disclosure, the scaffold may comprise at least one first chamber and at least one second chamber. The at least one first chamber may hold a mesenchymal stem cell formulation comprising a stem cell mixture, wherein concentration of DBR-SCs in the stem cell mixture is in the range of 50% to 100%, or in the range of 51% to 100% or in the range of 60% to 100%, or in the range of 70% to 100%, or in the range of 80% to 100%, or in the range of 85% to 95%, or 90%. The at least one second chamber may hold a mesenchymal stem cell formulation comprising a stem cell mixture, wherein concentration of SBR-SCs in the stem cell mixture is in the range of 50% to 100%, or in the range of 51% to 100%, or in the range of 60% to 100%, or in the range of 70% to 100%, or in the range of 80% to 100%, or in the range of 85% to 95%, or 90%.

In this disclosure, the scaffold may comprise at least at least one outer chamber and at least one inner chamber. The at least one outer chamber may hold a bone regeneration product that comprises a mesenchymal stem cell formulation comprising a stem cell mixture, wherein concentration of DBR-SCs in the stem cell mixture is in the range of 50% to 100%, or in the range of 51% to 100% or in the range of 60% to 100%, or in the range of 70% to 100%, or in the range of 80% to 100%, or in the range of 85% to 95%, or 90%. The at least one inner chamber may hold a bone regeneration product that comprises a mesenchymal stem cell formulation, comprising a stem cell mixture, wherein concentration of SBR-SCs in the stem cell mixture is in the range of 50% to 100%, or in the range of 51% to 100%, or in the range of 60% to 100%, or in the range of 70% to 100%, or in the range of 80% to 100%, or in the range of 85% to 95%, or 90%. The outer chamber may partially or substantially surround the inner chamber. The outer chamber and the inner chamber may each comprise a pore on their walls. The pore has a characteristic length. The characteristic length of the pore may be smaller than a particular size such that each stem cell can be kept confined in inner and/or outer chambers.

In this disclosure, the scaffold may comprise hydroxyapatite and tricalcium phosphate. The hydroxyapatite concentration may be in the range of 5 weight % to 30 weight % and the tricalcium phosphate concentration may be in the range of 5 weight % to 30 weight %. In this disclosure, the hydroxyapatite concentration may be in the range of 10 weight % to 20 weight % and the tricalcium phosphate concentration is in the range of 10 weight % to 20 weight %. In this disclosure, the hydroxyapatite concentration may be in the range of 15 weight % to 20 weight % and the tricalcium phosphate concentration may be in the range of 15 weight % to 20 weight %. In this disclosure, the hydroxyapatite concentration may be 15 weight % and the tricalcium phosphate concentration may be 15 weight %, or the hydroxyapatite concentration may be 20 weight % and the tricalcium phosphate concentration may be 20 weight %.

In this disclosure, the scaffold has a compressive strength in the range of 0.1 MPa to 10 MPa; or in the range of 1 MPa to 8 MPa; or in the range of 5 MPa to 7 MPa.

In this disclosure, the scaffold has a porosity in the range of 1% to 40%; or in the range of 3% to 30%; or in the range of 3% to 20%; or in the range of 3% to 10%.

Any combinations of above bone regeneration products, their features, their preparation methods, and/or their use in the treatment of bones with defects are within the scope of this disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

This patent or application file contains at least one drawing executed in color. Copies of this patent or patent application publication with color drawing(s) will be provided by the Office upon request and payment of the necessary fee.

FIG. 3. Biocompatibility and degradation tests of the PCLDA scaffold. (A) A photographic image of a PCLDA/HA/TCP scaffold, (B) Enlarged photographic image of the PCLDA/HA/TCP scaffold shown in (A), (C) Quantification of viable NIH3T3 cells after culture in vitro with PCL scaffolds for 72 hours. (D) Degradation profile of PCL scaffold attained by measuring their dry weight after 30 or 60 days of subcutaneous implantation. *, p<0.05; **, p<.

FIG. 4. Mouse CSD model. (A-I) Femoral segmental defect surgery procedure on live nude mice. (J,K) X-ray images after surgery showed that the 2 mm defect in the femur is about 10% of the whole femur length.

FIG. 5. PCLDA-based scaffold implanted in the mouse CSD model. (A) The printed scaffold implanted in the femur defect to test biodegradability. (B-F) Images of the defect from 2 days to 12 weeks (12W) post-surgery indicating that scaffold implantation alone is insufficient for bone regrowth in the CSD.

FIG. 6. Increased osteogenesis of DPSCs after IHH treatment. Alizarin red staining of DPSCs were cultured alone (control; ctrl) or with hedgehog inhibitor GDC0449 or IHH. ANOVA was performed. * indicates statistically significant difference from control and P values are indicated. n=4 samples per group.

FIG. 12. Three-point bending machine to test tensile strength of reconstructed bone.

FIG. 13. A 3 cm defect in the swine calvaria, 8-weeks post-injury, filled with: (A) heat-inactivated DPNCCs+HA/TCP nanoparticles; (B) HA/TCP nanoparticles only; (C) fibroblasts+HA/TCP nanoparticles.

FIG. 14. Full-thickness 3 cm critical size defect untreated (A) or loaded with HA/TCP nanoparticles and DPNCCs.

FIG. 15. A 3 cm defect in the swine calvaria, 8-weeks post-injury, filled with: (A) HA/TCP 3D-printed scaffold+DPNCCs; (B) HA/TCP scaffold only; (C) DPNCCs+HA/TCP nanoparticles; (D) HA/TCP nanoparticles only (no cells).

FIG. 21. The computer aided design of scaffold with different geometric structures. (A) mesh, (B) micro lattice structure, and (C) biomimic bone scaffold.

FIG. 23. Macro-scale cranial defect scaffold fabrication using rotary MIP based Stereolithography.

DETAILED DESCRIPTION OF ILLUSTRATIVE EMBODIMENTS

Figure 1:
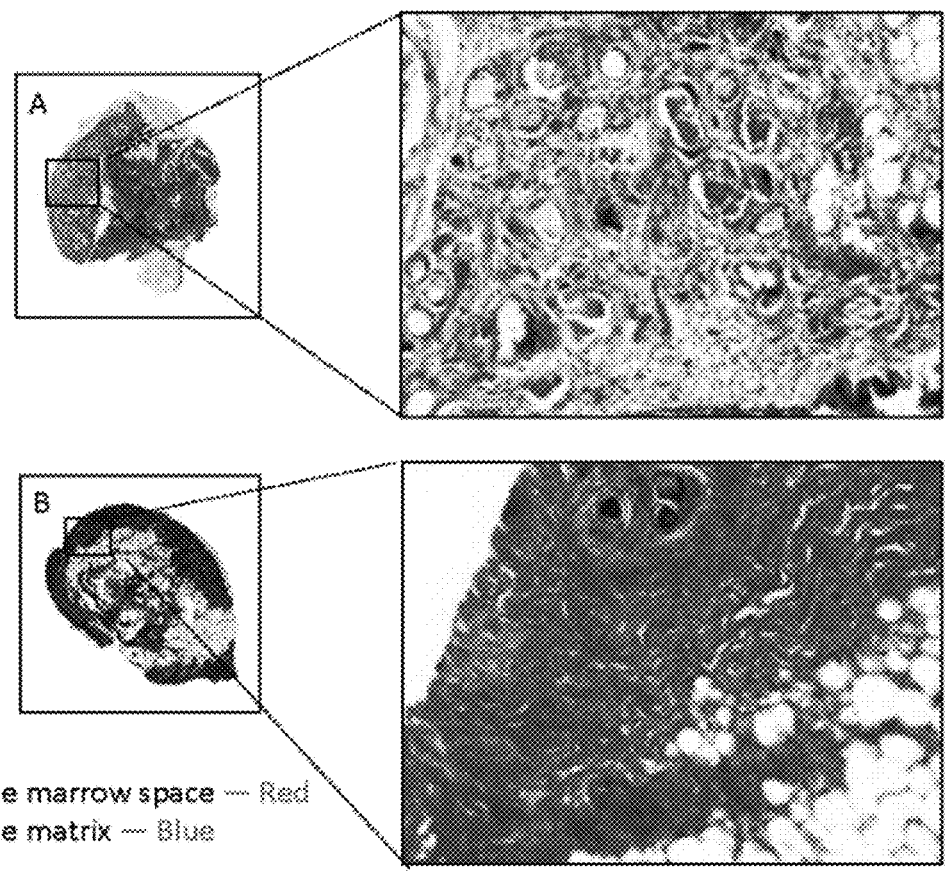
FIG. 1. Different ratios of CNCCs and BMMSCs produce bone with varying bone matrix and bone marrow space. Gomori trichrome staining of bone produced three months after implantation of CNCCs and BMMSCs at ratios of 9:1 and 1:9 ($2\times10^6$ total cells) under the skin of immunocompromised mice.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

The following acronyms are used in this disclosure.
3D: Three-Dimensional
AA: Acrylic Acid
AM: Additive Manufacturing
AMSCs: Adipose Tissue Derived Mesenchymal Stem Cells
BJ: Binder Jetting
BMMSC: Bone Marrow Tissue Derived Mesenchymal Stem Cells
BMP: Bone Morphogenetic Protein
BMP2: Bone morphogenetic protein 2
CNCC: Cranial Tissue Derived Neural Crest Cells
CAD: Computer-Aided Design
CT-MSC: Craniofacial Tissue Derived Mesenchymal Stem Cell
CSD: Critical Size Defect
CT scan: Computed Tomography Scan
DBR-SC: Dense Bone Regenerating Stem Cell
DLP: Digital Light Processing
DMD: Digital Micro-Mirror device
DPBS: Dulbecco's Phosphate-Buffered Saline
DPNCCs: Dental Pulp Tissue Derived Neural Crest Cells
DPSCs: Dental Pulp Stem Cells
DFSCs: Dental Follicle Stem Cells
EBM: Electronic Beam Melting FDM: Fused Deposition Modeling
FGF: Fibroblast Growth Factors
GelMA or GELMA: Gelatin Methacryloyl
GMSC: Gingiva-Derived Mesenchymal Stem Cell
HA/TCP: Hydroxyapatite/Tricalcium Phosphate
HA: Hydroxyapatite
HMBS: 2-Hydroxy-4-methoxy-benzophenon-5-sulfonic acid
IGF: Insulin-Growth Factor
IHH: Indian Hedgehog
LOM: Laminated Object Manufacturing
MA: Methyl Acrylate
min: minute
mins: minutes
MJ: Material Jetting
mm: millimeter
MSC: Mesenchymal Stem Cell
MIP-SL: Mask-Image-Projection-based Stereolithography
NELL-1: NEL-like protein 1
OESC: Oral Epithelial Progenitor/Stem cell
OPG: Osteoprotegerin
PBS: Phosphate Buffered Saline
PCL: Polycaprolactone
PCLDA or PCL-DA: Polycaprolactone Dimethacrylate
PEGDA: Polyethylene Glycol Diacrylate
PEDGE: Poly (ethylene glycol) Diacrylate
PDGF: Platelet Derived Growth Factor
PDLSC: Periodontal Ligament Stem Cell
Phenamil: Phenamil methanesulfonate salt
PSC: Periosteum-derived Stem Cell
s: second
SBR-SC: Spongy Bone Regenerating Stem Cells
SCAP: Stem Cell from Apical Papilla
SGSC: Salivary Gland-derived Stem Cells
SHED: Stem Cell from Human Exfoliated Deciduous Teeth
SLS: Selective Laser Sintering
SMSC: Gli1+ cell isolated from a suture mesenchyme (Suture Derived Stem Cell)
Smurf1: Smad ubiquitination regulatory factor-1
SLA: Stereolithography
TCP: Tricalcium Phosphate
TEMPO: 2,2,6,6-tetramethylpiperidine 1-oxyl
TGFβ: transforming growth factor β
TGPC: Tooth Germ Progenitor Cell
VEGF: Vascular Endothelial Growth Factor
WC: Wax Casting
Wt %: weight % or weight percent
μm: micrometer This invention relates to a bone regeneration product comprising at least one stem cell and at least one scaffold. This invention further relates to a bone regeneration product comprising at least one stem cell and at least one scaffold; wherein the scaffold comprises any scaffold suitable for carrying the at least one stem cell. This invention further relates to a bone regeneration product comprising at least one stem cell and at least one scaffold; wherein the scaffold comprises any 3D-printed scaffold suitable for carrying the at least one stem cell. This invention relates to a bone regeneration product comprising a stem cell formulation. The stem cells suitable for this invention may comprise stem cells suitable for a dense bone regeneration, stem cells suitable for a spongy bone regeneration, or a combination thereof. The bone regeneration product may further comprise a growth factor. This invention also relates to a bone regeneration method. This invention also relates to a treatment of any bone that has a critical size defect. This invention also relates to a scaffold. This invention further relates to a 3D printed scaffold. This invention also relates to a scaffold comprising hydroxyapatite (HA) and tricalcium phosphate (TCP). This invention also relates to a scaffold comprising hydroxyapatite (HA), tricalcium phosphate (TCP), and a polymer. This invention also relates to a scaffold comprising a polymer. The polymer of this invention may be prepared by using photocurable polymers and/or monomers. The scaffold of this invention may comprise a growth factor. The scaffold of this invention may comprise a growth factor and a small molecule. The small molecule may be a Smurf1 inhibitor.

This invention relates to a bone regeneration product comprising at least one stem cell. The at least one stem cell may be any stem cell. Examples of stem cells may be embryonic stem cells, fetal stem cells, adult stem cells, amniotic stem cells, cord blood stem cells, induced pluripotent stem cells, cranial neural crest cells, or any combination thereof.

In this disclosure, stem cells may be prepared by a variety of known approaches. All these stem cells are within the scope of this disclosure. For example, stem cells obtained at different stages of their preparation, e.g. from obtaining a tissue that contain them, to their isolation from the tissue, to their expansion from their isolated forms, may be incorporated into the bone regeneration product. For example, the stem cells of this disclosure may be isolated from a tissue (isolated stem cells), or may be first isolated and then expanded form a tissue (expanded stem cells), or may be present within a tissue used without any isolation and/or expansion, or may be any combination of these type of stem cells. The stem cells depending of the stages of their preparation may be more than 0.1% pure, or more than 1% pure, or more than 10% pure, or more than 20% pure, or more than 30% pure, or more than 40% pure, or more than 50% pure, or more than 60% pure, or more than 70% pure, or more than 80% pure, or more than 90% pure, or more than 95% pure, or substantially pure. All these types of stem cells are within the scope of this disclosure and collectively referred as "stem cells" herein.

For example, the stem cells may comprise mesenchymal stem cells (MSCs). Examples of mesenchymal stem cells may comprise bone marrow-derived mesenchymal cells (BMMSCs), adipose tissue-derived stem cells (AMSCs), dental pulp stem cells (DPSCs), stem cells from human exfoliated deciduous teeth (SHED), periodontal ligament stem cells (PDLSCs), dental follicle stem cells (DFSCs), tooth germ progenitor cells (TGPCs), stem cells from the apical papilla (SCAPs), oral epithelial progenitor/stem cells (OESCs), gingiva-derived mesenchymal stem cells (GMSCs), periosteum-derived stem cells (PSCs), salivary gland-derived stem cells (SGSCs), Gli1+ cells isolated from a suture mesenchyme (suture derived mesenchymal cells, SMSCs), induced pluripotent stem cells, and a combination thereof.

For in detail disclosure of such stem cells, tissues suitable for their harvest, methods of their isolation from such tissues, their expansion, and methods of administration of such stem cells for a treatment, see, for example, Egusa et al. "Stem Cells in Dentistry—Part I: Stem Cell Sources" J. Prosthodontic Res. (212) v56, p151-165; Shi et al. "A composition of stem cells having highly expressed Fas ligand," WO2015038665A1; Atsuta et al. "Mesenchymal stem cells inhibit multiple myeloma cells via the Fas/Fas ligand pathway" Stem Cell Research & Therapy, 2013, 4:111; Le et al. "Gingiva Derived Stem Cell and Its Application in Immunomodulation and Reconstruction", U.S. 201210128636A1; Shi et al. "A Composition of Mesenchymal Stem Cells", WO2014210037; Shi et al. "Compositions and Treatment Methods for Mesenchymal Stem Cell-Induced Immunoregulation," US20150104428 A1; Shi et al. "High Telomerase Activity Bone Marrow Mesenchymal Stem Cells, Methods of Producing the Same and Pharmaceuticals and Treatment Methods Based Thereon," US20130330300 A1; Shi et al. "Methods and Compositions for Improved Tissue Regeneration by Suppression of Interferon-Gamma and Tumor Necrosis Factor-Alpha," US20140154220 A1; Gronthos et al. "Postnatal human dental pulp stem cells (DPSCs) in vitro and in vivo" (2000) Proc. Natl. Acad. Sci. USA 97:13625-13630; Miura et al. "SHED: stem cells from human exfoliated deciduous teeth" (2003) Proc. Natl. Acad. Sci. USA 100:5807-5812; Yamaza et al. "Immunomodulatory properties of stem cells from human exfoliated deciduous teeth" (2011) Stem Cell Res. Ther. 1:5-14; Seo et al. "Investigation of multipotent postnatal stem cells from human periodontal ligament" (2004) Lancet 364:149-155; and Morsczeck et al. "Isolation of precursor cells (PCs) from human dental follicle of wisdom teeth" (2005) Matrix Biol. 24:155-65; Chung et al., "Stem Cell Property of Postmigratory Cranial Neural Crest Cells and Their Utility in Alveolar Bone Regeneration and Tooth Development" Stem Cells. 2009 April; 27(4): pages 866-877; and Zhao et al. "The suture provides a niche for mesenchymal stem cells of craniofacial bones" Nature Cell Biology, Volume 17, Number 4, April 2015, pages 386-396, and the supplementary information, methods, and any other associated references of the Zhao publication. The entire content of each of these publications is incorporated herein by reference.

Cranial neural crest cells (CNCCs) may give rise to neurons, glial cells, osteoblasts, and other cell types, faithfully mimicking the differentiation process of post-migratory CNCCs in vivo. CNCCs may be more suitable for supporting dense (i.e. compact or cortical) bone formation, as compared to, for example, bone marrow tissue derived mesenchymal stem cells (BMMSCs) and adipose tissue derived mesenchymal stem cells (AMSCs.)

Similarly, mesenchymal stem cells (MSCs) from a craniofacial tissue may also be more suitable for supporting dense bone formation. As such, craniofacial tissue derived mesenchymal stem cells (CT-MSCs) are other examples of DBR-SCs. Examples of CT-MSCs may comprise dental pulp stem cells (DPSCs), stem cells from human exfoliated deciduous teeth (SHED), periodontal ligament stem cells (PDLSCs), dental follicle stem cells (DFSCs), tooth germ progenitor cells (TGPCs), stem cells from the apical papilla (SCAPs), oral epithelial progenitor/stem cells (OESCs), gingiva-derived mesenchymal stem cells (GMSCs), periosteum-derived stem cells (PSCs), salivary gland-derived stem cells (SGSCs), Gli1+ cells from a suture mesenchyme (suture derived mesenchymal cells, SMSCs), and a combination thereof.

The stem cells that may support such dense bone regeneration is herein called "dense bone regenerating stem cells (DBR-SCs)."

BMMSCs, AMSCs or a combination thereof may be more suitable for supporting bone regeneration with extensive marrow space in a newly formed bone, as compared to, for example, CNCCs and CT-MSCs. Such bones have less dense bone structure and comprise more bone marrow. They are spongy (i.e. cancellous or trabecular) bones.

The stem cells that may support such spongy bone regeneration is herein called "spongy bone regenerating stem cells (SBR-SCs)."

In one example, the bone regeneration product may comprise a mesenchymal stem cell formulation. The mesenchymal stem cell formulation may comprise dense bone regenerating stem cells (DBR-SC), spongy bone regenerating stem cells (SBR-SC), or a mixture thereof. The DBR-SCs may comprise at least one cranial neural crest derived mesenchymal stem cell (CNCC). The SBR-SCs may comprise at least one mesenchymal stem cell that is not CNCC.

The DBR-SCs may comprise a stem cell derived from a craniofacial tissue. For example, the DBR-SCs may comprise a dental pulp stem cell, a stem cell from human exfoliated deciduous teeth, a periodontal ligament stem cell, a dental follicle stem cell, a tooth germ progenitor cell, a stem cell from the apical papilla, an oral epithelial progenitor/stem cell, a gingiva-derived mesenchymal stem cell, a suture stem cell, or a mixture thereof. For example, the DBR-SCs may comprise a dental pulp derived stem cell (DPSC).

The SBR-SCs may comprise a bone marrow derived mesenchymal stem cell (BMMSC), an adipose tissue derived mesenchymal stem cell (AMSC), or a mixture thereof. For example, the SBR-SCs may comprise a bone marrow derived mesenchymal stem cell (BMMSC).

The mesenchymal stem cell formulation may comprise a stem cell mixture. The stem cell mixture may comprise dense bone regenerating stem cells (DBR-SCs), spongy bone regenerating stem cells (SBR-SCs), or a mixture thereof.

In this disclosure, stem cell ratios, stem cell percentages, and/or stem cell amounts are based on number of stem cells. For example, the ratio of DBR-SC:SBR-SC is the ratio of the number of DBR-SCs to the number of SBR:SCs. For example, when the ratio of DBR-SC:SBR-SC is 9:1 in the stem cell mixture, the stem cell mixture is formed from 90% DBR-SCs by stem cell number and 10% SBR-SCs by stem cell number. Or, for example, when the ratio of DBR-SC:SBR-SC is 9:1 in the stem cell mixture, the stem cell mixture is formed from 90% DBR-SCs and 10% SBR-SCs.

In the stem cell mixture, a ratio of DBR-SCs to SBR-SCs (DBR-SC:SBR-SC) may be equal to or greater than 1. For example, in such DBR-SC:SBR-SC ratios, DBR-SC concentration in the stem cell mixture may be in the range of 50% to 100% (i.e. SBR-SCs may be in the range of 0% to 50%), or in the range of 51% to 100% or in the range of 60% to 100%, or in the range of 70% to 100%, or in the range of 80% to 100%, or in the range of 85% to 95%, or 90%. This bone regeneration product comprising such stem cell ratios (i.e. stem cell concentrations) may be particularly suitable for producing more bone matrix (i.e. denser bones) as compared to the bone regeneration product that may comprise a stem cell mixture with, for example, a DBR-SC:SBR-SC ratio of less than 1.

In the stem cell mixture, a ratio of DBR-SCs to SBR-SCs (DBR-SC:SBR-SC) may be equal to or less than 1. For example, in such DBR-SC:SBR-SC ratios, SBR-SC concentration in the stem cell mixture may be in the range of 50% to 100% (i.e. DBR-SCs may be in the range of 0% to 50%), or in the range of 51% to 100%, or in the range of 60% to 100%, or in the range of 70% to 100%, or in the range of 80% to 100%, or in the range of 85% to 95%, or 90%. This bone regeneration product comprising such stem cell ratios (i.e. ratios) may be particularly suitable for producing bone matrix with less density (i.e. spongy bones) as compared to the bone regeneration product that may comprises a stem cell mixture with, for example, a DBR-SC:SBR-SC ratio of greater than 1.

The DBR-SCs may comprise CNCCs. The SBR-SCs may comprise BMMSCs.

In this disclosure, the bone regeneration product may further comprise a growth factor. The stem cells mixture may further comprise a growth factor. The scaffold may further comprise a growth factor.

In this disclosure, the growth factor may be any growth factor. Examples of the growth factor are bone morphogenic protein (BMP); Indian hedgehog (IHH); transforming growth factor β (TGFβ); bone morphogenetic proteins (BMPs) for example BMP-2, 4, 6 and 9; fibroblast growth factors (FGFs) like FGF-1 and 2; an epithelial cell growth factor (EGF); Wnt ligands and β-catenin; insulin-growth factors (IGFs) like IGF-1 and IGF-2; Collagen-1; Runx2; Osteopontin; Osterix; vascular endothelial growth factor (VEGF); platelet derived growth factor (PDGF); osteoprotegerin (OPG); NEL-like protein 1 (NELL-1); or any combination thereof. For in detail disclosure of such growth factors, see, for example, Devescovi, V. et al. "Growth factors in bone repair" Chir Organi Mov 92, 161, 2008; James A. W. "Review of Signaling Pathways Governing MSC Osteogenic and Adipogenic Differentiation" Scientifica (Cairo) 2013; 2013: 684736; Carofino B. C. et al. "Gene therapy applications for fracture healing" J Bone Joint Surg Am, 90 (Suppl 1) (2008), pp. 99-110; Javed A. et al. "Genetic and transcriptional control of bone formation" Oral Maxillofac Surg Clin North Am. 2010; 22: 283-93; Chen G. et al. "TGF-β and BMP signaling in osteoblast differentiation and bone formation" Int. J. Biol. Sci. 2012; 8:272-288. doi: 10.7150/ijbs.2929; Ornitz, D. M. et al. "FGF signaling pathways in endochondral and intramembranous bone development and human genetic disease. Genes Dev. 16, 1446-1465 (2002); Krishnan V. et al. "Regulation of bone mass by Wnt signaling" J. Clin. Invest. 116 1202-1209 (2006); and Boyce B. F. et al. Functions of RANKURANK/OPG in bone modeling and remodeling" Arch Biochem Biophys. 473(2):139-146 (2008). The entire content of each of these publications is incorporated herein by reference.

The bone regeneration product may further comprise a Smad ubiquitination regulatory factor-1 (Smurf1) inhibitors, which may further improve the healing of the CSD. This improvement in the healing may be achieved by positively regulating bone morphogenetic protein (BMP) pathway by preventing ubiquitination of certain signal components for degradation. As such, any inhibitor that can positively regulating bone morphogenetic protein (BMP) pathway is within the scope of this disclosure.

Examples of Smurf1 inhibitors may be A01, A02, A03, A04, A05, A06, A07, A08, A09, A10, A11, A14, A15, A17, A18, A25, A54, A63, A75, phenamil, the like, or a combination thereof. Examples of Smurf1 may also be A01, A17, phenamil, or a combination thereof.

For further information on A01, A02, A03, A04, A05, A06, A07, A08, A09, A10, A11, A14, A15, A17, A18, A25, A54, A63, A75, their chemical structures and their biological activity, see Cao et al. "Selective Small Molecule Compounds Increase BMP-2 Responsiveness by Inhibiting Smurf1-mediated Smad1/5 Degradation" Nature, Scientific Reports, 4: 4965|DOI: 10.1038/srep04965, May 14, 2014. The entire contents of this publication and its supplementary information are incorporated herein in their entirety.

An example of Smurf1 inhibitor may be phenamil (Phenamil methanesulfonate salt, or 3,5-Diamino-6-chloro-N-[imino(phenylamino)methyl]pyrazinecarboxamide methanesulfonate salt.) This small molecule, phenamil may act cooperatively with BMPs to induce the expression of BMP target genes and further promote bone regeneration.

The bone regeneration product may further comprise a scaffold. Or, the bone regeneration product may comprise a scaffold. The bone regeneration product comprising a scaffold may be used in a treatment without necessitating any stem cell.

The scaffold may be any scaffold. The scaffold may comprise a porous, three-dimensional (3D) network of interconnected void spaces. The scaffold may be any scaffold suitable to incorporate the stem cells and/or growth factors disclosed in this invention into its structure. The scaffold may be any scaffold that may incorporate the stem cells and/or growth factors disclosed in this invention into its structure to aid in forming a direct contact and/or an indirect contact of these stem cells and/or growth factors with a tissue (e.g. bone) for the regeneration of this tissue (e.g. bone). The scaffold may incorporate the stem cells and/or growth factors disclosed in this invention into its structure in any form, for example, by carrying, by supporting, by adsorbing, by absorbing, by encapsulating, by holding, and/or by adhering to the stem cells and/or growth factors disclosed in this invention.

The scaffold may have any shape or geometry. The scaffold may have any pore size. The scaffold may have any porosity (i.e. void volume.) The scaffold may have any form. The scaffold may have any mechanical strength.

Bone defects may form in different parts of an animal or a human body. These defects may have any shape and size. Scaffolds suitable for the treatment of such defects may have shapes, volumes and sizes that can, for example, fit to or resemble the defect shape and size. Such scaffolds may also have pore volumes, pore sizes, and/or pore shapes that resemble to the bone for which the bone regeneration products that comprise such scaffolds are designed for their treatment. Such scaffolds may also have pores with pore sizes sufficiently small such that these scaffolds can contain the stem cells of this disclosure within their porous structures and allow the bone regeneration product to be implanted and the treatment can be successfully carried out. The bone regeneration products of this disclosure also need to have a mechanical strength sufficient enough to handle load bearing conditions of their implantation to a body. They also need, to have a mechanical strength sufficient enough to handle load bearing conditions of bones during motion (e.g. walking) and/or weight of the bodies.

As shown below in Examples, the scaffold's porosity, pore size, pore shape, mechanical strength, volume, and shape may be controlled within desired levels.

The scaffold may comprise any material. For example, the scaffold may comprise a non-resorbable material, resorbable material, or a mixture thereof. The resorbable material may be resorbed by the body of a patient, and eventually replaced with healthy tissue. A "resorbable" material may comprise, for example, a biocompatible, bioabsorbable, biodegradable polymer, any similar material, or a mixture thereof.

The biocompatible material is a material that may be accepted by and to function of a body of a patient without causing a significant foreign body response (such as, for example, an immune, inflammatory, thrombogenic, or like response), and/or is a material that may not be clinically contraindicated for administration into a tissue or organ.

The biodegradable material may comprise a material that is absorbable or degradable when administered in vivo and/or under in vitro conditions. Biodegradation may occur through the action of biological agents, either directly or indirectly.

The scaffold may comprise a solid, a liquid, or a mixture thereof. For example, the scaffold may be a paste. For example, the scaffold may comprise a paste comprising a mixture of hydroxyapatite and tricalcium phosphate (HA/TCP). This scaffold, for example, may be prepared by mixing hydroxyapatite (HA) and tricalcium phosphate (TCP) with a formulation comprising a liquid to prepare a paste. For example, the mesenchymal stem cell formulation may comprise a liquid; and mixing of such mesenchymal stem cell formulation with hydroxyapatite (HA) and tricalcium phosphate (TCP) may form a paste. This type of scaffold is called an HA/TCP scaffold herein.

In this disclosure, a mixture comprising HA and TCP (HA/TCP) may be formed from equal amounts of HA and TCP in weight, for example 50 wt % HA and 50 wt % TCP, unless otherwise stated. However, the mixture comprising HA and TCP may have any composition, for example, varying in the range of 0 wt % HA to 100 wt % TCP. For example, an HA concentration higher than 10 wt %, higher than 20 wt %, higher than 30 wt %, higher than 40 wt %, higher than 50 wt %, higher than 60 wt %, higher than 70 wt %, higher than 80 wt %, or higher than 90 wt % is within the scope of this disclosure.

The scaffolds of this disclosure, for example, may comprise any biodegradable polymer. For example, the scaffold may comprise a synthetic polymer, naturally occurring polymer, or a mixture thereof. Examples of suitable biodegradable polymers may be polylactide (PLA), polyglycolide (PGA), poly(lactide-co-glycolide) (PLGA), poly-E-caprolactone, polydioxanone trimethylene carbonate, polyhybroxyalkonates (e.g., poly(hydroxybutyrate)), poly(ethyl glutamate), poly(DTH iminocarbony (bisphenol A iminocarbonate), poly(ortho ester), polycyanoacrylates, fibrin, casein, serum albumin, collagen, gelatin, lecithin, chitosan, alginate, poly-amino acids (such as polylysine), and a mixture thereof.

The scaffold may further comprise the growth factor of this disclosure. This growth factor may be continuously released to the surround (bone) tissue after the bone regeneration product is implanted into the bone defect site. The release rate of the growth factor may be controlled through the scaffolds' chemical composition and/or pore structure.

This scaffold may be manufactured by any technique. For example, the scaffold may be manufactured by hand, and/or by using a machine. For example, the scaffold may be manufactured by additive manufacturing and/or manufacturing. For example, the scaffold may be manufactured using a combination of more than one such manufacturing techniques.

For example, the scaffold may be manufactured by three-dimensional (3D) printing technique. Any 3D printing technique may be used to manufacture the scaffold of this invention. The 3D printing technique or the additive manufacturing (AM) may be a process for making a physical object from a three-dimensional digital model, typically by laying down many successive thin layers of a material. Such thin layers of material may be formed under computer control. Examples of the 3D printing technologies may be Stereolithography (SLA), Digital Light Processing (DLP), Fused deposition modeling (FDM), Selective Laser Sintering (SLS), Selective laser melting (SLM), Electronic Beam Melting (EBM), Laminated object manufacturing (LOM), Binder jetting (BJ), Material Jetting (MJ) or Wax Casting (WC), or a combination thereof.

The scaffold, including the 3D printed scaffold, for example, may be manufactured by using a formulation comprising polycaprolactone dimethacrylate (PCLDA), calcium phosphate, hydroxyapatite (HA), tricalcium phosphate (TCP), polyethylene glycol diacrylate (PEGDA), gelatin methacryloyl (GeIMA), or a mixture thereof.

The scaffold may comprise at least two chambers. At least one chamber of this scaffold may incorporate a mesenchymal stem cell formulation comprising a ratio of DBR-SCs to SBR-SCs (DBR-SC:SBR-SC) that is equal to or greater than 1. For example, in such DBR-SC:SBR-SC ratios, DBR-SC concentration in the stem cell mixture may be in the range of 50% to 100% (i.e. SBR-SCs may be in the range of 0% to 50%), or in the range of 51% to 100% or in the range of 60% to 100%, or in the range of 70% to 100%, or in the range of 80% to 100%, or in the range of 85% to 95%, or 90%. This bone regeneration product comprising such stem cell ratios (i.e. stem cell concentrations) may be particularly suitable for producing more bone matrix (i.e. denser bones) as compared to the bone regeneration product that may comprise a stem cell mixture with, for example, a DBR-SC:SBR-SC ratio of less than 1.

At least one chamber of this scaffold may incorporate a mesenchymal stem cell formulation comprising DBR-SCs to SBR-SCs (DBR-SC:SBR-SC) that is equal to or less than 1. For example, in such DBR-SC:SBR-SC ratios, DBR-SC concentration in the stem cell mixture may be in the range of 50% to 100% (i.e. SBR-SCs may be in the range of 0% to 50%), or in the range of 51% to 100% or in the range of 60% to 100%, or in the range of 70% to 100%, or in the range of 80% to 100%, or in the range of 85% to 95%, or 90%. This bone regeneration product comprising such stem cell ratios (i.e. stem cell concentrations) may be particularly suitable for producing more bone matrix (i.e. denser bones) as compared to the bone regeneration product that may comprise a stem cell mixture with, for example, a DBR-SC:SBR-SC ratio of less than 1.

This invention is also related to a bone regeneration method, and to the scaffold described herein for use in regenerating bone. This bone regeneration method may comprise implanting the bone regeneration product disclosed herein in or across a bone defect. This bone defect may be any bone defect. For example, the bone defect may be a bone defect of a long bone. The size of this bone defect may be any size. For example, the size of this bone defect may be a critical size. The bone defect, for example, may be formed due to a congenital bone malformation. The congenital bone defect, for example, may be a defect related to a cleft lip and/or a cleft palate. The bone defect, for example, may be formed as a result of a surgery, accident, and/or disease. This bone defect, for example, may be formed as a result surgery carried out to treat craniosynostosis.

This disclosure relates to regeneration of a bone tissue that can fill a long bone CSD using MSCs and/or 3D-printed osteoinductive scaffolds ("scaffold"). Using this innovative approach, we hope to lay the groundwork for helping patients heal successfully from long bone defects, enabling them to resume their daily life activities.

As disclosed in the examples, the scaffold alone may be insufficient for bone regrowth in a CSD. The growth factor IHH accelerates healing of femurs with CSDs, highlighting that a combination of different cells and growth factors in the scaffold may be necessary to achieve ideal healing results for long bone defects.

EXAMPLES

Example 1. Mouse CNCC and BMMSC Cultures

Four-week-old mice were euthanized according to procedures approved by the USC IACUC and their mandibles were separated, minced and digested with a solution containing 2 mg/ml collagenase type I and 4 mg/ml dispase II in PBS for 1 hour at 37° C. The long bone marrow was flushed out from the femur and tibia, spun down and resuspended. A single-cell suspension was obtained by passing the cells through a 70 μm strainer and seeded in 10-cm plate culture dishes with α-MEM supplemented with 20% FBS, 2 mM L-glutamine, 55 μM 2-mercaptoethanol, 100 U/ml penicillin and 100 μg/ml streptomycin. The culture medium was changed after an initial incubation of 48 hours.

Example 2. Subcutaneous Cell Implantation

CNCCs and BMMSCs were mixed at ratios of 9:1, 5:5 and 1:9. Then $2\times10^6$ total cells were implanted under the skin of immunocompromised mice. Mice were euthanized and cells were harvested three months after implantation, fixed in 4% PFA, decalcified and sectioned for histology.

Example 3. Scaffold Degradation and Cytotoxicity

Polycaprolactone (PCL)-based 3D-printed scaffolds were implanted subcutaneously in immunocompromised mice and collected at different time points to test the degradation profiles by measuring their dry weight.

To test for potential cytotoxicity of the PCL scaffolds, NIH3T3 cells were plated in 96-well plates at a density of $1\times10^4$ cells/well. After 24 hours of incubation to allow cell attachment, PCL scaffolds were co-cultured in DMEM medium with 10% of FBS for 72 hours. MTT cell assays were performed to test cell viability following the manufacturer's instructions (Abcam).

Example 4. Long Bone Critical-Sized Defect Model

Mice were placed in ventral recumbence with the left hind limb in extension. An anterolateral approach was used to expose the anterior surface of the femur. Briefly, after a lateral longitudinal cutaneous incision along the femur extending from the hip joint to the stifle joint was made, the fascia lata was incised to expose the full length of the femur, preserving the sciatic nerve caudally and the articular capsule distally. An anterior polyether ether ketone (PEEK) microlocking plate (MouseFix Plate; RISystem AG, Davos, Switzerland) was applied on the anterior femoral side. Next, four holes were drilled using a 0.3-mm drill bit (Drill Bit 0.30 mm; RISystem AG, Davos, Switzerland) and four self-tapping locking screws (MouseFix Screw 2 mm; RISystem AG, Davos, Switzerland) were inserted through the most proximal and most distal holes of the plate and locked to secure the plate. Gigli saws (0.22 mm; RISystem AG, Davos, Switzerland) were then inserted, one each in the two slots of the jig (Drill and Saw Guide; RISystem AG, Davos, Switzerland), and a 2-mm-long mid-diaphyseal femoral ostectomy was subsequently performed. The defect was either left empty or filled with different combinations of the PCL scaffolds and cells indicated to test long bone regenerative ability.

Example 5. Radiographic Analysis, Sample Collection and Histology

Radiographs were taken every two weeks to evaluate the bone union process until 3 months after the surgery. Immediately after euthanasia at 3 months post-surgery, all left femoral bones were excised. All overlaying muscle tissue was carefully removed. The femoral bones were fixed in 4% paraformaldehyde (pH 7.4) overnight. The plate and screws were removed and the samples were then decalcified in 10% EDTA (pH 7.4) for four weeks. Samples were passed through serial concentrations of ethanol for embedding in paraffin wax and sectioned at 7 μm using a microtome (Leica). Deparaffinized sections were stained with Hematoxylin and Eosin using standard procedures for general morphology.

Example 6. Osteogenic Differentiation Analysis

Dental pulp mesenchymal stem cells (DPSCs) were harvested from the apical region of the dental pulp mesenchyme from the mandibular incisor of postnatal one-month-old mice. After two passages, DPSCs were cultured either alone or with hedgehog inhibitor (GDC0449) or Indian hedgehog (IHH) recombinant protein, followed by Alizarin red staining to examine osteogenic differentiation.

Example 7. Release Profile of Scaffolds Impregnated with IHH Growth Factor

PCL-based scaffolds with or without IHH growth factor were submerged in 50 μl of cell culture medium and incubated at 37° C. The medium was collected and replaced every day. An enzyme-linked immunosorbent assay (ELISA) was used to quantify the growth factor released in the medium according to the manufacturer's instructions (LifeSpan BioScience).

Example 8. Statistical Analysis

Each experimental condition was performed on at least three samples unless otherwise stated. ANOVA (single factor) was applied for statistical analysis. $P<0.05$ was considered statistically significant.

Example 9. CNCC:BMMSC Ratio and Scaffold Material for Bone Regeneration

Figure 2:
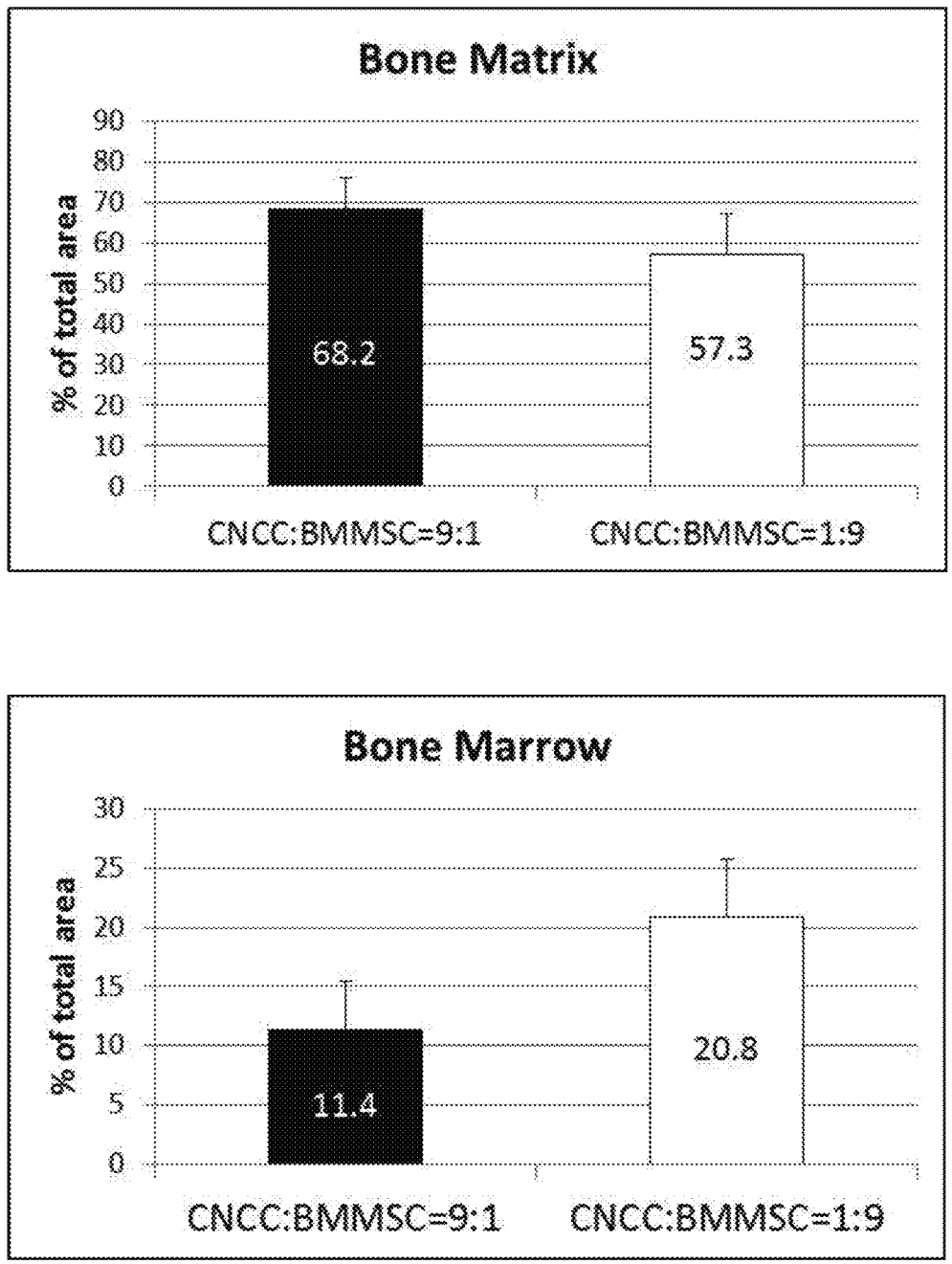
FIG. 2. Quantification of bone matrix and bone marrow produced in subcutaneous implants. Quantification was done using ImageJ. *, p<0.05.

In order to achieve long bone regeneration with enhanced cortical bone matrix formation, we tested different ratios of cranial neural crest-derived stem cells (CNCCs) and bone marrow-derived stem cells (BMMSCs) implanted subcutaneously in immunocompromised mice and analyzed the ratio of bone matrix to bone marrow in the newly formed bone (FIG. 1). Our results indicated that transplants with 90% CNCCs (i.e. CNCC:BMMSC ratio is 9) produced approximately 68% bone matrix and 11.4% bone marrow, whereas transplants with 90% BMMSCs (i.e. BMMSC:CNCC ratio is 9) produced 57.3% bone matrix and 20% bone marrow (FIG. 2). Thus, CNCCs promote denser bone matrix formation as compared to BMMSCs.

Example 10. Test of the Scaffold Material for Bone Regeneration

The choice of scaffold material for bone regeneration is challenging, especially for critical-sized defects. Many factors may affect the selection of scaffold materials, including biocompatibility, biodegradability, microstructure, and mechanical load-bearing capability. 3D printing offers great advantages in scaffold manufacturing compared to traditional molding, such as precision in design, the ability to generate complex microstructures, and time efficiency.

Polycaprolactone (PCL) is a biodegradable polyester that has been widely used in many biomedical applications including bone tissue regeneration. PCL is approved by the U.S. Food and Drug Administration for applications in the human body as a drug delivery device, suture material (sold under the brand name Monocryl or generically), or adhesion barrier. After successful printing of 3D scaffolds from PCL, we first tested the biocompatibility of the scaffolds in vitro. After 72 hours of incubation of the scaffolds with NIH3T3 cells, the number of viable cells was indistinguishable in the control and treatment groups (FIG. 3C). Next we tested the degradation profile of the scaffolds when implanted subcutaneously in immune deficient mice. After 60 days of implantation, the scaffold degraded about 40% by weight (FIG. 3D).

Example 11. Bone Regeneration to Repair CSDs in the Long Bone

Many animal models have been used for studies of bone regeneration in CSDs, including mice, rats, rabbits, dogs, sheep, and pigs. Mice have several advantages compared to other animals, such as reasonable experiment time, availability of immunocompromised (nude) mice, and the ability to utilize transgenic mice to research specific gene functions during bone formation.

Mouse calvarial bones have been widely used in bone-related research, but many other factors may affect the regeneration and homeostasis of these bones, such as the periosteum, dura mater and sutures. Therefore, the femur is a more desirable model, particularly for research related to the healing of fractures in load-bearing bones. The defect size, load-bearing property, and manner of ossification of the mouse hind limb are quite similar to those of the lower extremity in humans. However, the small size of mice makes surgery on the femur difficult. Recently, we have developed a surgical technique for creating a non-union femoral defect in live nude mice (FIG. 4). These mice can support bone regeneration for three to four months following the initial surgery and can therefore serve as a model for stem cell-mediated bone regeneration.

We fabricated PCL-based scaffolds with good elasticity and tenacity. Initially, we implanted this scaffold in a femoral defect to test biodegradability (FIG. 5). Three months after the surgery, the mice were able to walk well. In the control group, PCL-based scaffolds alone did not support bone regeneration, and we detected no bone regrowth after implantation of the scaffold alone.

Figure 7:
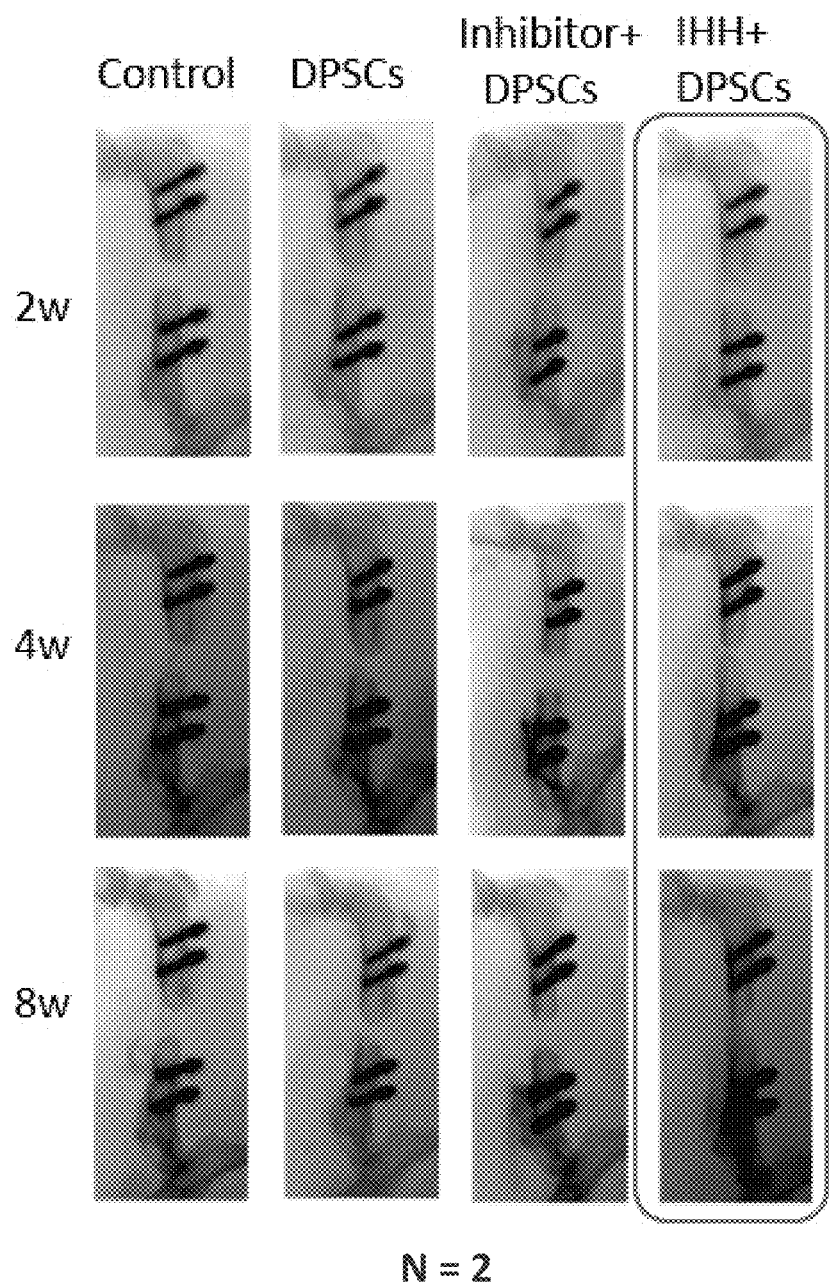
FIG. 7. IHH accelerates the healing of CSDs in the femur. X-ray images taken 2, 4 and 8 weeks (w) after implantation of scaffold alone (control) or HA/TCP containing DPSCs, DPSCs and GDC0449 inhibitor, or DPSCs and IHH in femoral CSDs.
Figure 8:
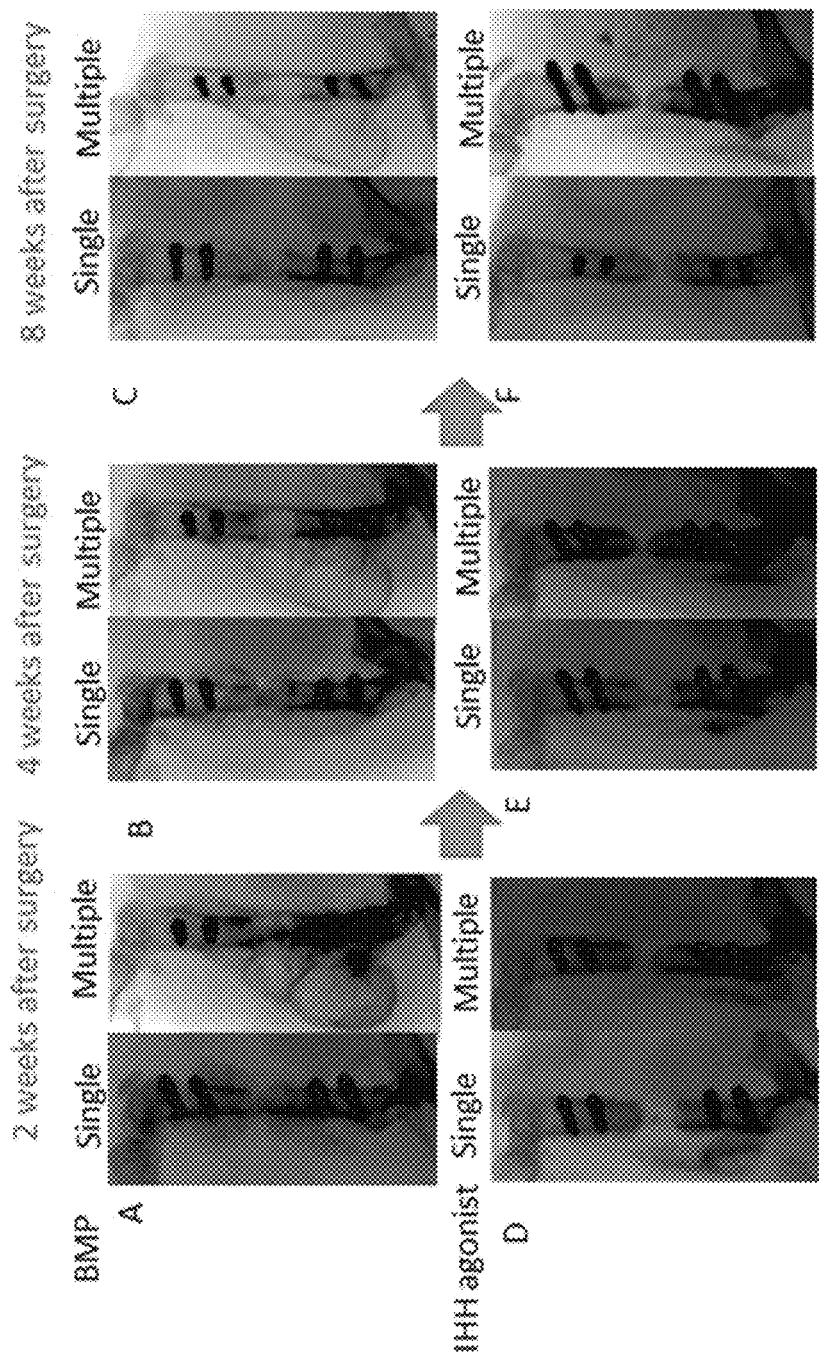
FIG. 8. Multiple doses of IHH and BMP accelerate the healing of CSDs in the femur. X-ray images taken 2, 4 and 8 weeks after either single or multiple doses of BMP2 or IHH agonist in femoral CSDs.

In addition, we conducted studies to investigate the role of growth factors during bone regeneration. We found that Indian hedgehog (IHH) not only accelerates osteogenesis activity of DPSCs in vitro (FIG. 6), but also helps femoral CSDs heal in vivo (FIG. 7). To facilitate the healing of a femoral CSD, we treated mice with one dose of IHH on the same day as the surgery. We observed enhanced bone regeneration in the treatment group compared to controls that did not receive IHH. Four weeks after surgery, the mice treated with IHH had significant outgrowths of new bone in the anteroposterior (AP) direction (FIG. 7). However, after 8 weeks, the CSDs of mice treated with IHH had not fully healed, as the new bone formation slowed down after the initial 4 weeks. We reasoned that this might be due to the single dose of IHH, which may not be sufficient to support continued bone regeneration for an extended period of time. Therefore, we tested the effect of multiple doses of various growth factors. The growth factors were injected in the defect site every 3 days for the first two weeks after surgery. Compared to the single-dose treatment, the multiple doses did indeed improve the bone regeneration over the 8-week period (FIG. 8). In the group treated with multiple doses of BMP, union of the cortical bone at the defect site was detectable radiographically. BMP has a stronger bone regenerative ability than IHH agonist; however, we did notice some ectopic bone formation surrounding the injury site. This may be due to inaccuracy in the growth factor injection.

Figure 9:
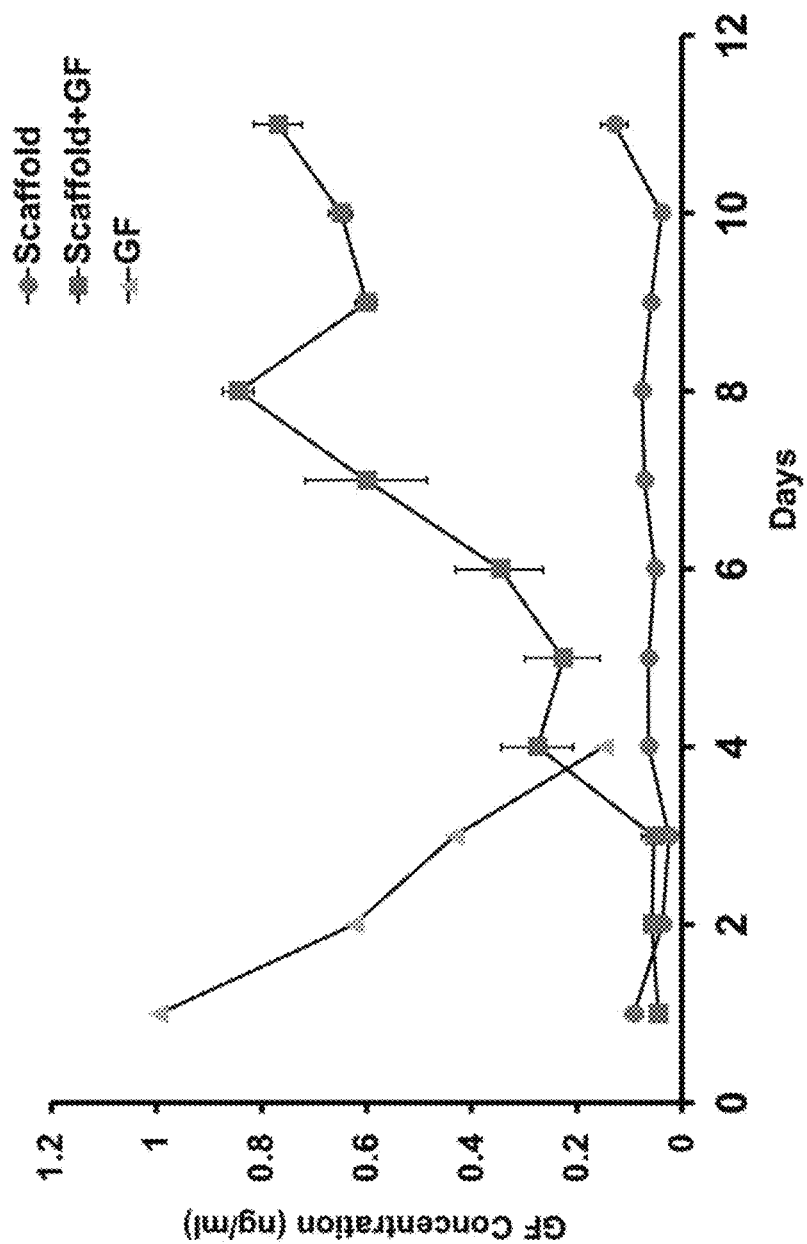
FIG. 9. IHH is stably released from scaffolds impregnated with growth factor. ELISA quantification of growth factor (GF) concentration released in the medium after 1-12 days from scaffolds alone, scaffolds impregnated with growth factor, or growth factor alone.
Figure 10:
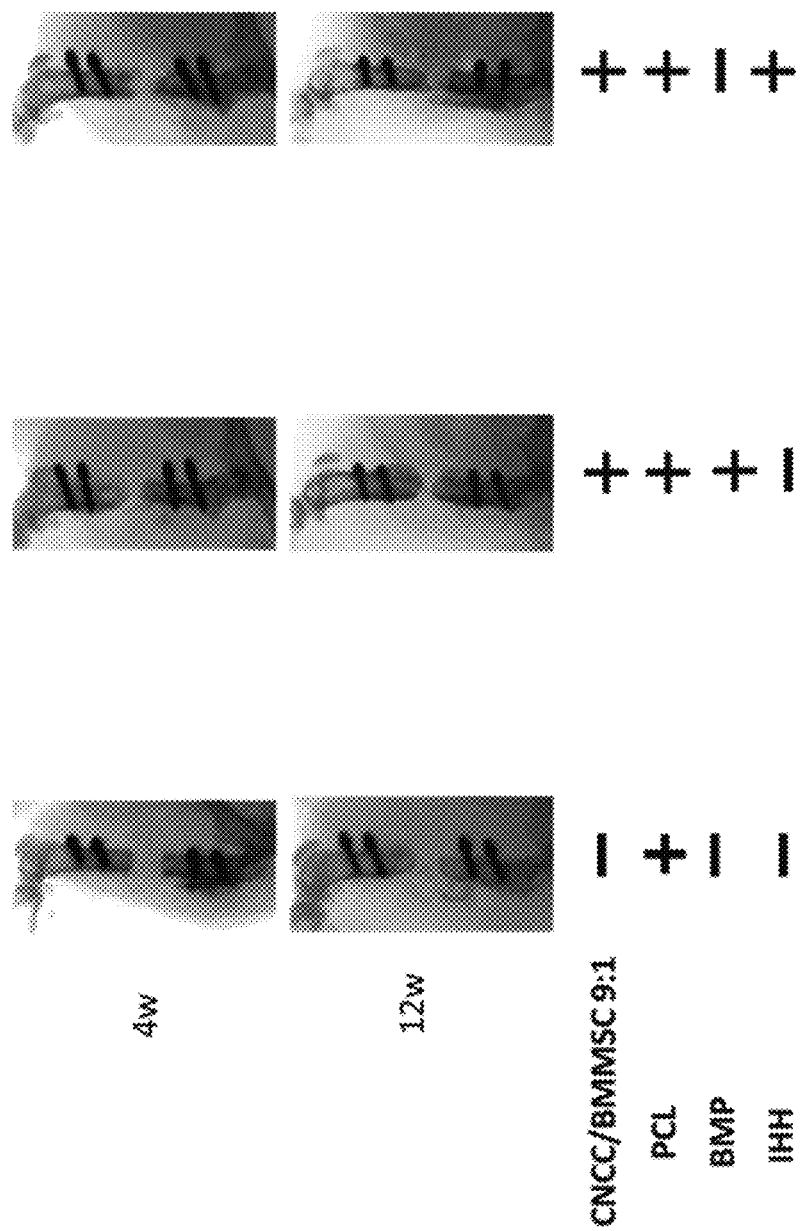
FIG. 10. Scaffolds impregnated with IHH and BMP accelerate the healing of CSDs in the femur. X-ray images were taken 4 weeks after creation of femoral CSDs and implantation of scaffolds.

To improve the growth factor delivery, thus potentially minimizing ectopic bone formation and simplifying the treatment process, we incorporated growth factors in the PCL-based scaffolds during the 3D printing process. As the scaffolds degrade, the growth factors are released into the defect site continuously resulting in sustained delivery of growth factors. We first tested the release profile of the scaffold in vitro, and we found that the growth factor can be first detected on day 4, after which it is stably released for 11 days; when introduced directly into the culture medium alone, the growth factor was fully degraded after 4 days (FIG. 9). Next, we tested the scaffolds in the mouse CSD model. After 4 weeks, bone formation in treatment groups was significantly accelerated compared to controls without any growth factor in the scaffold (FIG. 10). However, after 12 weeks, bone union was not observed.

Figure 11:
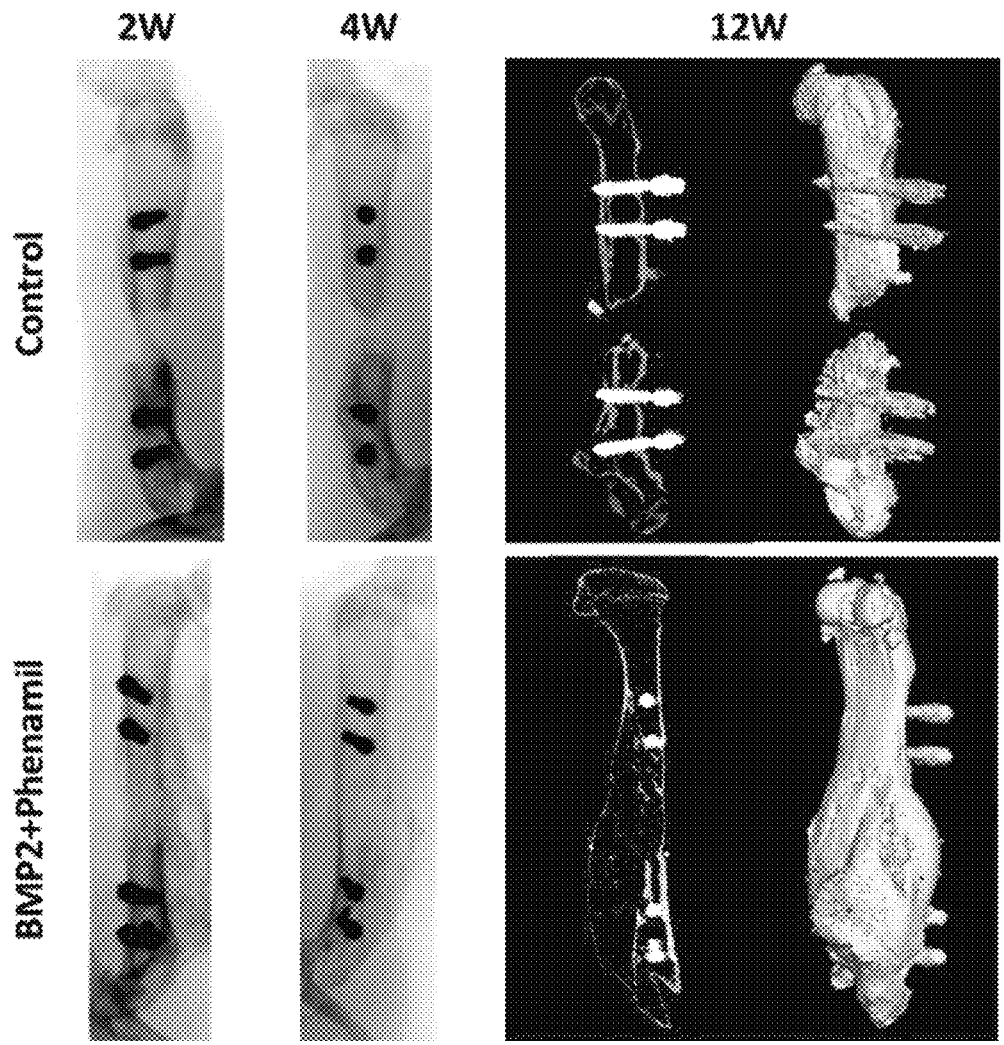
FIG. 11. Cortical bone union was achieved after BMP2 and phenamil treatment in mouse CSDs. X-ray images were taken at 2, 4 and 12 weeks (W) after femoral CSDs. MicroCT images were taken after sample harvest at 12 weeks after surgery.
Figure 16:
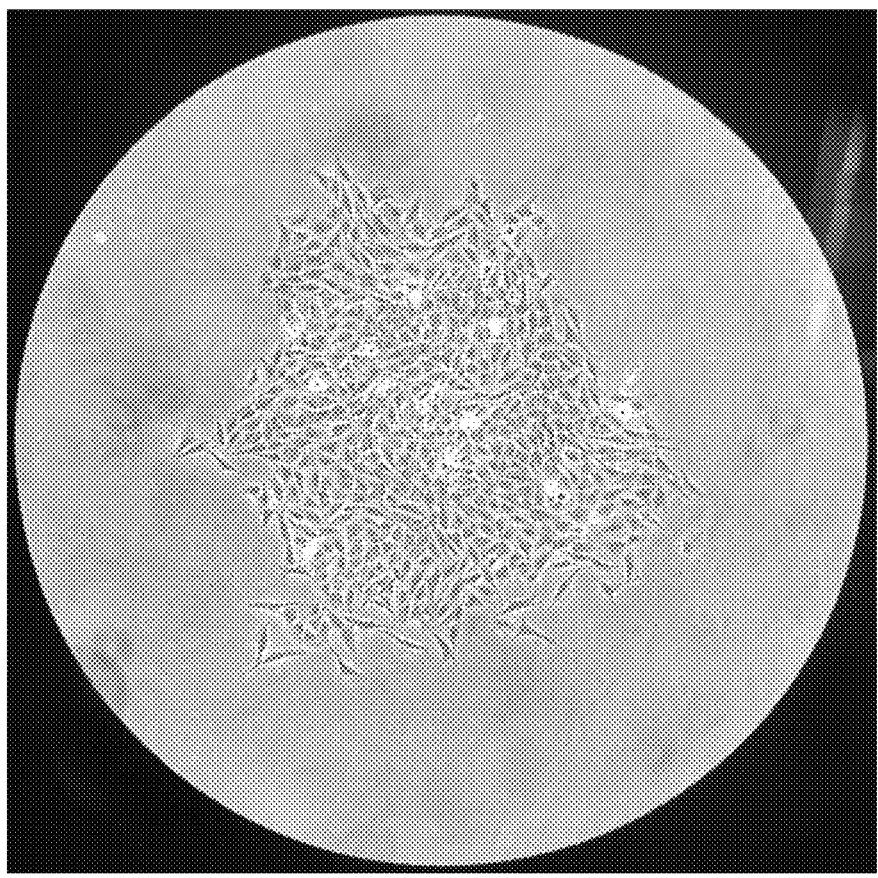
FIG. 16. A single-cell colony of dental pulp neural crest mesenchymal stem cells.
Figure 17:
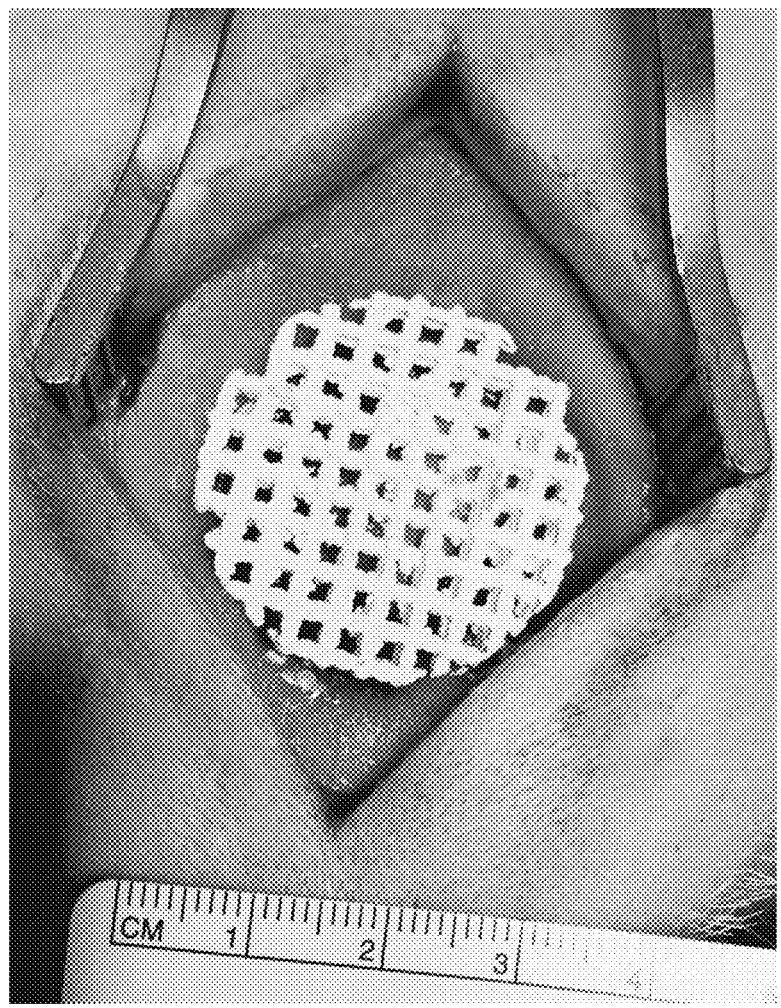
FIG. 17. 3D-printed HA/TCP scaffold without cells loaded into a 3 cm critical size defect in the swine calvaria.

To further improve the healing of the CSDs, we added phenamil, a small molecule that acts cooperatively with BMPs to induce the expression of BMP target genes and promote bone regeneration, together with BMP2. After 4 weeks, we detected callus formation in the defect site, and bone outgrowth in the AP direction was significantly improved. Eight weeks after the surgery, cortical bone union was achieved (FIG. 11).

The speed and completion of the healing process are not the only important outcomes to measure in long bone CSD repair. Another important criterion to assess is the elasticity of the new bone. Bone that is too hard will fracture too easily, but bone that is too soft will be unable to support the body. Proper elasticity can help restore the motor function of limbs. Thus, we also want to test elasticity using the three-point bending method (FIG. 12).

Example 12. Animal Model for Calvarial Bone Regeneration

Yorkshire farm pigs at 7-8 weeks of age (weighing 15-20 kg) were used to investigate stem cell-mediated calvarial bone regeneration. All animal procedures were performed in accordance with federal regulations and with approval from the Institutional Animal Care and Use Committee (IACUC) at the University of Southern California.

Example 13. Harvesting of Swine Dental Pulp Cells

Each pig was anesthetized by veterinary staff and placed on its stomach. The inside of its mouth was wiped sequentially with a germicide and ethanol before tooth extraction to help prevent infection. The right incisor was extracted and the remaining gap was closed with discontinuous, absorbable sutures. DPNCCs were harvested from the incisor and expanded in cell culture. DPNCCs were cultured for 14 days while the pig healed.

Example 14. Culture of Swine Dental Pulp Cells

After extraction of the incisor, the outside of the tooth was bleached to eliminate oral microbes. The tooth was cut open and the dental pulp was removed. The dental pulp was then finely chopped, digested with dispase II at 37° C. for 1.5 hours, and strained for single cells using a 70 µm cell strainer. Cells were originally plated at $1 \times 10^6$ per 15 cm dish. Cells were incubated at 37° C. and 5% $CO_2$.

Once cells reached ~70% subconfluence, they were detached from the plates with TrypIE and passaged. With each passage, $1 \times 10^6$ cells were plated into 15 cm dishes. This process was repeated 2-3 times over 14 days before transplantation into the calvarial defect.

Cells were counted using a BioRad TC20 Automated Cell Counter. 10 uL of suspended cells were loaded into the cartridge. For each animal, 3-4$\times 10^6$ cells were transplanted into the defect site via HA/TCP particles or 3D-printed scaffold.

With the remaining cells not used for transplantation, the ability of the DPNCCs to differentiate into adipocytes, chondrocytes, and osteoblasts was verified. DPNCC colonies were grown in adipogenic, chondrogenic, and osteogenic culture media. Adipogenic differentiation was evaluated using Oil Red O staining for lipid droplets. Chondrogenic differentiation was evaluated using Alcian blue staining for cartilage formation. Osteogenic differentiation was evaluated using Alizarin red staining for bone formation.

Example 15. Preparation of Dental Pulp Cells for Transplantation

Cells were washed with PBS and dissociated from the culture dish. After centrifuging and removing the supernatant, the cell pellet was resuspended in 3 mL culture media and immediately placed on ice. During surgery, the 3 mL cell suspension was transplanted into the 3D-printed scaffold positioned within the critical size defect. Sterile HA/TCP nanoparticles were obtained from Sigma-Aldrich. For surgeries using the 3D-printed scaffold loaded in the CSD, cells were resuspended in 0.5-1 mL culture media.

Example 16. Bone Marrow Collection in Swine

After anesthesia by veterinary staff, the animal was placed in lateral recumbency. The tibia was shaved and cleaned three times sequentially with germicidal scrub and 70% ethanol. A bone punch was used on the medial aspect of the proximal tibia, where the bone is not covered by muscle. This was confirmed by palpating the area. Once the needle penetrated the bone cortex, 4 mL bone marrow was collected using a syringe and immediately placed on ice. Bone marrow cells from this collection were placed directly into the 3D-printed HA/TCP scaffold to fill the calvarial critical size defect.

Example 17. Creating the Critical-Sized Defect in Swine

Each pig was anesthetized by the veterinary staff and placed on its stomach. The cranial surface was shaved and then cleaned sequentially with Betadine and 70% ethanol. A scalpel was used to make a 7-8 cm incision in the skin, about 1 cm left of the midline. A periosteal elevator was used to lift the periosteum from the calvarial bone. Once the underlying bone was exposed and surrounding skin and periosteum were retracted, the critical-size defect of 3-4 cm in diameter was measured and marked on the bone. An oscillating saw was used to cut into the bone. When approaching the most proximal portion of the bone, a hammer and chisel were used to create the full-thickness defect so as not to damage the dura or brain below. Once the critical-sized defect was created, HA/TCP nanoparticles were mixed with cells and loaded into the defect site. For experimental groups using the 3D-printed scaffold, the scaffold was loaded into the CSD first, then cells were injected into the holes of the scaffold using a syringe. Control animal CSDs were not filled with HA/TCP nor cells. The incision was then closed in layers, with the periosteum closed first and the skin sutured second. The defect was allowed to heal over 8 weeks.

Example 18. Collection and Histology of Swine Calvaria

The animal was first anesthetized then euthanized by overdose of pentobarbital. Each animal was then decapitated. A scalpel was used to make an incision in the skin along the midline of the calvaria, and a periosteal elevator was used to expose the underlying bone over the defect area. The calvaria was dissected using a cordless reciprocating saw with wood-cutting blades. The sample was fixed in 10% formalin for 7 days, then placed in DPBS for MicroCT imaging. After imaging, samples were decalcified in 20% EDTA at 55° C. for 6 weeks or until pliable. Decalcified samples were dehydrated and embedded in paraffin for sectioning.

Example 19. Dental Pulp Neural Crest Cells with HA/TCP Nanoparticles Regenerate Bone in Full-Thickness Calvarial CSDs Our previous investigation confirmed the potential of MSCs to regenerate calvarial bone in the presence of HA/TCP, which promotes stem cell differentiation into osteoblasts. We initially tested this in nude mice by creating a CSD in the mouse calvaria, away from the sagittal suture. After 6 weeks post-injury, the defect was fully healed.

In swine, the definition of a 'critical-sized' calvarial defect has not yet been fully established in the literature. More generally, a CSD is an injury that will not heal completely over the lifetime of the animal, or more conservatively, over the time course of the study in question, if no intervention is made (Park et al., Stem Cells and Development, 2016). It has been reported that a 2×4 $cm^2$ defect in minipig long bone meets this criterion, so we decided accordingly to create a round defect with a diameter of 3 cm (area of 7 $cm^2$ or larger) in the farm pig calvaria (Li et al., Journal of Orthopaedic Translation, 2015). The 3 cm-diameter defects in control swine without cells or HA/TCP failed to heal over the course of our study, which was 8 weeks (n=3). We can therefore define a swine calvarial CSD as a defect of at least 3 cm diameter, which does not normally heal within 8 weeks.

To test the potential of MSCs delivered with HA/TCP for cell-mediated bone regeneration in the swine calvaria, we treated 3 cm calvarial CSDs in swine with DPNCCs and HA/TCP and compared them to controls (no cells or HA/TCP) after 8 weeks. We observed a marked difference in bone regeneration between control swine (no HA/TCP or DPNCCs, n=3) and those that received HA/TCP and DPNCCs (n=3). CSDs treated with HA/TCP and DPNCCs showed complete calvarial bone regeneration, suture formation, and normal density when compared to the native calvarial bone (n=3, with 100% success rate). We also evaluated the regenerative ability of fibroblasts isolated from the gingiva and heat-inactivated DPNCCs in the CSD. Both fibroblasts and heat-inactivated cells transplanted with HA/TCP nanoparticles were insufficient to heal the CSDs, as there was no new calvarial bone regeneration in either group (n=3 per group). To confirm that the osteoconductive HA/TCP was not solely responsible for the regeneration observed in the DPNCC+HA/TCP group, we tested HA/TCP alone in the defect. HA/TCP alone was insufficient to support bone regeneration. Taken together, this series of experiments demonstrates that live stem cells are crucial to the calvarial bone regeneration observed in the DPNCC+ HA/TCP group. Although we established that DPNCCs with HA/TCP particles were sufficient for bone regeneration, the possibility remained that the density and aesthetics of the regenerated calvarial bone could be improved. We therefore sought to develop an osteoinductive 3D-printed scaffold that would assist in the even distribution of stem cells in the defect, producing a smoother surface.

Example 20. Optimization of the 3D-Printed Osteoconductive Scaffold

We have generated a 3D-printed biodegradable scaffold based on a CT scan of a calvarial CSD in an adult swine. This scaffold has a domed shape. The top surface is a circle of 3.8 cm diameter and the bottom is another circle with 3.5 cm diameter. The bottom is concave and closely matches the curvature of the inner skull surface, whereas the top is flat and designed to be filled with the restorative materials (DPNCCs and HA/TCP) via 2 mm holes. We have tested a scaffold fabricated using a PEGDA-GelMA double network and confirmed its biocompatibility. Testing polycaprolactone dimethacrylate (PCLDA) indicated that PCLDA may not be toxic to cultured cells and is biodegradable.

The photo-curing process for 3D-printing did not easily allow the use of HA/TCP nanoparticles alone, so we decided to combine HA/TCP with an FDA-approved, biodegradable polymer that would degrade throughout the course of healing. This allows the scaffold to slowly be replaced with bone throughout the 8 weeks.

Example 21. Healing of CSD Using HA/TCP 3D-Printed Osteoconductive Scaffold Instead of Nanoparticles Improved Quality of Regenerated Bone Bone regeneration using HA/TCP particles with DPNCCs did not yield results that were optimal for clinical application. In these animals, the calvarial surface was indented. Since bone regeneration was still achieved despite these surface features, we reasoned that structural organization of the transplanted cells would aid their formation of bone in a more ideal pattern. Following transplantation of the HA/TCP 3D-printed scaffold with DPNCCs into the calvarial CSD, regenerated bone more closely resembled the surrounding native bone (n=6). All other parameters remained the same: the size of the full-thickness defects were 3 cm in diameter and 3-4×10$^6$ autologous DPNCCs were transplanted. One caveat of using the scaffold was that the HA/TCP did not fully degrade in the course of 8 weeks. We are currently testing the time-frame of dense HA/TCP biodegradation in vivo. In addition, we are optimizing the dimensions of the scaffold pores to allow more efficient biodegradation.

Example 22. Long Bone Marrow Stem Cells Regenerate Bone in Full-Thickness Calvarial CSDs It may be the case that the procedure of harvesting DPNCCs, which involves extraction of a tooth, may be infeasible or unacceptable for human patients; the number of cells obtained in this manner is also meager, and thus expansion in culture is required. This expansion period is lengthy, which is a significant consideration for a patient with a large skull defect. In order to circumvent these drawbacks, we tested the regeneration potential of MSCs from another source, namely the bone marrow. Previous studies have demonstrated that transplantation of long bone marrow MSCs into a bony defect results in the formation of a marrow space in the regenerated bone. This trabecular bone is much less dense than the cortical bone of the calvaria. However, collecting bone marrow may be more acceptable than collecting dental samples for human patients, would allow a larger number of cells to be obtained, and would reduce the number of anesthetic events necessary. Transplanting bone marrow MSCs directly into the CSD would also eliminate any potential contamination or loss of stem-ness due to expansion in cell culture.

Example 23. Calvarial Bone Regeneration

Regenerated calvarial bone must integrate with existing bone, participate in homeostasis, and in the case of children, accommodate future brain growth. Current cranioplasties involve implantation of metal or plastic plates or autologous bone grafts to protect the brain, all of which have significant drawbacks. In this study, we have regenerated calvarial bone using cranial neural crest MSCs from the dental pulp delivered with HA/TCP or an osteoconductive 3D-printed scaffold to fill CSDs. We have developed and generated extensive preliminary data with a swine model that has a head size and skull thickness similar to those of humans, unlike most calvarial CSD studies that focus on rodent models. Laying the groundwork for studies of stem cell-mediated calvarial repair, we established that a 3 cm diameter defect in the swine calvaria will not heal over the course of 8 weeks and therefore represents a suitable CSD model in this animal.

Our novel, osteoconductive, 3D-printed scaffold supports MSCs, providing them with a suitable osteogenic environment and holding them in place during bone regeneration. The result is that the MSCs undergo differentiation into osteoblasts and regenerate bone, filling in the CSD over the course of 8 weeks. This method of calvarial CSD repair is superior to current clinical solutions. Plates, implants, and grafts cannot support normal tissue homeostasis or continued growth as they do not provide cells that regenerate damaged tissue or build sutures from which bone growth occurs. Further investigation needs to be performed to determine whether homeostasis in regenerated tissue is normal and to ensure that it does not result in tumorigenesis or other adverse effects over a long period of time.

We have confirmed that HA/TCP alone, heat-inactivated MSCs, and fibroblasts are insufficient to heal the CSD in our swine model; live MSCs appear to be necessary for complete healing over the time period of our study. Other endogenous cells may also play a role. For example, the dura and periosteum contribute fibroblasts to injuries and play a large role in wound repair, and it may be that these fibroblasts play an indirect role in repair by organizing stem cell progenitor cells that become osteoblasts. Further study is needed to analyze the cell-cell interactions in the CSD injury repair model.

In summary, we have established a novel approach to skull bone regeneration that combines a 3D-printed scaffold with stem cell-mediated repair. In comparison to the current gold standard, our approach will offer patients a safe and effective biological treatment to restore calvarial bone/suture function for patients with calvarial CSDs.

Figure 19:
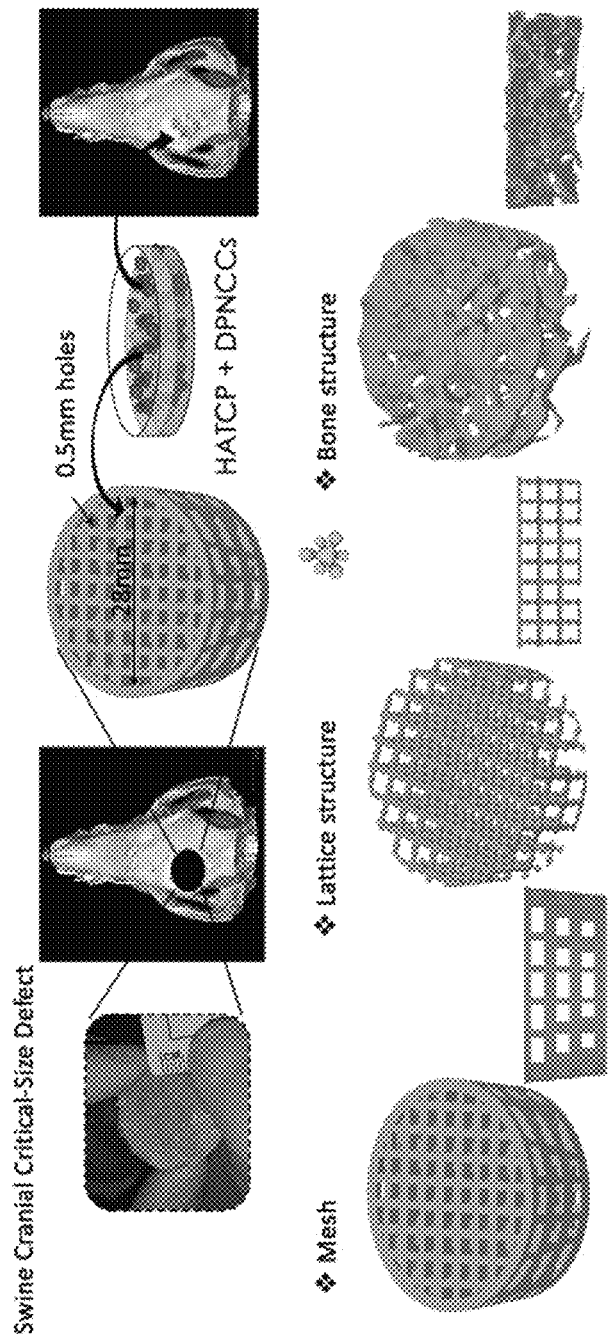
FIG. 19. The design procedures of scaffold for cranial defect regrowth.

Example 24. Design of Scaffold for Suture and Long Bone Regeneration Critical Cranial Defect Regrowth By designing the lattice structure for the pig scaffold, we can study how the surface (e.g. surface area) can benefit the cells growth, as well as the release rate of the growth factor. Unlike the mesh structure, the lattice structure requires much more complicated design approach. Our method repeatedly performs Boolean with a unit cell and forms a periodic structure. Then we intersect it with the desired shape to create the final lattice structure. However, current method does not consider manufacturability in the design. Some features appear as part of the unit cell on the boundary surface, which may introduce instability to the performance of the whole structure. The same situation could also happen when we fabricate the bone-like structure. We developed a new set of tools for the scaffold construction so that facilitating the study and enable designing the best solution for various situation, including the long bone and skull defeats regeneration. For the cranial defect bone scaffold, we come up with design as shown in FIG. 19. The scaffold is designed with micro-scale porous structure, enabling bone cells grow throughout the whole defeats. To study how the shape of scaffold can make impact on the bone growth, scaffolds with three different kinds of micro structures were designed.

Long Bone Regeneration

Figure 20:
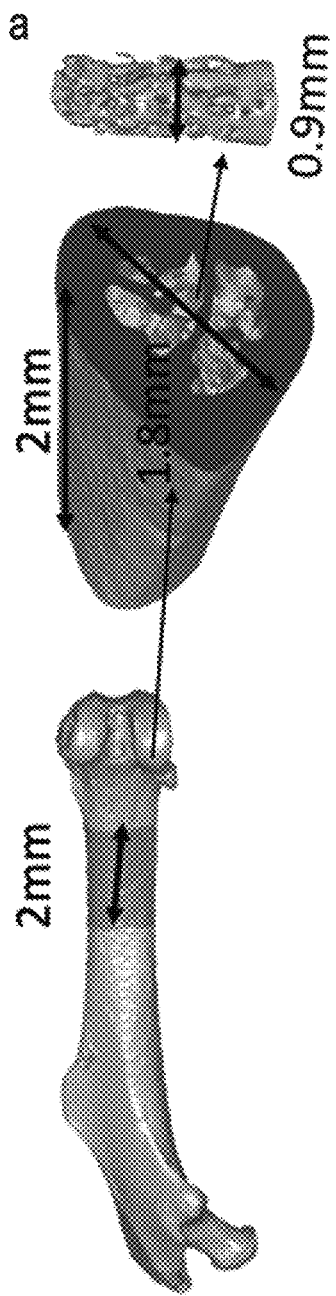
FIG. 20. Scaffold design of long bone regeneration. CNCCs and BMMSCs produce different types of bone. Depending on the site to be repaired, either dense cortical bone (craniofacial, CNCCs) or bone with more marrow space (long bone, BMMSCs. (A) Long bone, (B) Regeneration of bone: after 2 weeks, 5 weeks, and 12 weeks, 1.5 mm defect is healed, but not 2 mm defect, (C) An example of a scaffold comprising two chambers, an inner chamber for bone marrow growth ("bone marrow scaffold") and an outer chamber for cortical bone growth ("cortical bone scaffold). (D) an example of long bone treatment.
Figure 20:
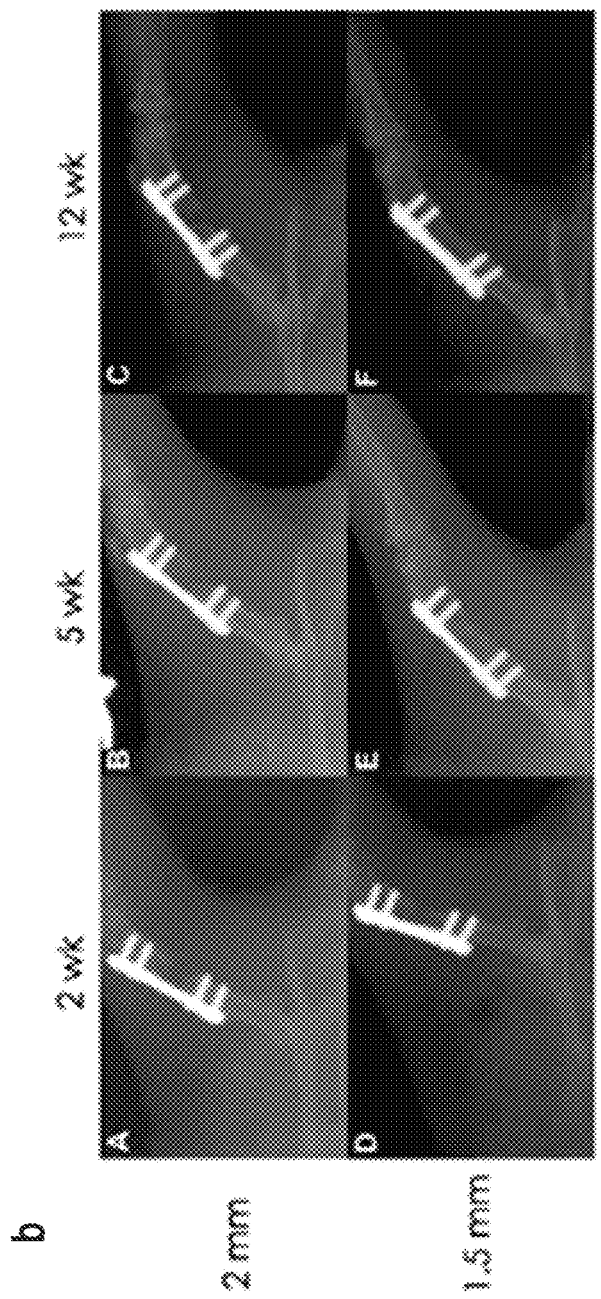
Figure 20:
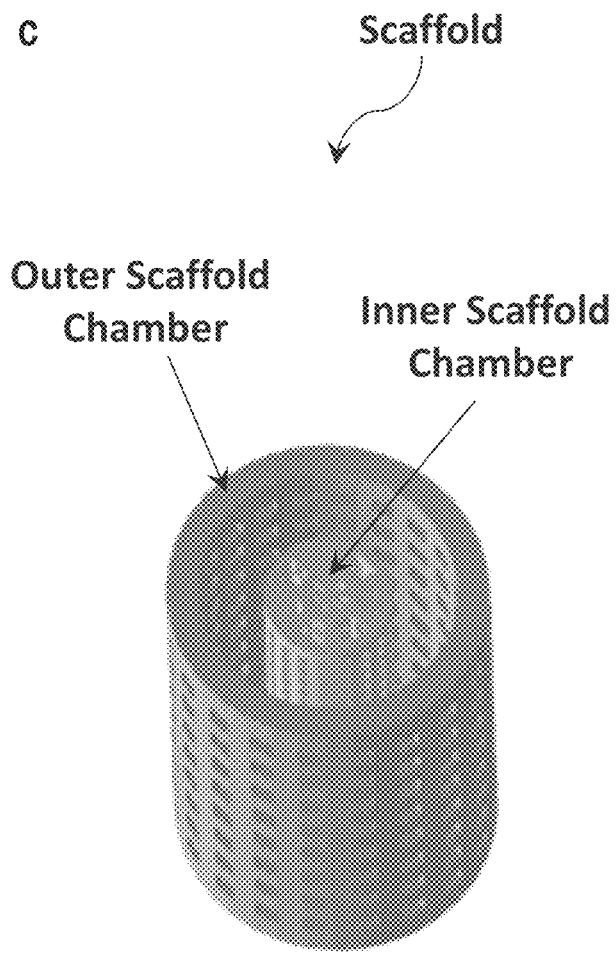
Figure 20:
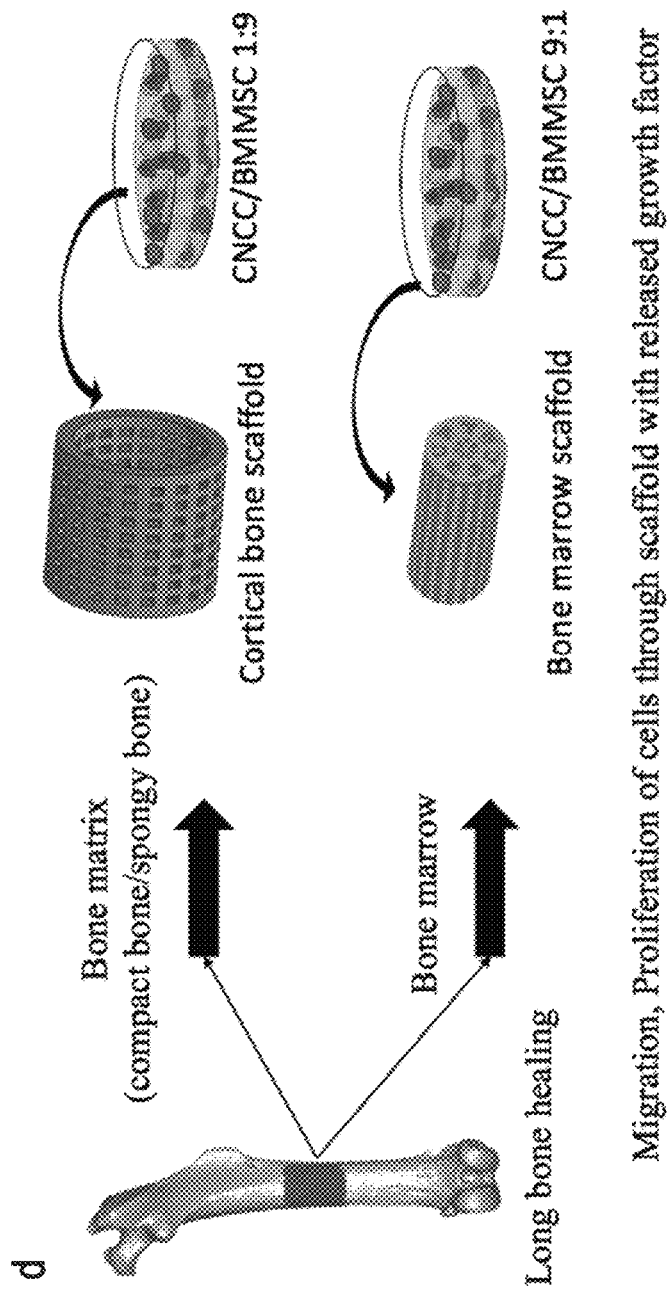
Figure 22:
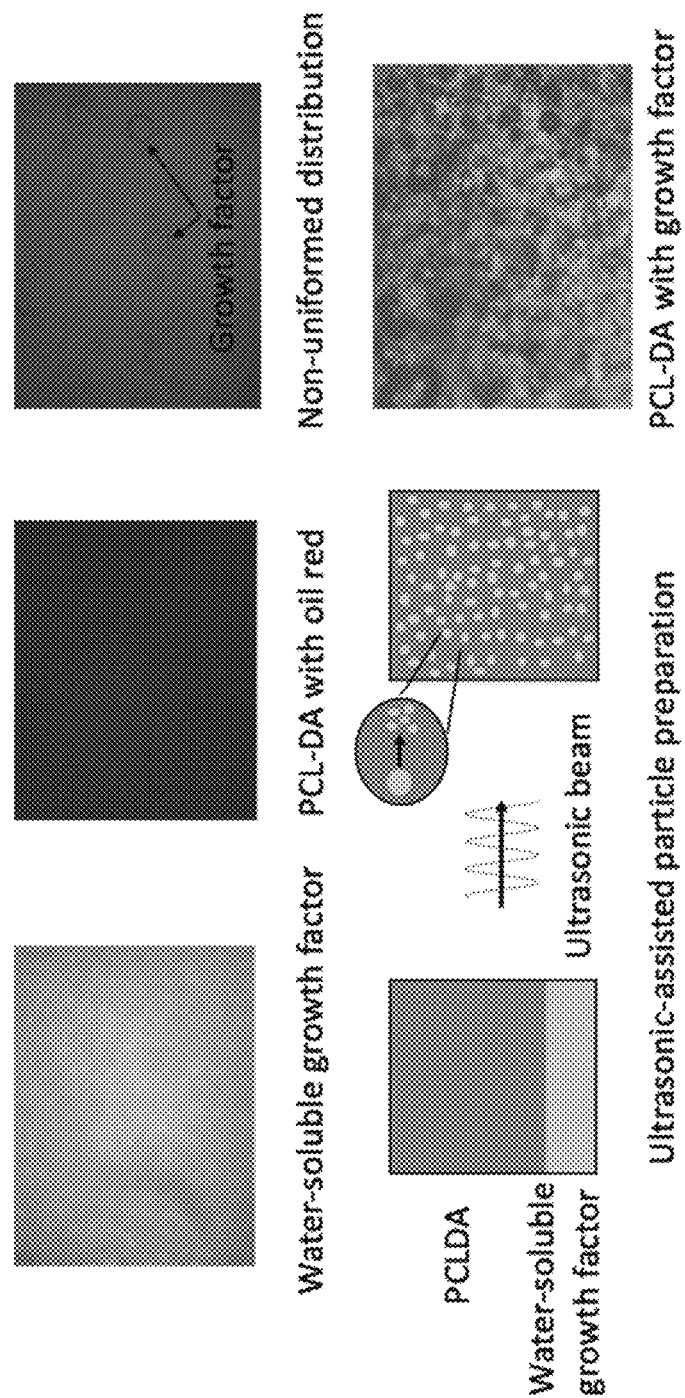
FIG. 22. Diagram of PCL-DA based biomaterial preparation.

We had designed a long bone scaffold based on the actual shape and structure extracted from the CT scans. There are two chambers in the structure: the scaffold cultured with the mixture of CNCC/BMMSC in 9:1 ratio enables the cell growth with nutrition coming from the designed holes (i.e. pores). The second portion is the cortical bone scaffold. The structure support the stem cell composition comprising the mixture of CNCC/BMMSC in 1:9 ratio. Larger amount of BMMSC may enhance new bone growth that can provide enough mechanical strength to the scaffold to withstand the physical loading. Due to the different functionalities, we designed the scaffolds for each portion (see in FIG. 20).

For long bone healing, we aim to optimize the scaffold to find the best design for the long bone regeneration. For example, cortical bone scaffold needs to withstand much larger loading than marrow scaffold. Therefore, it is necessary to study the relationship between the shape (e.g. unit cell), material and their mechanical properties. We designed the scaffold with three different shapes: mesh matrix, micro lattice structure, and biomimetic bone structure (refer to FIG. 21).

Example 25. Material Selection

The synthesis of photocurable HA/TCP suspension for Critical cranial defect regrowth.

Hydroxyapatite used in this study were nano-sized powder with particle size smaller than 200 nm (purchased from Sigma-Aldrich), and β-tricalcuim phosphate used in this study were micro-sized powder with particle size 4 μm (purchased from Sigma-Aldrich). The photo-curable liquid polymer SI500 (purchased from EnvisionTEC.Inc), which can accurately build parts with high feature detail, was used to be the polymer binder. To figure out the optimal HA/TCP particle mass ratio δ, 10 wt %-40 wt % HA/TCP suspensions were prepared followed the below procedures. Firstly, the HA/TCP powder was poured into the liquid photopolymer resin (SI500). Then the HA/TCP slurry was ball-milled with rotational speed 200 rpm for 40 min. After that, the HA/TCP suspension was degassed in the vacuum before fabrication. To reduce cure depth of HA/TCP suspension, 0.1 wt %, 0.25 wt %, 0.5 wt %, 0.75 wt % and 1 wt % light absorber (oil red purchased from Sigma-Aldrich) was added to the polymer resin SI500 respectively. Then 30 wt % HA/TCP was added to this polymer mixture, and the 30 wt % HA/TCP suspension with light absorber was prepared followed above procedures.

Example 26. The Synthesis of Polycaprolactone Based Photocurable Composite for Long Bone Regeneration Photocurable Polymer Solution Preparation:

Polycaprolactone dimethacrylate (PCL-DA) were purchased from Sigma-Aldrich, Photoinitiator Irgacure 819 were obtained from BASF Chemistry. HA (Hydroxyapatite) and TCP (Calcium phosphate-tribasic) are bone material, we also use rh/mlhh(c28II)-N and rh/m/rBMP-2 as growth factor. Oil red as light-absorbing agents, were used to reduce the curing depth of the monomers and adjust the thickness of the microstructures in the fabrication process. To prepare the 40% HA/TCP solution with growth factor, firstly 1% (w/v) Irgacure 819 was dissolved thoroughly 100% (w/v) PCL-DA at 35° C. for one hour. After that, we added 10% HA and 10% TCP inside the PCL-DA solution using ball milling machine. To control cure depth of material, we also add 0.1% (w/v) Oil red inside the solution. After we get the material, we prepare growth factor, we dissolved rh/mlhh (c28II)-N and rh/m/rBMP-2 in a phosphate buffer saline (PBS) solution. Since water based growth factor cannot be dissolved inside the PCL-DA solution. As shown in FIG. 21, we used ultrasonic machine to uniformly distribute water droplet which dissolved growth factor inside the PCL-DA solution.

Example 27. High Viscosity HA/TCP Suspension Printing Process

The Hardware and Software Design

Stereolithography (SLA) is one of main high resolution additive manufacturing technologies to process high viscous material. In Mask image projection based stereolithography (MIP-SL) process, a 3D object is firstly sliced by a set of horizontal planes and each thin slice is converted into a two-dimensional (2D) mask image. Generated by the DMD chip with mask image, the 2D patterned light beam is projected on the surface of photo-curable material. A layer of material can be cured by the 2D patterned light beam after receiving enough energy from light exposure. Thus, 3D object can be printed gradually by stacking each layer. Using MIP-based Stereolithography, it is high efficiency to fabricate macro-scale model with hundreds of layers of depositions because it can fabricate one layer within only one time of illumination. The composite material like multifunctional ceramic are successfully fabricated using MIP-based SLA process.

The printing device comprises hardware and software modules. All the fabrication processes are controlled and monitored. The prototype of the high viscous 3D printer contains three subsystems: optical imaging system, mechanical moving system, and material feeding system. The schematic diagram of prototype machine was shown in FIG. 23. For optical imaging system, the light illuminates the Digital Micro-mirror Device (DMD) and is reflected by the DMD chip. The light intensity can be changed based on the angle of mirror in the DMD. Light goes through the optical lens, and the focusing image will be generated at the surface of the resin and the resin will be cured with suitable exposure. After curing one layer, the z stage will move to next layer position, then resin surface is refreshed and the next focusing image is exposed. Each layer of image is based on the geometry of the fabricating object. For the size and resolution of each MIP system, the combination of lens is different for the size and resolution required, and usually the size of model can range from 1 micrometer (micro-scale) to 200 millimeter (macro-scale).

Figure 24:
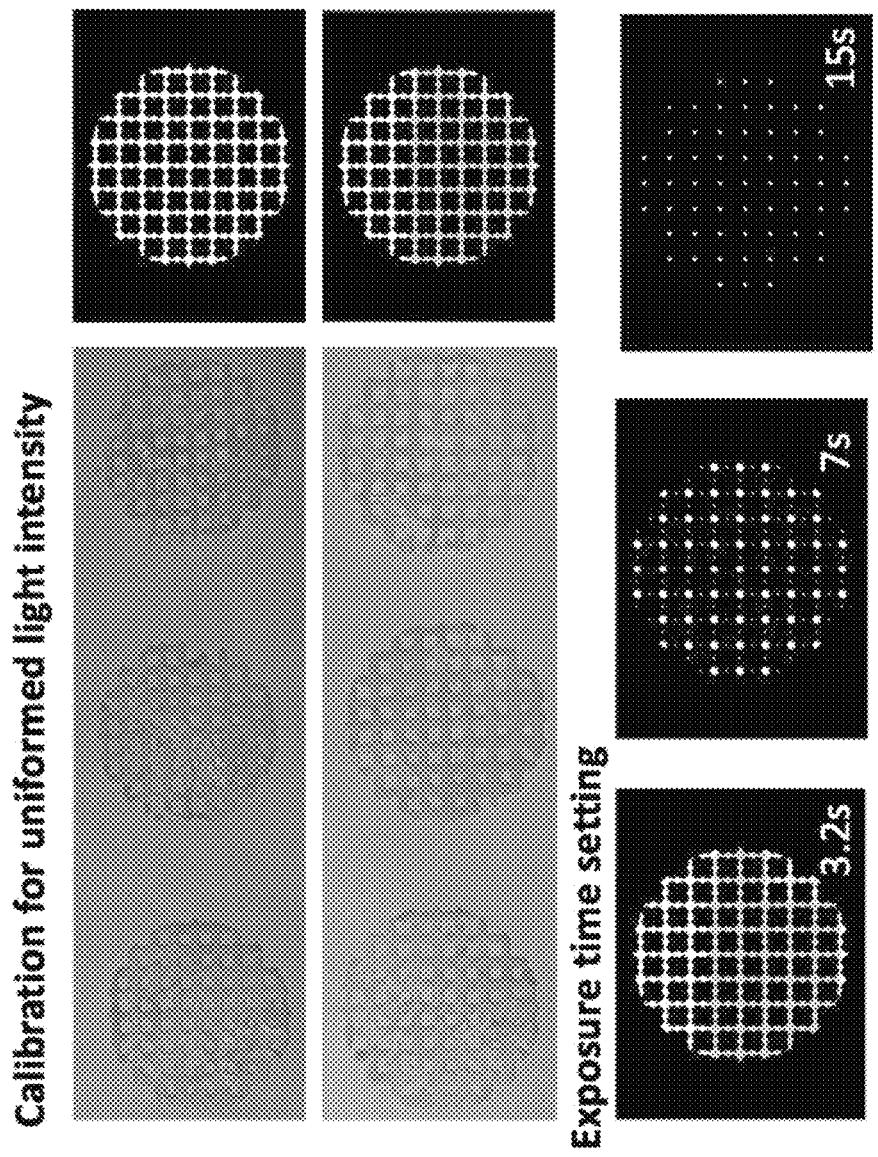
FIG. 24. Light calibration and exposure time setting in macro-scale rotary MIP based Stereolithography.
Figure 26:
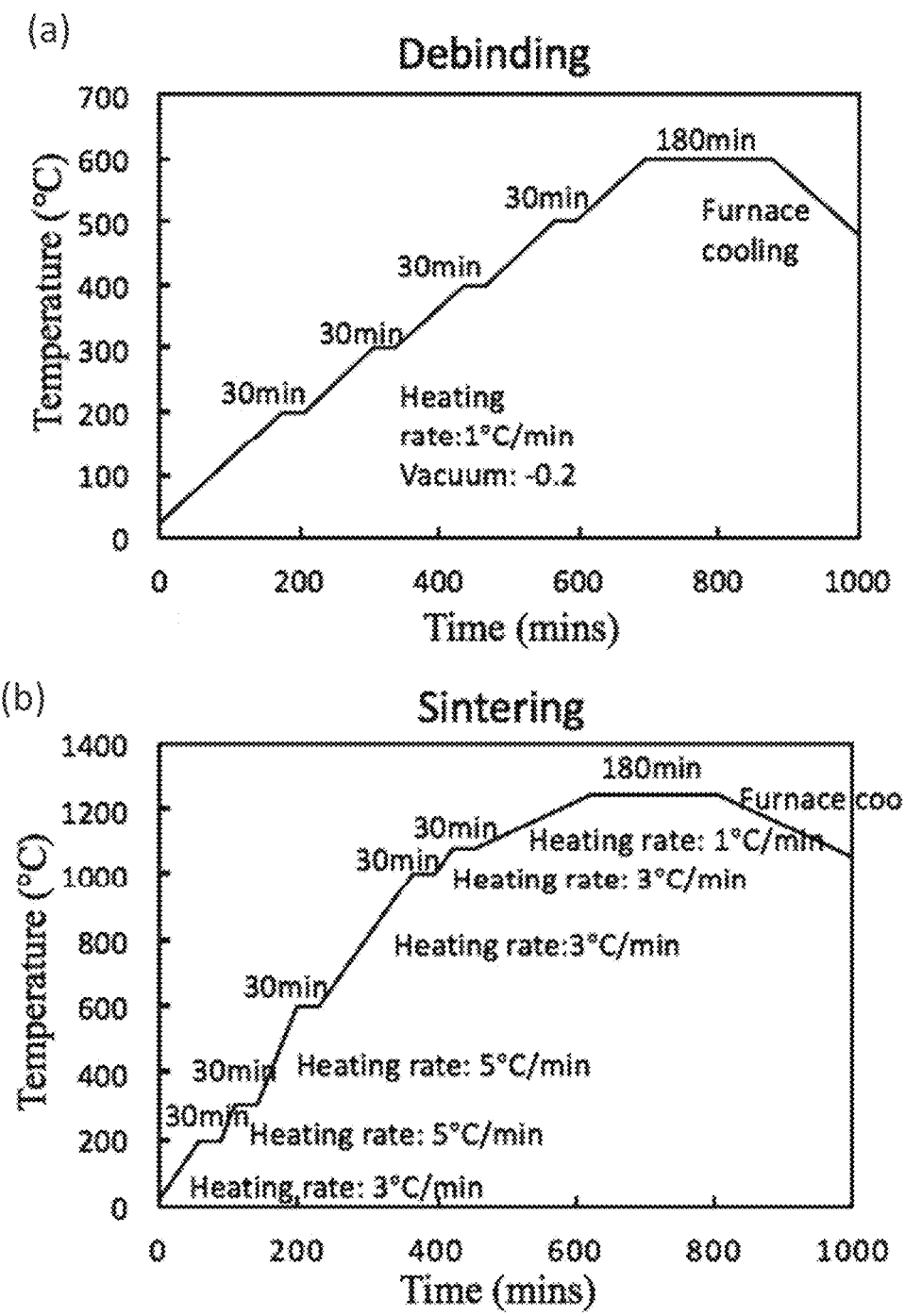
FIG. 26. Debinding and sintering temperature setting curve.
Figure 27:
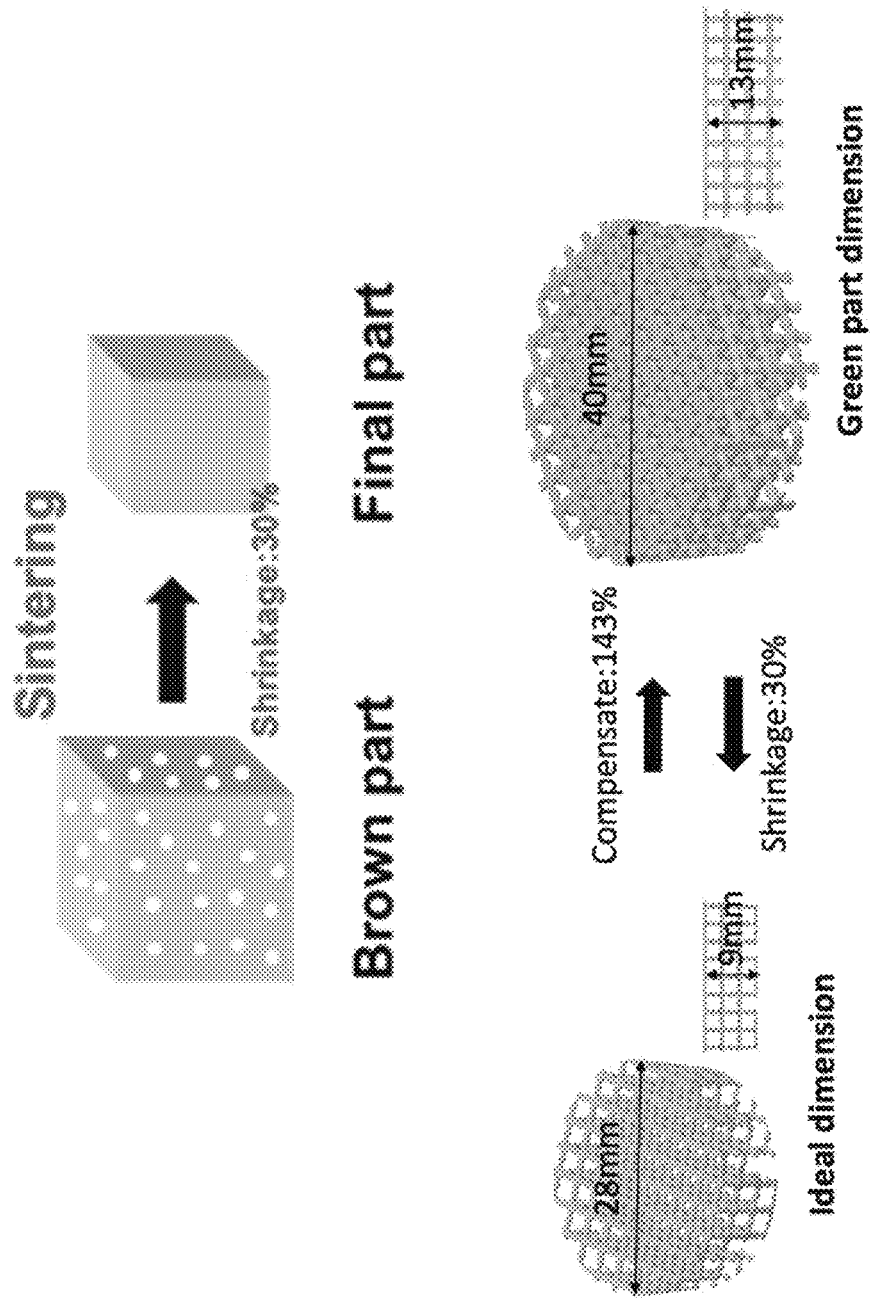
FIG. 27. The compensation design of HA/TCP scaffold.

The dimension of projection image discussed in this test was 45×33.75 mm$^2$. And the resolution of DMD chip from Texas Instruments Co. was 1920*1080, meaning the resolution of this 3D printer can reach 24 µm/pixel. A mask planning testbed has been developed using the C++ language with Microsoft VISUAL C++ compiler. The testbed integrated the geometry slicing and the motion control. It also synchronized the image projection with the X and Z movements. Since the light distribution is not uniformed, using mask image with whole gray scale, some portion of part is over-cured while some portion cannot be cured. To increase fabrication resolution, we conducted experiment to calibrate the light intensity of projection image. We adjust the gray scale of mask image to achieve uniformed light distribution refer to FIG. 26. After we get uniform light intensity, since there are micro-scale holes inside the scaffold, we may need to fabricate structures using minimum number of pixels. For example, we may need a few number of pixels. To fabricate such small features, we need to increase exposure time to make sure the material receives enough energy to cause photo polymerization. The result of exposure time setting was also shown in FIG. 24.

However, the HA/TCP suspension was unable to flow to the thin film only driven by the air pressure and the gravity of material. The material refilling of high viscous material is one big challenge that limits the MIP-SLA process to fabricate high viscous material. Thus, we added the material feeding system to continuously coat the material with 100 µm thickness. To refilling high viscous material, special tools like blade are necessary to achieve the uniform coating of material and the shear force should be big enough to spread material into thin layer of film.

The Process Planning

For macro scale process, the material feeding process is improved for larger projection area and more building layers. Unlike the linear way of material feeding, the material is put into a circular shape building tank, which is attached to a rotary platform that can rotate the tank with variable speed. A blade is added above the material to control the thickness of material by allowing a small horizontal gap parallel to the bottom of building tank. During the fabrication, the building platform is raised for a certain distance after each layer is built and the rotary platform rotates to feed material to the blade. The blade scrapes at the top of the material so only the material at the thickness needed for each layer passes to the location below the building platform. Building platform is lowered to building position after material is fed correctly and the building of current layer starts. Similarly, such process repeats until the building of part finishes (refer to FIG. 23). To solve the refilling problem of high viscous HA/TCP suspension, a fast material feeding process with circular movement was integrated in micro-scale MIP-SL system. Firstly, a thin layer of HA/TCP suspension with thickness of 100 µm was evenly coated on the top surface of glass plate with Teflon film by doctor blading (refer to FIG. 23). After curing the first layer of HA/TCP suspension, the building platform was firstly raised up $Z_1$, which was larger than the thickness of coated HA/TCP layer, and at the same time the glass slide coated with HA/TCP suspension moved rightly in X direction. Even the material plate was moved in x direction, the relative position of projection light and building platform didn't change. After the movement of glass plate, the new material was transported to the place where the exposure light was projected. When the movements of platform and glass plate finished, the building platform was moved down back until the distance between the surface of pre-cured part and light projection place was equal to the cure depth of material. With the above circular movement, new layer of HA/TCP suspension was constantly fed to the location right below the building platform within only several seconds for the following fabrication, which has greatly improved the printing efficiency of high viscous material. During building process, circular movement was repeated until all layers were built on the platform.

The Post-Processing of HA/TCP Scaffold

Figure 25:
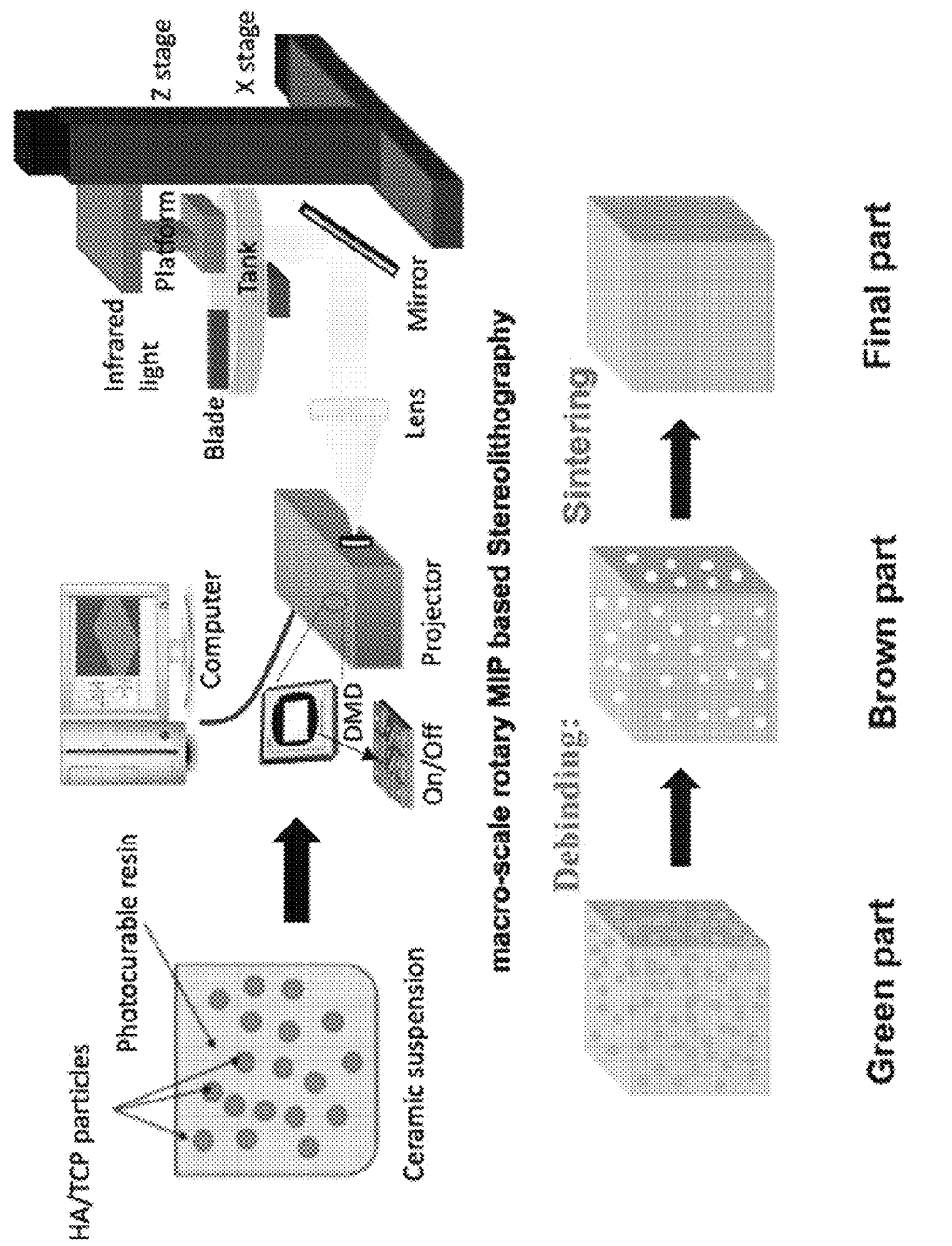
FIG. 25. The fabrication process planning of HA/TCP scaffold in macro-scale rotary MIP based Stereolithography.

HA/TCP suspension was firstly printed by the developed micro-scale MIP-SL, and low temperature debinding and high temperature sintering must be performed to remove the inside polymer, and fuse the HA/TCP particles together respectively (refer to FIG. 25). In the debinding process, the photopolymer must to be removed completely, because the residual carbon delays would affect the following process and biological performance of HA/TCP scaffold. Therefore, thermal gravity analysis (TG) were conducted to determine the debinding parameters. As the temperature increased from 300 to 600° C., the weight of scaffold green part was decreased dramatically. When the temperature reached to 600° C., the weight of green part maintained to the constant value, which was equal to the original weight of inside HA/TCP particle. Based on the result of TG test, the debinding temperature setting is followed the curve as shown in FIG. 19(b). The tube furnace used in the debinding process is GSL-1100X-SK (purchased from MTI Corp). Since the destruction of green part would occur, especially for micro-scale structures, if the gas generated by the pyrolysis exceed the safety value, the debinding process should be conducted at slow heating rate to make sure that the decomposition speed of polymer is smaller than the pyrolysis velocity. Given that, the heating rate is set at 1° C./min in the vacuum condition, and the gas is continuously sucked out by the mechanical vacuum pump to keep the pressure of heating zone at −0.12 mPA. The temperature was held for 30 mins for every increment of 100° C., and the temperature finally was increased to 600° C. and maintained for 180 mins. to complete removal of polymer. After debinding process, the removal of the polymer formed the porous structures.

The HA/TCP particles were sparse arrangement, and the brown part was too weak to support any load. Therefore, the sintering process is necessary to firm HA/TCP particles and improve the mechanical property of the HA/TCP scaffold. The shrinkage ratio and mechanical strength of HA/TCP scaffold will be affected by the sintering temperature, since the temperature has influence on the grain-boundary and volume diffusion of ceramic particles. Three different highest temperatures (1050° C., 1150° C., 1250° C.) were tested in the sintering process to identify the optimal sintering temperature of HA/TCP scaffold. The GSL-1500 (purchased from MTI Corp) was used to sintering the samples in the normal air condition, and the temperature setting curve in sintering process is shown in FIG. 19(*c*). Specifically, the temperature was firmed up to 200° C. at the heating rate 3° C./min. After waiting 30 min, the temperature was heated from 200° C. to 280° C. at the heating rate 5° C./min. Using the 3° C./min heating rate, the temperature was gradually increased to 1080° C. and hold at 1080° C. for 30 minutes. Finally, the sample was heated up to the highest temperature and hold for 180 minutes. After that the sample was naturally cooled down to room temperature.

The Compensation of HA/TCP Scaffold

After the sintering process, the inside polymer was removed and the HA/TCP particles were firmed, making the volume of HA/TCP scaffold reduced. The shrinkage ratio $r_s$ was related to the HA/TCP particles mass ratio $\delta$ and sintering temperature T. Since more inside polymer was burned off, less HA/TCP particles would be fused together. Hence, the shrinkage ratio $r_s$ of HA/TCP scaffold raised as the decreasing of HA/TCP particle mass ratio. The same tendency can be observed when raising the sintering temperature T. This is because the diffusion took place, and the centre of HA/TCP particles moved closer to each other along with the increase of sintering temperature. Furthermore, the shrinkage ratio $r_s$ of HA/TCP scaffold varied in axial and radial directions. The HA/TCP suspension was uniformed solidified under the light exposure in the radial plane, then the stress was isotropic in X/Y direction. But the HA/TCP suspension was stacked layer by layer in axial direction, so the stress in the direction Z was different from the one in X/Y direction. The 3D printed HA/TCP scaffold showed anisotropic sintering behaviours, the shrinkage ratio $r_{sz}$ in axial direction was bigger than the shrinkage ratio $r_{sr}$ in the radial direction. To be specifically, the 28 mm of HA/TCP scaffold, which is made by 30 wt % HA/TCP suspension, was reduced to only 70% of the original value after it was sintered at 1250° C. After measuring the shape change of micro pores in X/Y plane, the compensation factor $\varnothing_{xy}$ in X/Y direction was obtained. Similarly, a series of squares, whose side length ranged from 30 μm to 350 μm, were printed using same HA/TCP suspension. The dimension of printed structures was shrunk in both axial and radial directions after sintering process. To achieve the accurate fabrication of HA/TCP scaffold with designed micro-scale pores, the compensation algorithm was developed based on the experimental results.

An Example of the Fabrication Result

Figure 28:
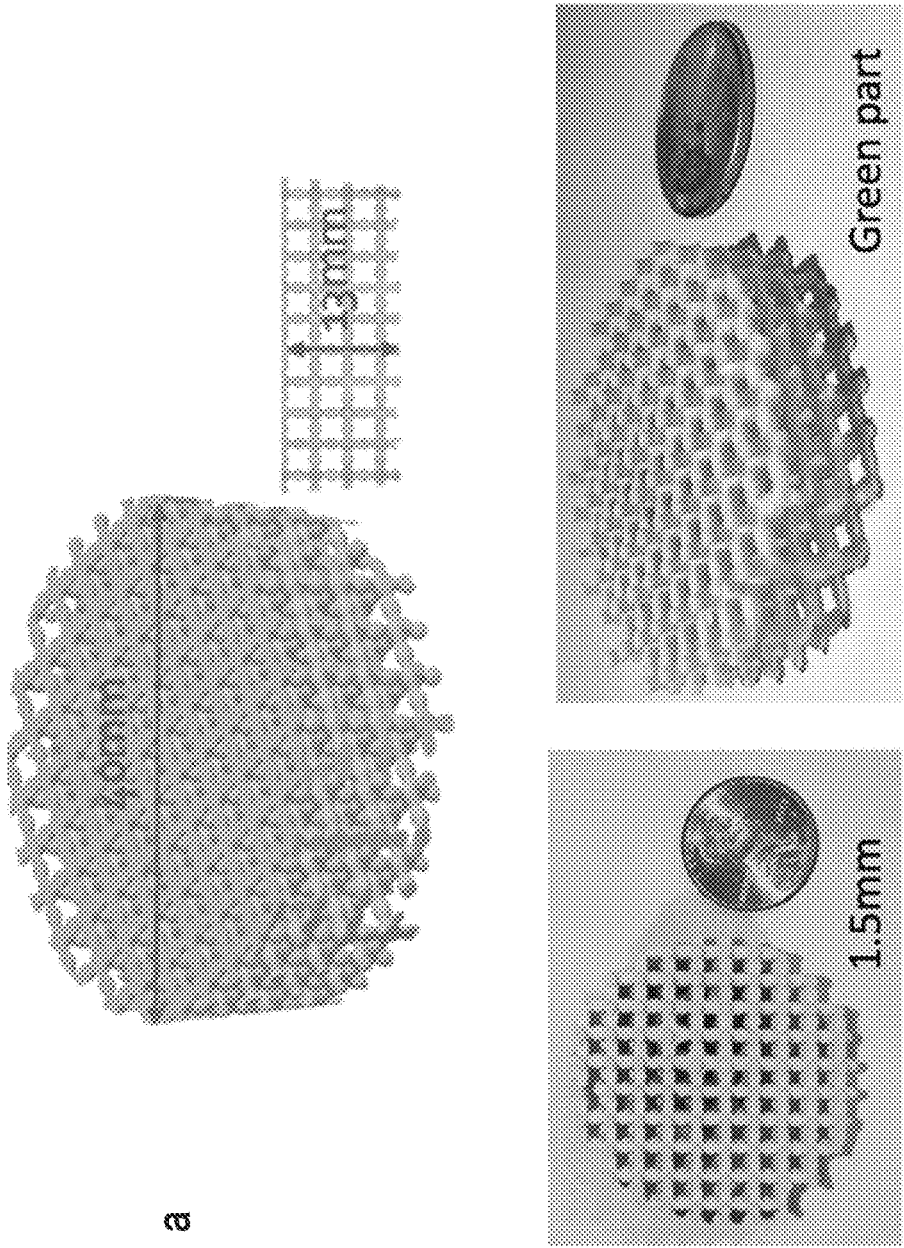
FIG. 28. The fabrication results of HA/TCP scaffold after each process. (A) Green part, (B) Brown part, (C) Final part.
Figure 28:
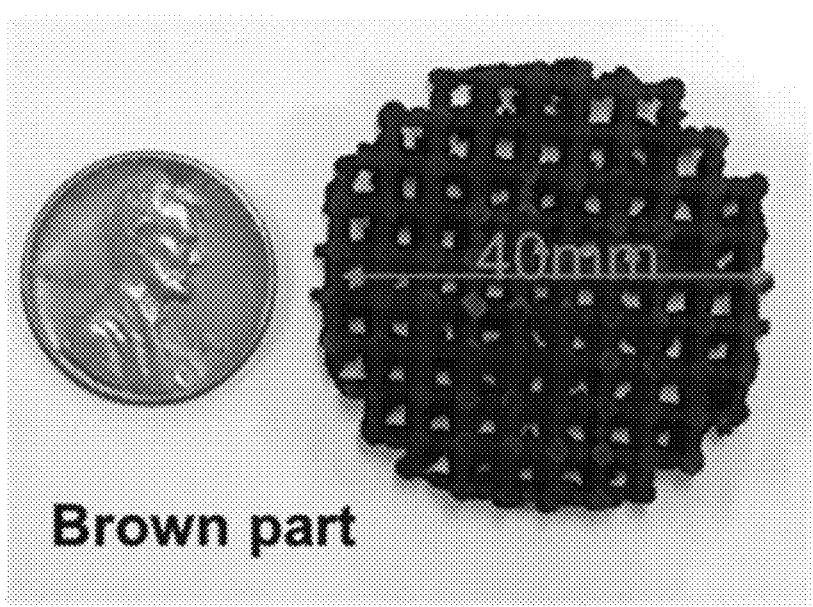
Figure 28:
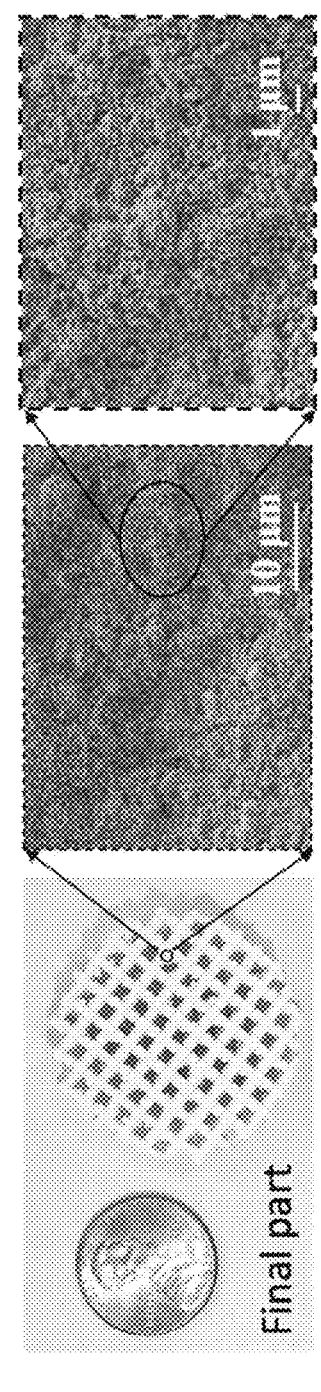
Figure 29:
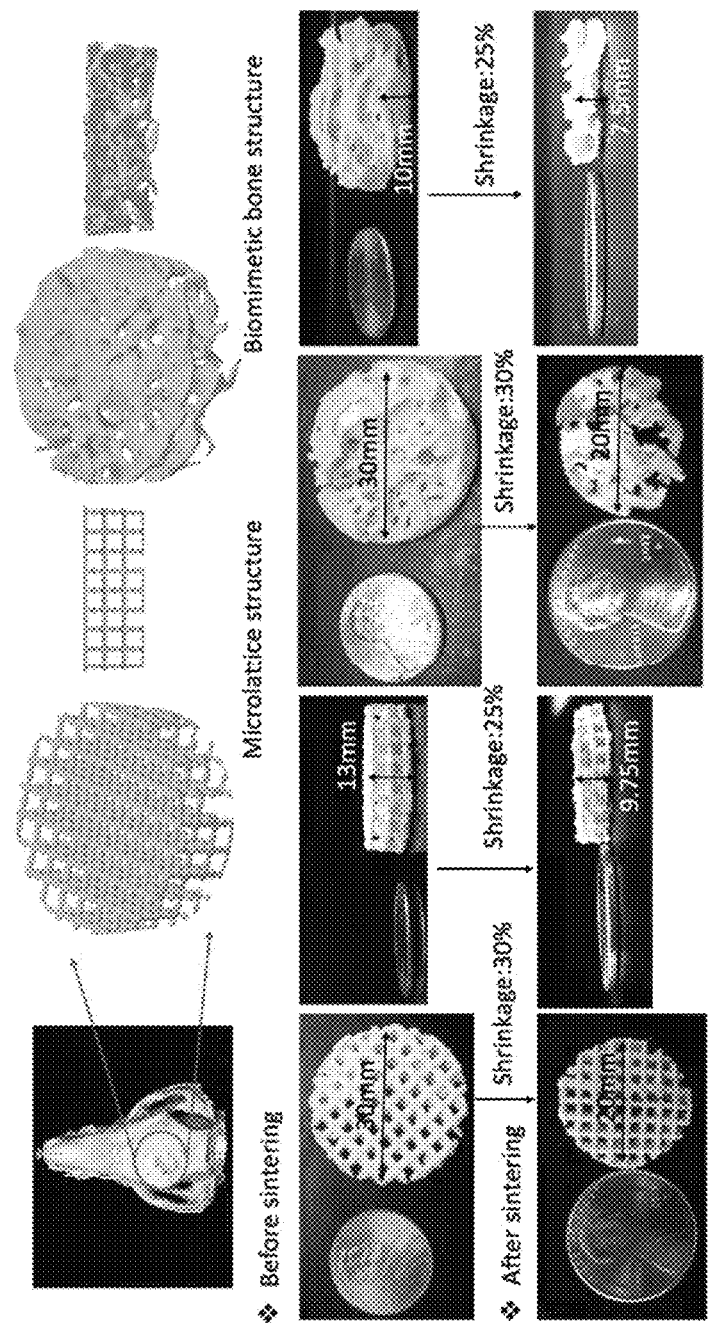
FIG. 29. The shrinkage ratio of HA/TCP scaffold with different structures.

The debinding and sintering were conducted after the green part of HA/TCP scaffold was printed by the above method. In the debinding process, the photopolymer, which was used to bind HA/TCP particle together, was removed after the temperature raised to 600° C. Plenty of pores were produced inside the of HA/TCP scaffold where the photopolymer use to be. At this stage, porosity ratio of HA/TCP scaffold reached the peak value, however, the HA/TCP brown part was fragile because of the loose arrangement of HA/TCP particles without any binding force. Therefore, the sintering process was necessary to firm HA/TCP particles, and further increase the mechanical performance of HA/TCP scaffold. The HA/TCP scaffold printed using HA/TCP suspension after each process were shown in FIG. 28. From the SEM image, there are nano-scale pores inside the HA/TCP scaffold. To increase the density of holes, hundreds of micron sized holes were designed inside the HA/TCP scaffold. For the regeneration of cranial defect, three different micro structures were applied to design the HA/TCP scaffolds. We successfully fabricated HA/TCP with different geometric shapes by using our developed high viscous MIP-SL process. FIG. 29 show the fabrication results of HA/TCP scaffolds, and the comparison of the HA/TCP scaffolds with lattice structures and biomimetic bone structures before and after the sintering, respectively.

Example 28. Micro-Scale Photopolymerization Printing Process

The Hardware and Software Design

Figure 30:
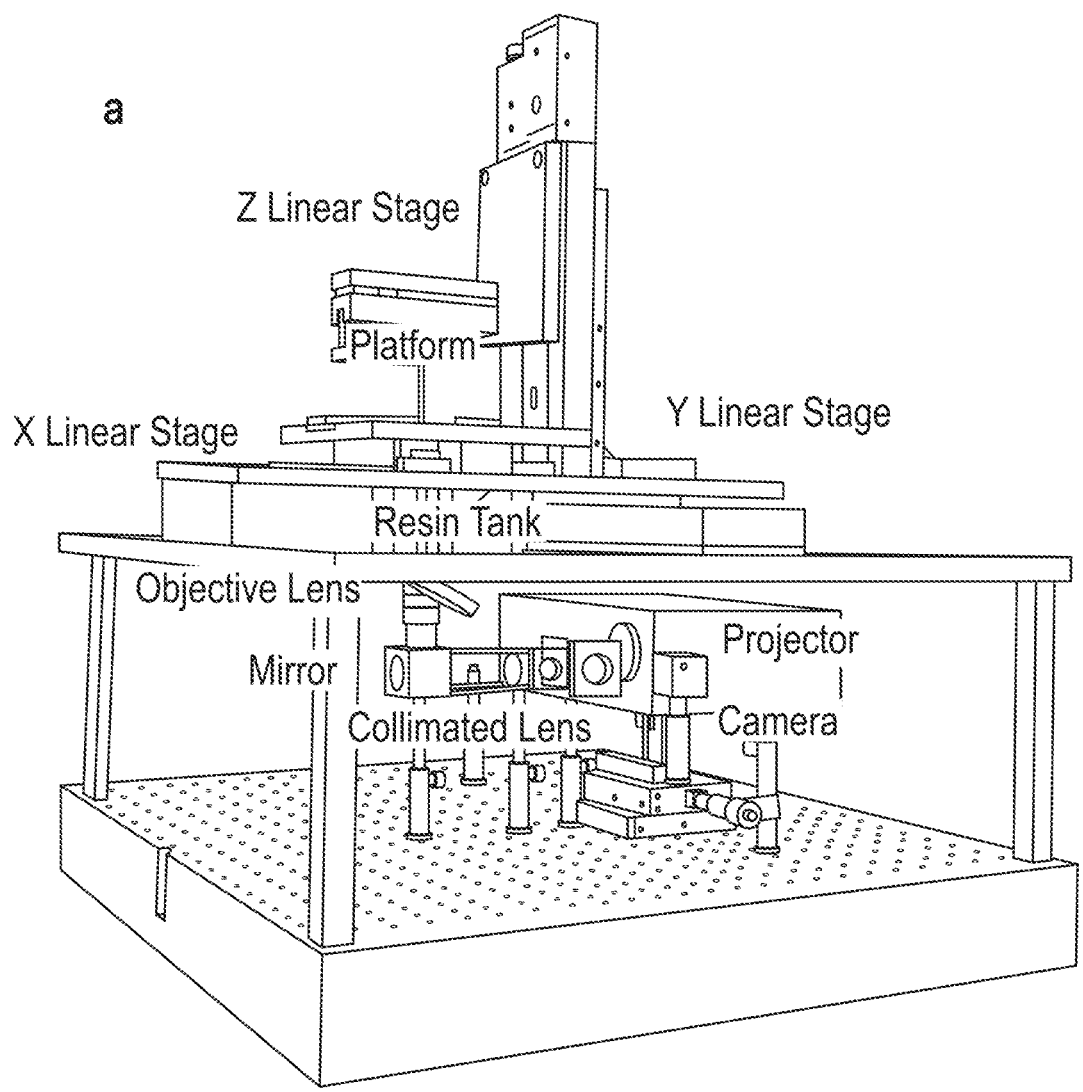
FIG. 30. The bio-printing set-up using MIP based Stereolithography.
Figure 30:
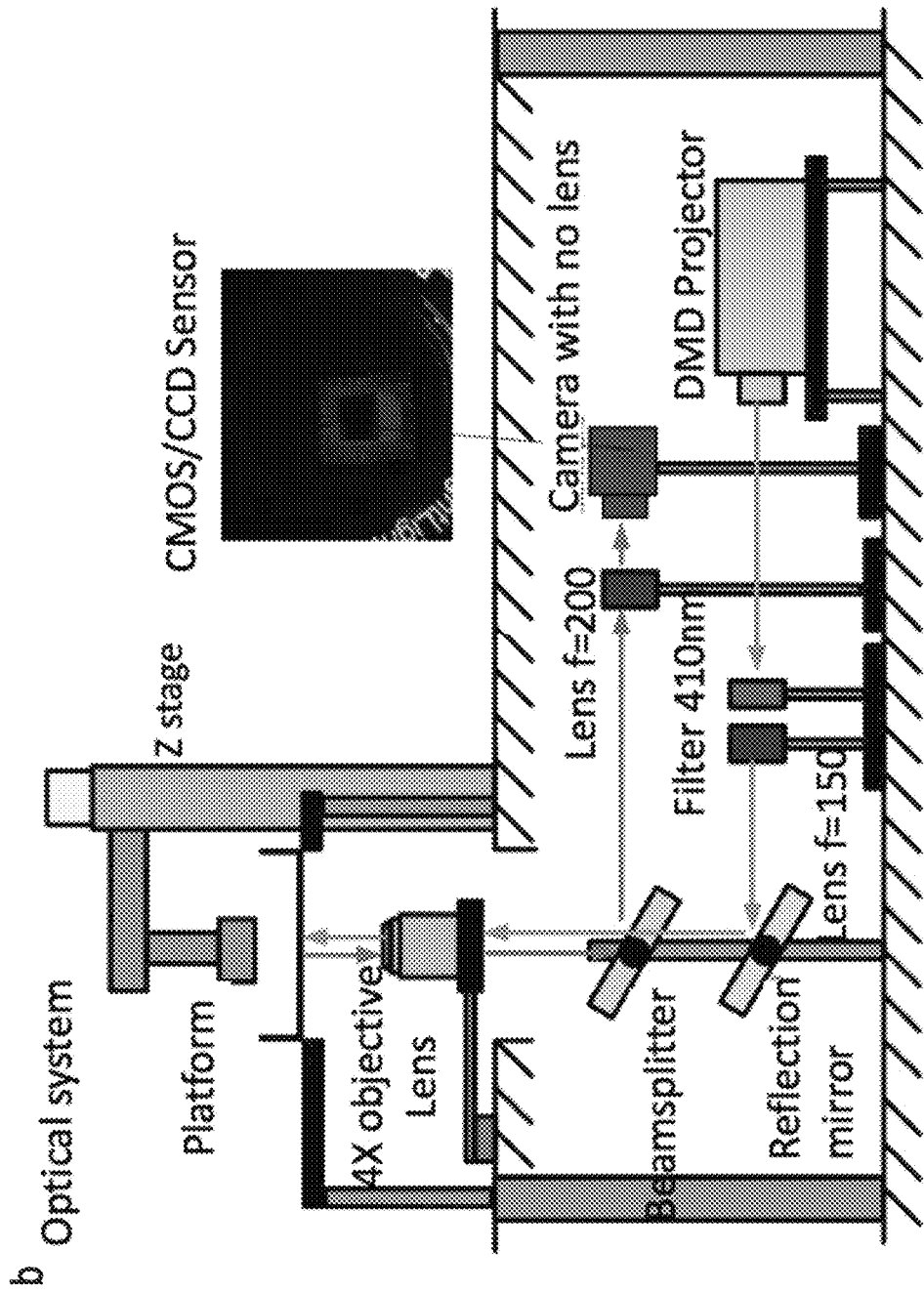
Figure 30:
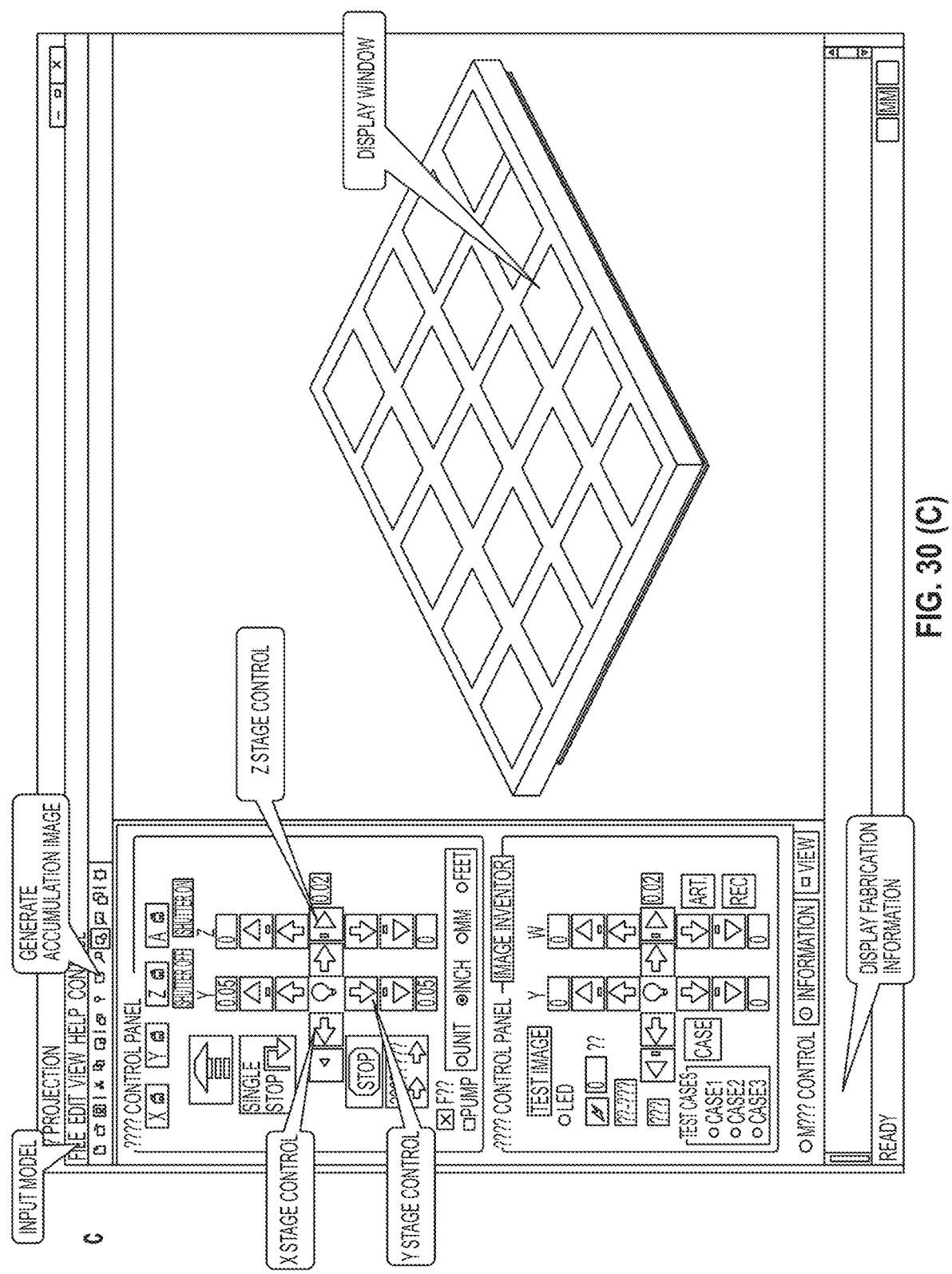
Figure 30:
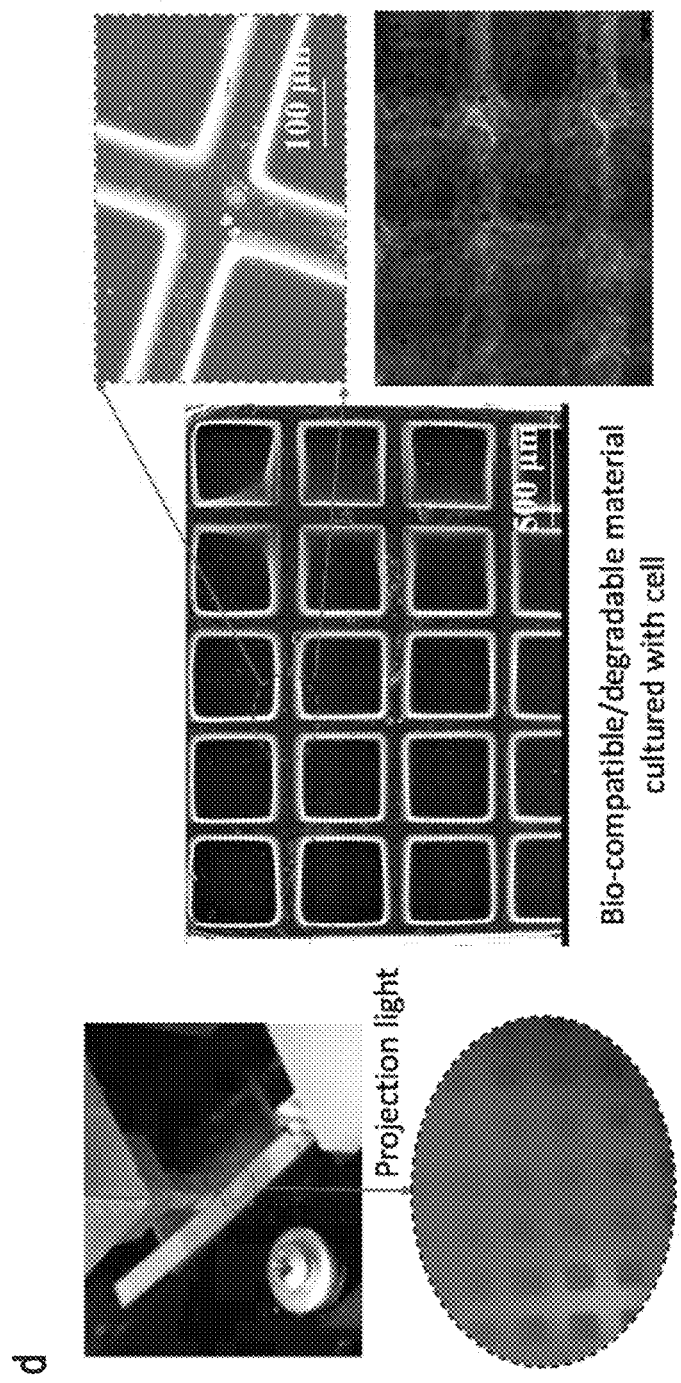

Based on the principle of MIP-based SLA, we further developed our bio-printing set-up shown in FIG. 30(*a*). In our Micro-scale bio-printing system, we use a visible light lamp to be the light source, and we considered the light source as point source that the light emitting from the light source goes through to all directions. To keep all the energy of the light, the light from the lamp should be collimated before irradiates to the DMD. We used the achromatic doublets lens to converge the light beams and to lower the impact of distortion we also used filter lens to block most of lights beams except for designated group whose wavelength is at 410 nm. The collimated light will go through the 4× objective lens, which scale the image to the dimension we need and the distance between the objective lens and collimated lens $l_{co}$ can be changed. The image size discussed in this test is 4 mm×3 mm and the resolution of DMD we use is 1920×1080, which means the resolution for this Micro-scale SLA based bio-printing system is 2.5 μm/pixel as shown in FIG. 30(*b*). We also designed light monitor system to check the light projection quality and to observe the whole fabrication process. We imported CAD model of the 3D object into the software we developed for our bio-printing system, and sliced the model with the thickness required as shown in FIG. 30(*c*). When generating the projection image, the gray scale level of each pixel will be adjusted based on the calibration database to achieve the uniform light distribution. FIG. 30(*d*) shows the fabrication area of our bio-printing set-up and the high resolution focused projection image will be located on the surface of our fabrication area. Using our bio-printing set-up, we can fabricate bio-compatible or bio-degradable material with micro-scale resolution shown in FIG. 30(*e*).

The Curing Property of PCL-Based Composite Material

Figure 31:
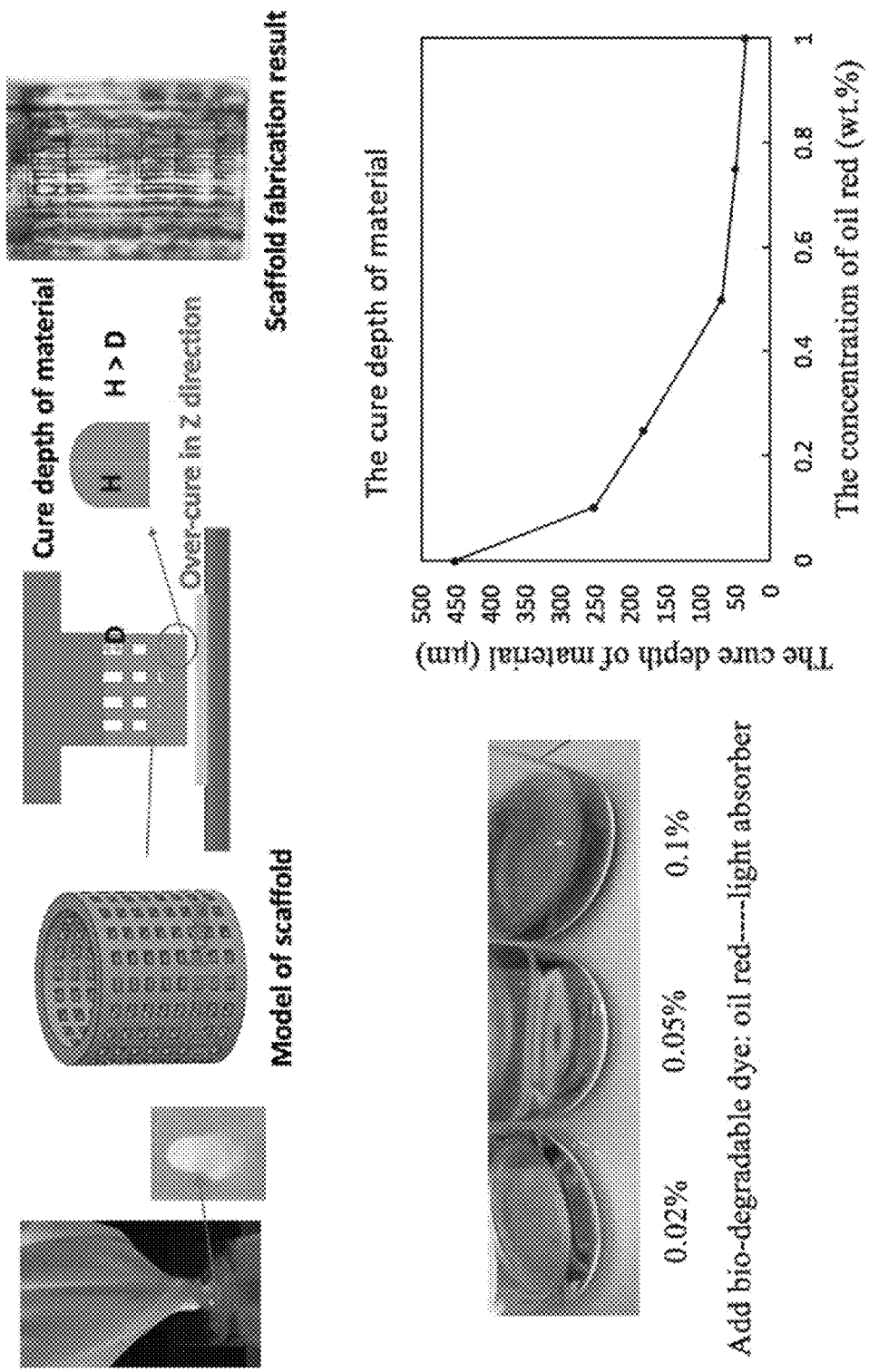
FIG. 31. Cure depth control of PCL-DA based bio degradable photo-curable material.

PCL-DA composite material is transparent, and the cure depth of material is higher than 400 μm (FIG. 31). Since we want to fabricate holes with dimension 80 μm on the scaffold's side wall, when the cure depth of material is bigger than the micro-scale features in fabrication direction, micro-scales will miss due to the over-cure features. To increase fabrication resolution, we reduced the cure depth of PCL based composite material by adding light absorber. We tried different percentage of light absorber ranging from 0.02%, 0.05% and 0.1% and cure depth of PCLDA with different percentage of light absorber ranges from 35 μm to 450 μm (FIG. 31).

The Growth Factor Release

We mixed growth factor inside PCL based photo-curable composite material, and during printing process, growth factor and HA/TCP are blocked inside each cured layer of scaffold. The results are summarized in the following tables.

TABLE 1

The curing property of PCLDA material with and without growth factor.

| Material | Exposure time | Cure depth |
| --- | --- | --- |
| PCL-DA + 0.75 wt % dye | 35 S | 50 μm |
| PCL-DA + 0.75 wt % dye + rh/mlhh(c28II)-N | 39 S | 35 μm |
| PCL-DA + 0.75 wt % dye + rh/m/rBMP-2 | 39 S | 35 μm |

TABLE 2

The curing property of PCL-DA material with different concentration of HA/TCP.

| Material | Exposure time | Cure depth |
| --- | --- | --- |
| PCL-DA + 10 wt % HA/TCP | 26 s | 350 μm |
| PCL-DA + 20 wt % HA/TCP | 29 s | 250 μm |
| PCL-DA + 30 wt % HA/TCP | 30 s | 75 μm |
| PCL-DA + 40 wt % HA/TCP | 32 s | 45 μm |

Figure 32:
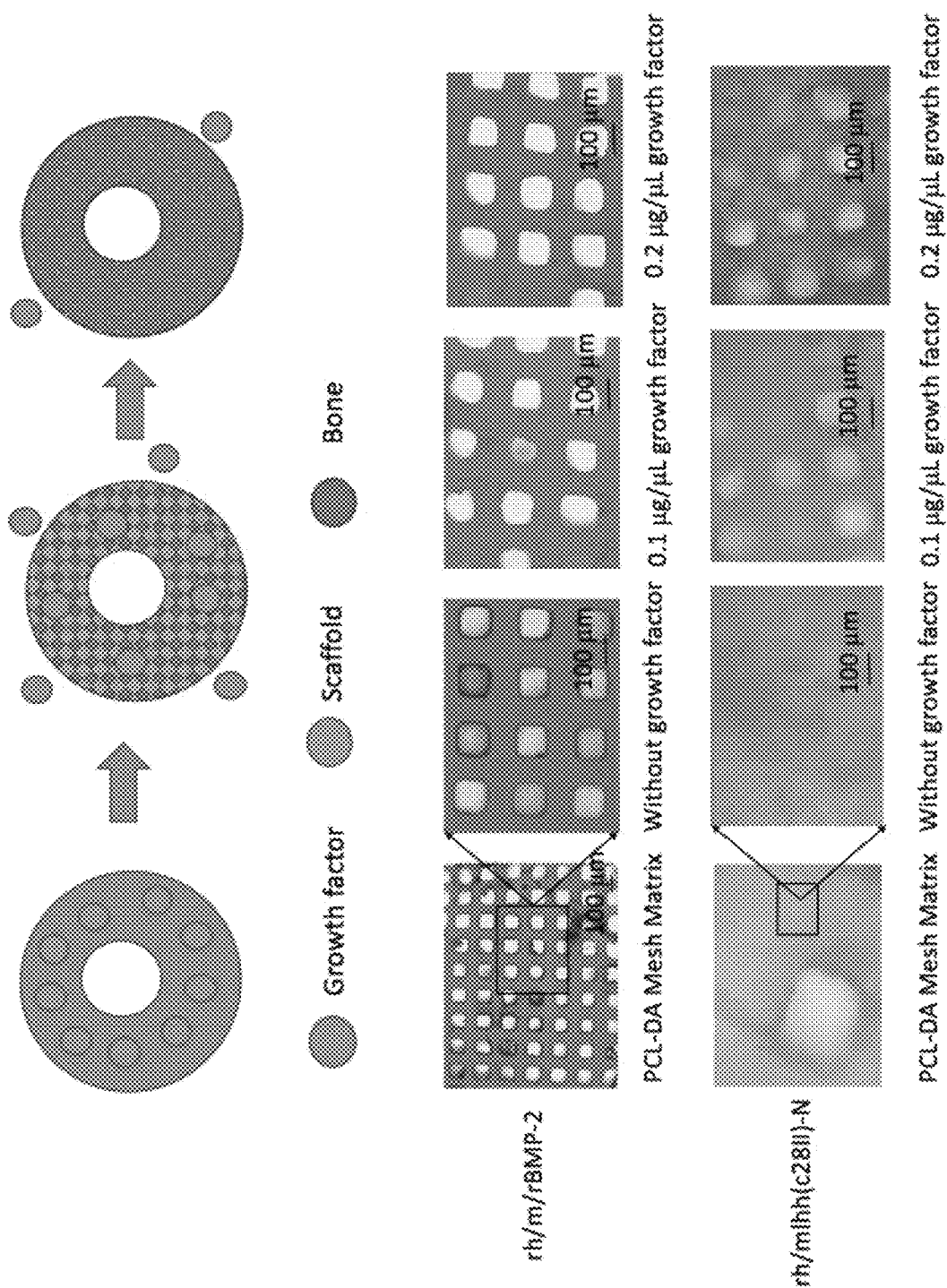
FIG. 32. Growth factor release study with different percentage of growth factor (rh/m/Rbmp-2 and rh/mlhh(c28II)-N).

During the degradation of PCL-DA, growth factor will gradually release from the scaffold we fabricated (refer to FIG. 32). To accelerate the tissue regrowth, we need to study the relation between release speed of growth factor, geometric shape of scaffold structures, and percentage of growth factor of printing material. As shown in FIG. 32(c), we printed 2D matrix scaffold with 0.1 μg/μl and 0.2 μg/μl growth factor respectively to study the release speed of growth factor of PCL based composite with different percentage of growth factor.

Figure 33:
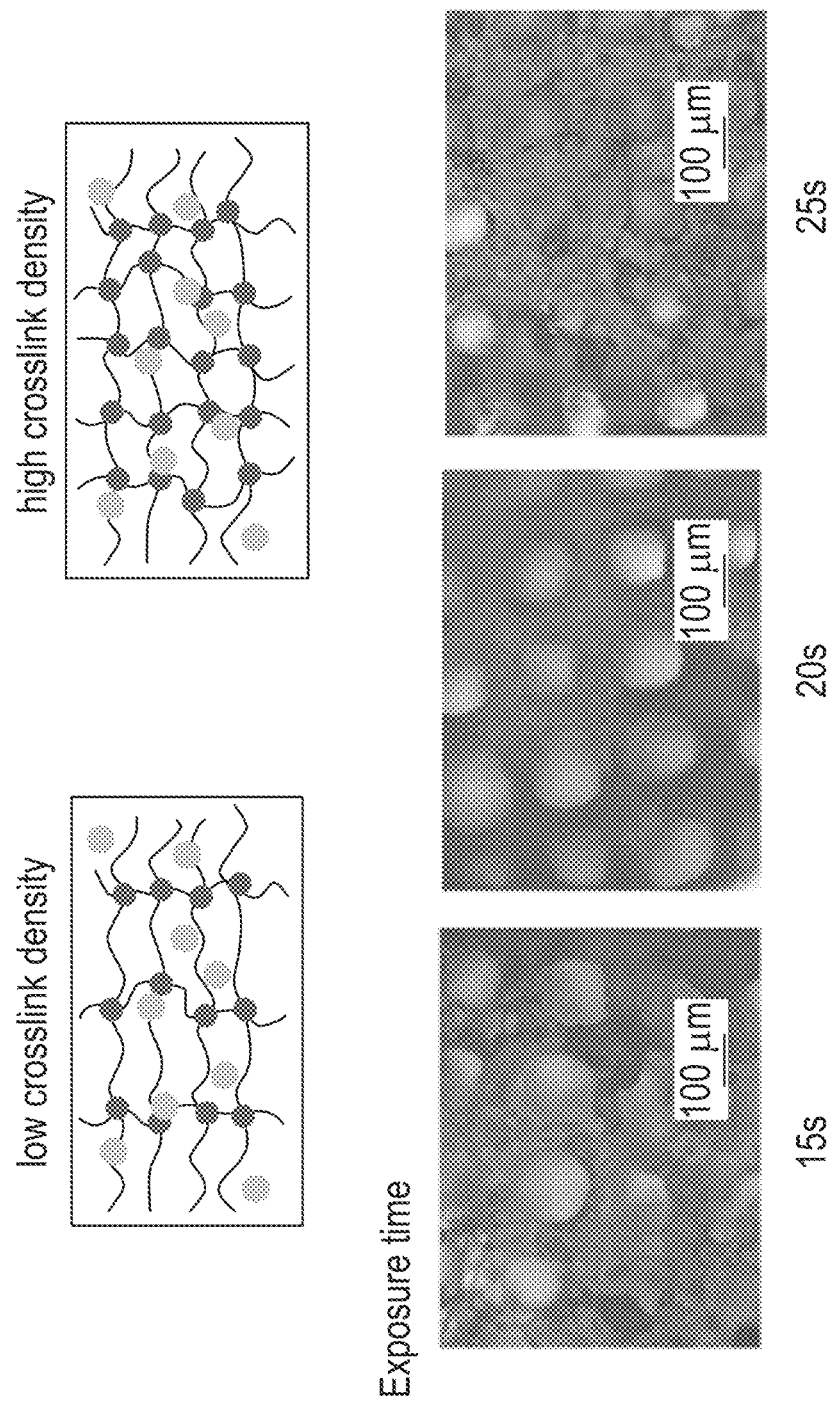
FIG. 33. Growth factor release study with different crosslink density by different exposure time.

The energy which photo-curable polymer received by light exposure, determined the crosslink density of photo-curable polymer. The energy is equal to the product of light intensity and exposure time. The photo-curable polymer received more energy with the increase of exposure time. Because of that, the crosslink density of polymer will also increase with the exposure time. The degradation of polymer depends on the crosslink density. A polymer with lower crosslink density may degrade faster as compared with a polymer with high crosslink density as shown in FIG. 33. To figure out the suitable crosslink level of PCL-DA based composite material, we printed the mesh matrix with 0.1 μg/μL and 0.2 μg/μL of growth factor using different exposure time, ranging from 15 s to 25 s.

The Preliminary Fabrication Result

Figure 34:
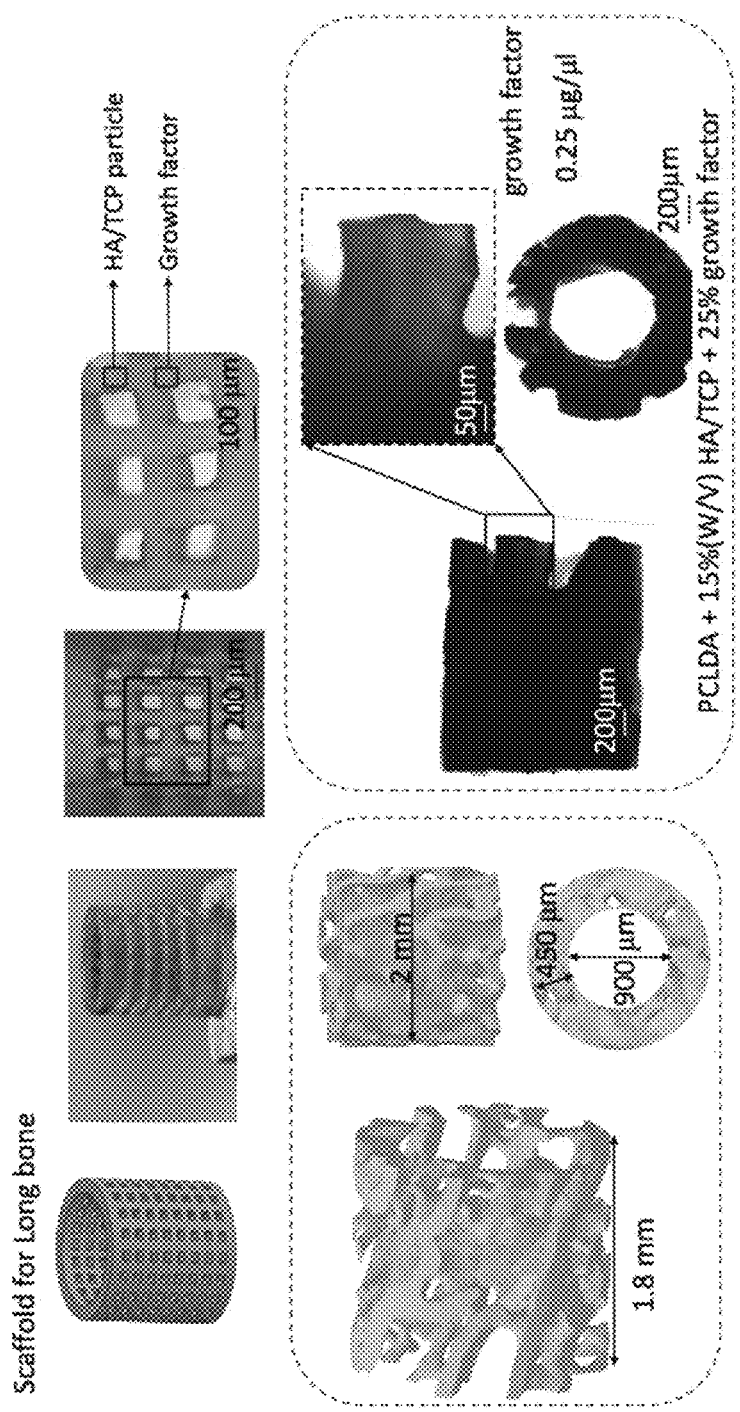
FIG. 34. Micro-scale scaffold fabrication result for long bone regeneration.

We fabricated long bone scaffolds by using micro-scale MIP-SL we developed. FIG. 34 shows the fabrication results of PCL based scaffolds for long bone critical defect regeneration. We imported CAD model into the software, and slice the model with the thickness required. When generating the projection image, the gray scale level was adjusted based on the calibration database. From the microscope image, HA/TCP bone material particle and growth factor were uniformly distributed inside the HA/TCP scaffold.

Figure 35:
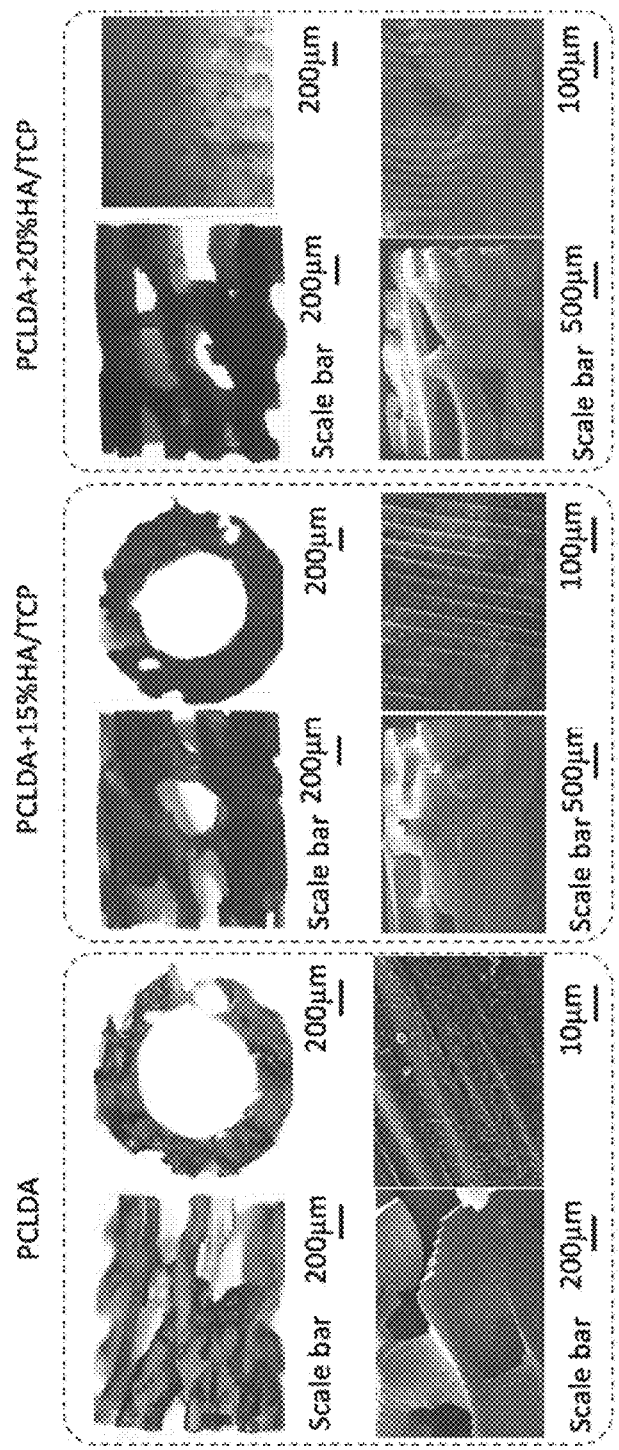
FIG. 35. Micro-scale scaffold fabrication result for long bone regeneration.

We also fabricated PCL based scaffold with different geometric shape. The fabrication results of PCL based scaffold with biomimetic bone structure were shown in FIG. 35. We printed the PCL scaffold with different concentration of HA/TCP particles (15 wt % HA/TCP and 20 wt % HA/TCP), and as confirmed from the SEM image, the particles are uniformly distributed inside the each layer of PCL based scaffold.

In summary, we described scaffold design for the long bone and cranial defect regeneration. To regenerate bone tissues, we figured out the two material solutions: biodegradable material (PCL based composite material) and HA/TCP based suspension. Based on the material property, we further developed appropriate MIP based SLA processes to print scaffold with different inner structures, which achieved the fabrication of scaffold with high resolution complex geometric shape. Ultrasonic-assisted method was applied to uniformly distribute growth factor and HA/TCP particle inside the printed biodegradable PCL based scaffold for long bone healing. The high viscous HA/TCP suspension were formed to the 3D shaped scaffold for cranial defects regeneration.

Figure 36:
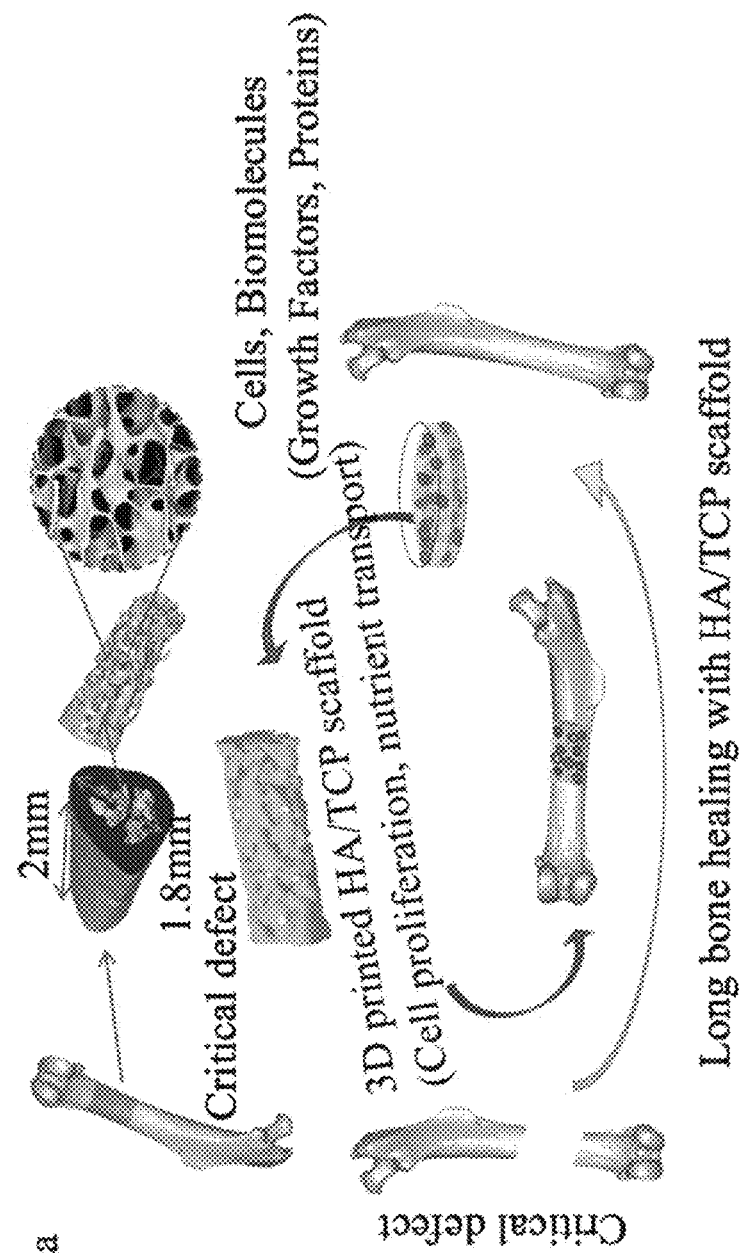
FIG. 36. The Schematic diagram of 3D printed HA/TCP scaffold with hierarchical porous structures for long bone critical defect. (a) Schematic diagram of long bone healing with 3D printed HA/TCP scaffold; (b) schematic diagram of the developed 3D printing process of HA/TCP suspension; (c) the sketch of the micro-scale projection based stereolithography with slurry feeding based on tape casting; (d) 2D patterned curing light beam; (e) biomimetic scaffold model designed for mouse's long bone was sliced into a series of projection images; (f) the microscope image of printed green part of biomimetic HA/TCP scaffold; and (g) the microscope and SEM images of final biomimetic HA/TCP scaffold after sintering process with hierarchical pores.
Figure 36:
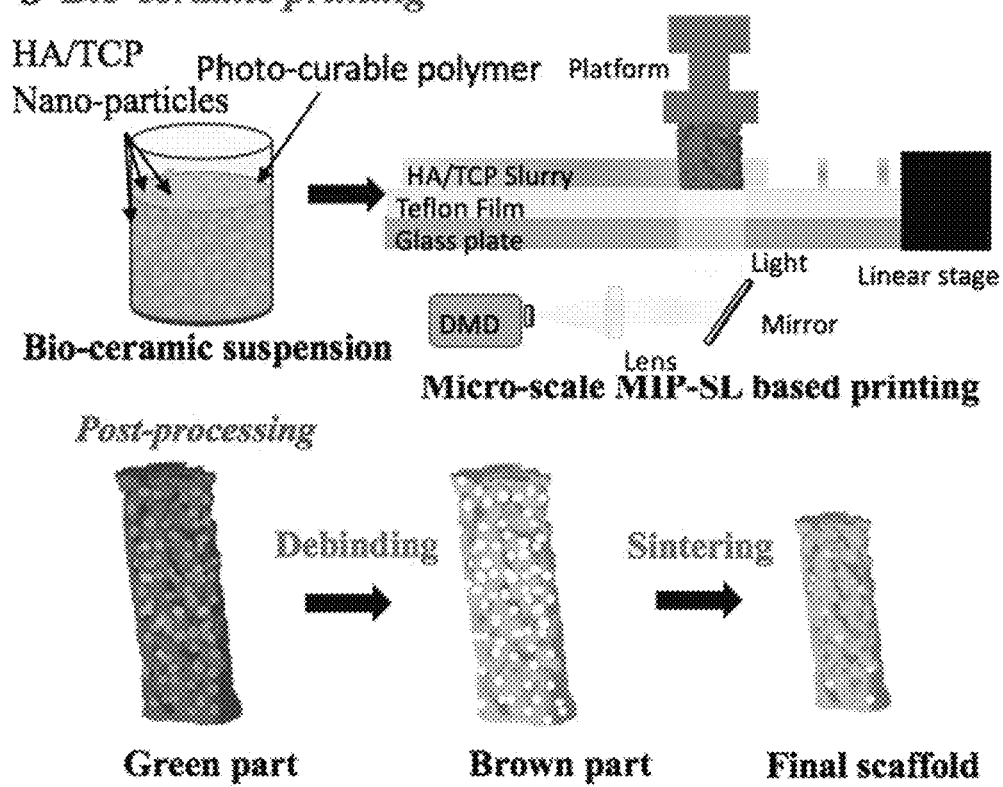

Example 29. 3D Printing of Hydroxyapatite/β-tricalcium Phosphate Scaffold with Hierarchical Porous Structure for Long Bone Critical Defects In this example, we developed a micro-scale MIP-SL process with a special slurry feeding module that allows the fabrication of highly viscous HA/TCP slurry (FIG. 36(b)). The curing performance and physical property of HA/TCP suspension was investigated. With the help of high-resolution optical system and after optimizing process parameters, 30 wt % HA/TCP scaffold with 30 μm pores was successfully fabricated by the 3D printing method. Furthermore, the shrinkage analysis and design compensation of HA/TCP scaffold were conducted to ensure desired dimension after post-processing. Such biomimetic HA/TCP scaffold encompasses hierarchical features ranging from micro-scale porous structure (diameter: ~60-100 μm) to interconnected small pores (<10 μm) induced by polymer burn-out during post processing (refer to FIG. 36(c)-(g)). The biological performances of the 3D printed HA/TCP scaffolds were studied afterwards. From the cell proliferation results, HA/TCP scaffold with hierarchical porous structures was biocompatible and non-toxic, providing a suitable cell culture environment. Scaffolds with 30 wt % HA/TCP were designed for mouse's long bone critical defect model, and then the 30 wt % HA/TCP scaffolds were implanted with CNCCs and BMMSCs. The in vivo result showed favorable bone formation on HA/TCP scaffold, demonstrating such method could present a potential solution to build scaffolds for long bone tissue regeneration.

Example 30. Synthesis of Curable HA/TCP Based Ceramic Slurry

Hydroxyapatite used in this study is in the form of nano-sized powder, of which particle size is smaller than 200 nm (purchased from Sigma-Aldrich), and β-tricalcuim phosphate, one type of micro-sized powder with particle size less than 4 μm (purchased from Sigma-Aldrich). The photo-curable liquid polymer SI500 (purchased from EnvisionTEC Inc) was used as a binder since it can accurately build parts with high feature details. To find out the optimal concentration δ of HA/TCP particle, 10 wt %-40 wt % HA/TCP suspensions were prepared following the following procedures. Firstly, same proportion of HA and TCP powder were poured into the liquid photopolymer resin (SI500). Then the mixed HA/TCP slurry was ball-milled with rotational speed 200 rpm for 40 min. After that, the HA/TCP suspension was degassed in the vacuum before fabrication. In addition, to study how to increase the cure depth of HA/TCP suspension, 0.1 wt %, 0.25 wt %, 0.5 wt %, 0.75 wt % and 1 wt % light absorber (oil red purchased from Sigma-Aldrich) was added to the 30 wt % HA/TCP suspension, respectively, with the rest of the preparation procedures identical.

Example 31. Scaffold Design for Long Bone Regeneration

Figure 40:
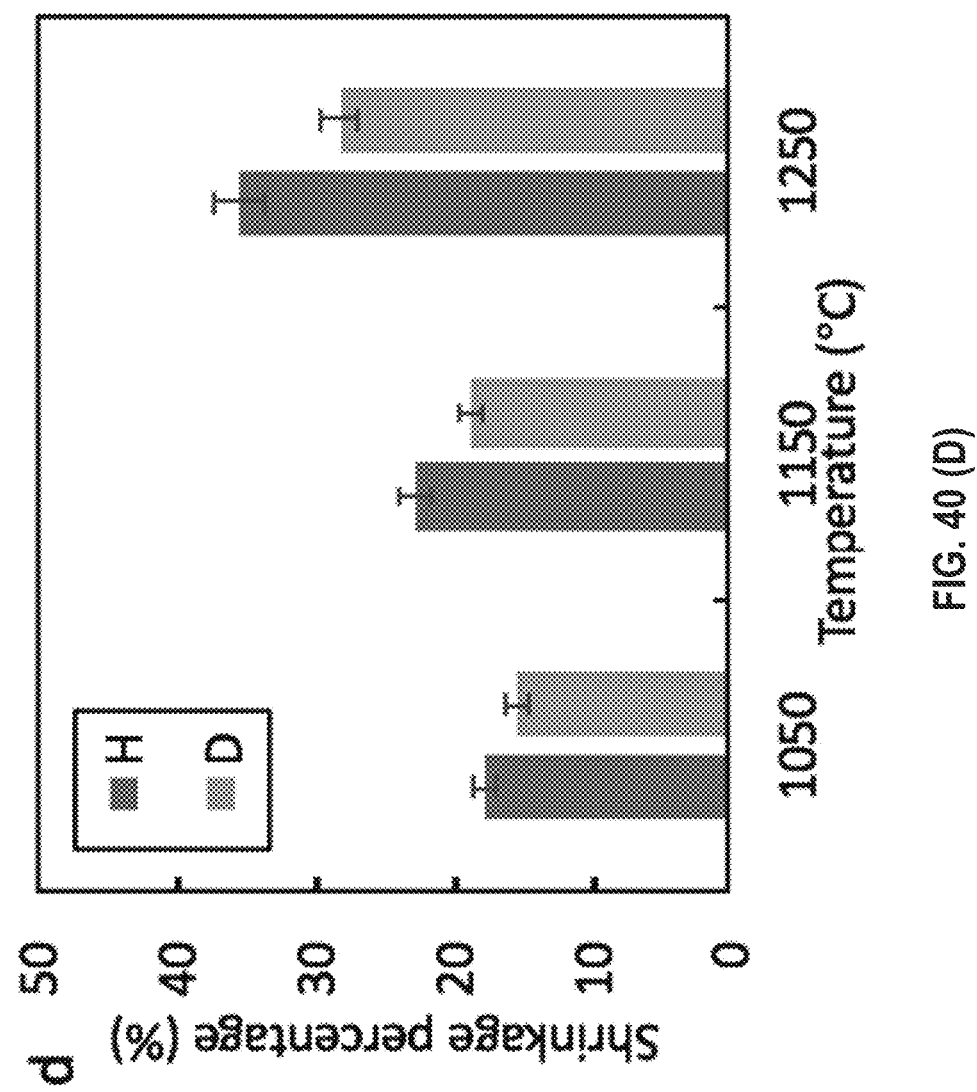
FIG. 40. The shrinkage of HA/TCP scaffold after sintering. (a) The 3D printed scaffolds with 30 wt % HA/TCP and different micro hole designs; (b) the sintered scaffolds with 30 wt % HA/TCP and different micro holes; (c) the microscopy image of HA/TCP scaffolds before and after post-processing; (d) the shrinkage ratio of 30 wt % HA/TCP scaffolds in the Z and XY directions under different sintering conditions; and (e) the shrinkage ratio of HA/TCP scaffold with different concentrations of HA/TCP particles.
Figure 40:
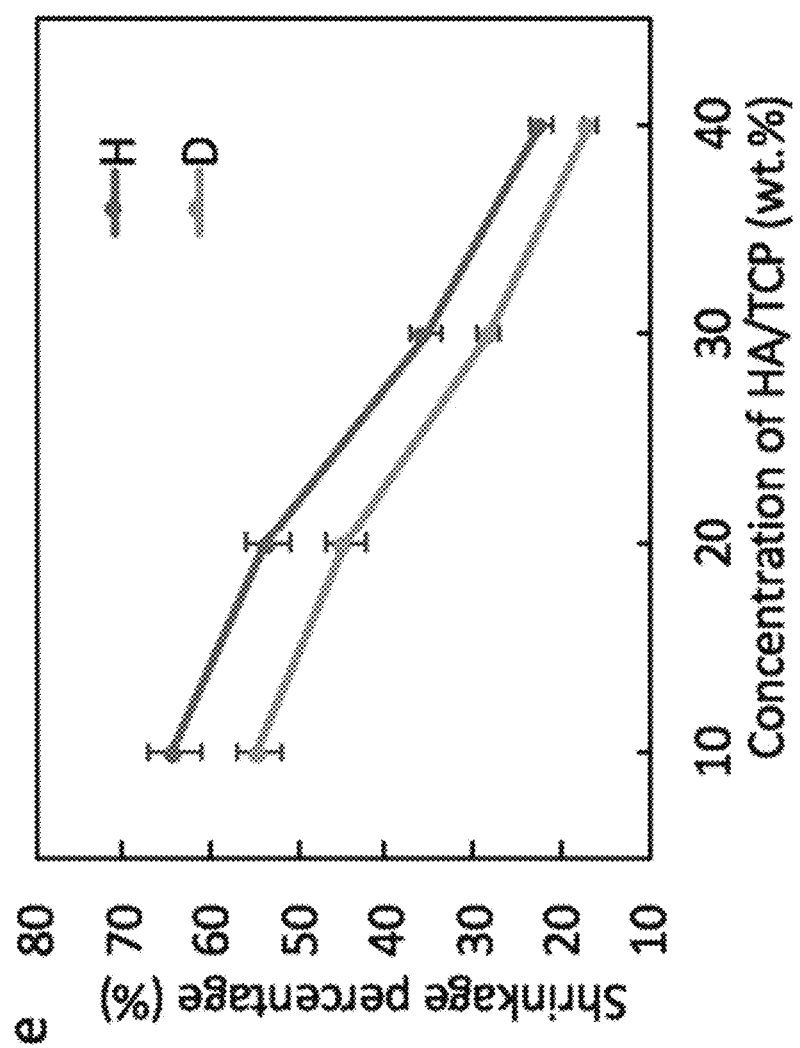

To test the printing capability of the developed process in the X/Y plane and in the Z direction, two groups of 2 mm cylindrical shells were designed as follows. To examine the fabrication precision in the X/Y plane, rectangular pores with 200 µm height and different width from 30 µm to 300 µm were designed on the side wall of the scaffold with 250 µm thickness. To examine the fabrication capability in the Z direction, another scaffold with square pores was designed, with pore heights ranging from 30 um to 350 um (refer to FIG. 41). Meanwhile, scaffolds with 2 mm (height)×1.8 mm (diameter)×250 µm (thickness) were designed at different density (12, 18, 24, and 30 counts of pores), with each of the pores measured within 200 µm to 400 µm edge lengths, in order to study the shrinkage of HA/TCP scaffolds after post-processing (refer to FIG. 40). Also, a solid cube with 2 mm height was designed to analyze the effect of post-processing conditions over mechanical strength and porosity of the sintered HA/TCP scaffolds.

In the case of long bone, soft inner core, commonly being called as bone marrow, is surrounded by hard cortex compact bone matrix (Basu et al.). The bone matrix provides hard mechanical support for bone, and the bone marrow provides sufficient supply of blood and nutrients at the same time. We designed HA/TCP scaffold with hierarchical structures for the regeneration of bone matrix based on the digital CT scanning data of a long bone model of a mouse. The length of the mouse's long bone critical defect was set at 2 mm, at which the bone tissue will not be able to heal by itself (refer to FIG. 36). To increase mechanical stress, 2 mm (height)×0.9 mm (diameter) scaffolds with micro lattice structures and biomimetic bone structures were designed, respectively. Scaffold with lattice spatial-grid structure encompasses micro pores in the range from 50 µm to 150 µm. The diameter of micro-scale porous structure was set at 60 µm to 100 µm for the scaffold comprised of biomimetic bone structures (refer to FIG. 41).

Example 32. Slurry-Based µMIP-SL

Figure 37:
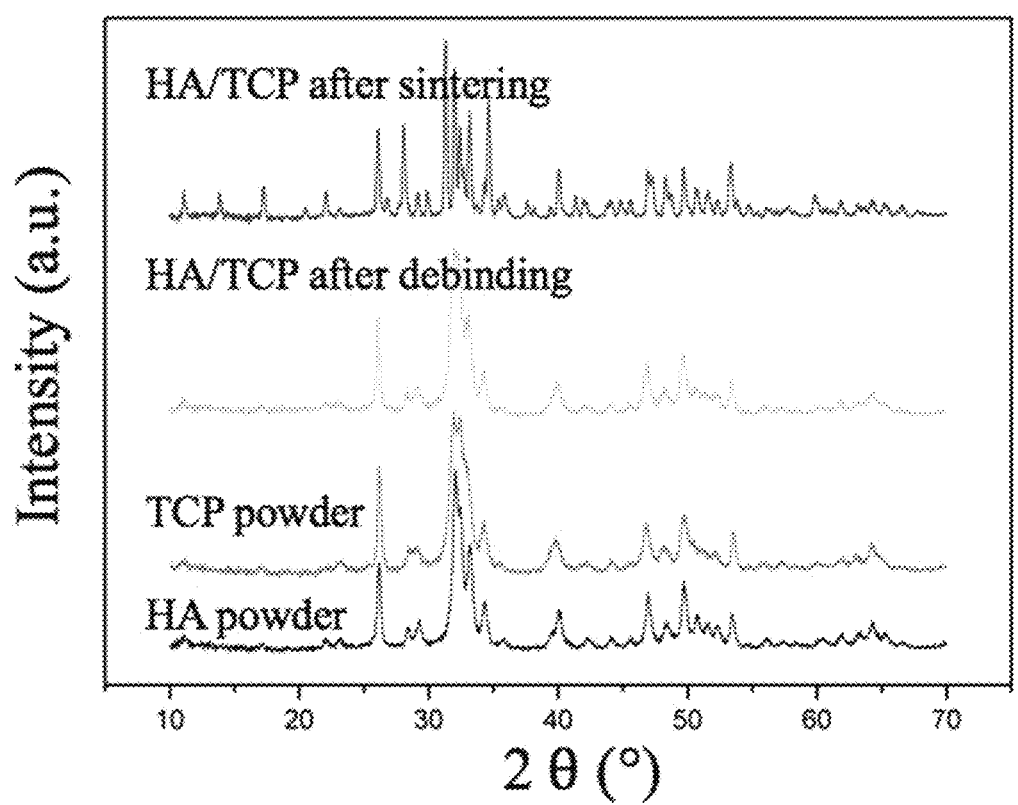
FIG. 37. X-ray diffraction test of 30% HA/TCP scaffold before and after the debinding and sintering processes.

To achieve high-resolution fabrication of HA/TCP scaffolds with hierarchical structures, we developed a micro-scale 3D printing process based on MIP-SL technology (refer to FIG. 37(a)). In our slurry-based µMIP-SL, the light is illuminated and reflected by a Digital Micro-mirror Device (DMD), where millions of micro mirrors are integrated and encapsulated (from Texas instruments, Inc). The light intensity can be altered by tuning the angle of each mirror (Yang, Y. et al., Li et al., Yang, Y. et al, Zhou et al., Li et al., Zhou et al.). To get uniform light distribution, the light is collimated by an achromatic doublets lens (purchased from Thorlabs. Inc), and the collimated parallel light is later focused by 4× objective lens (purchased from Thorlabs Inc.). The ultimate resolution of projection image is 2.5 µm/pixel in our slurry-based µMIP-SL system. To lower the impact of distortion, a filter lens (purchased from Thorlabs Inc.) was used to transmit light at the wavelength of 405 nm, while rejecting other wavelength band of light radiation. A light monitor system, consisted of camera, convex lens and beam splitter, was also designed to monitor the projection light during the 3D printing process (Yang, Y. et al., Li et al.).

Due to high viscosity of HA/TCP suspension, the resin feeding module commonly used in the liquid-based MIP-SL systems cannot be directly applied since the HA/TCP slurry cannot refill the fabrication area spontaneously after each layer processing. To solve the slurry feeding problem, the bottom-up based MIP-SL with auxiliary circular motion with doctor blade was developed (Li et al., Song et al. (2015), Song et al. (2017)). In our prototype system, the projection image irradiated from the bottom of the glass slide was focused at the top surface of the glass plate, where a Teflon film was coated (refer to FIG. 36(b)). Based on the projection system, HA/TCP suspension is cured on the platform after receiving enough energy from the controlled light exposure. The platform was mounted on the linear stage (purchased from AeroTEC Inc.) in the Z direction with the linear motion accuracy of ±1 µm. The glass plate was fixed on a linear stage traversing along the X direction with a fast feeding speed provided for material refilling. A doctor blade was used to recoat the slurry on the glass plate. Note that the layer thickness is smaller than the thickness of the slurry recoated by the doctor blade and can be accurately controlled by the Z stage (Song et al. (2107)).

Example 33. Post-Processing of 3D Printed Scaffold

A green part based on HA/TCP suspension was firstly printed by the slurry-based µMIP-SL process. Afterwards, post-processing procedures consisting of debinding at low temperatures and sintering at high temperatures were used to entirely remove the polymer in the scaffold, and fuse the HA/TCP particles together (refer to FIG. 36(b)). In the debinding process, photopolymer needs to be removed completely, because residual carbon would have significant impacts on the following sintering process, and eventually the biological performance of HA/TCP scaffold. As the temperature increasing from 300° C. to 600° C., the weight of the fabricated green part decreased dramatically. When the temperature reached 600° C., the weight of the green part maintained at a constant value, which is equal to the original weight of HA/TCP particles (Song et al. (2015), Song et al. (2017)). The temperature setting during the debinding process follows the curve shown in to FIG. 26(a). A tube furnace (GSL-1100X-SK purchased from MTI Corp) was used in the debinding process. Note the debinding process should be conducted at a slow heating rate to ensure the decomposition rate of polymer is slower than the pyrolysis rate. Otherwise the green part may be damaged since the gas generated by the pyrolysis process may exceed the threshold. In our study, the heating rate was set at 1° C./min in the vacuum condition. The generated gas was continuously exhausted by the vacuum pump to maintain the pressure of the heating zone at −0.1 mPa. In addition, the temperature was held for 30 minutes for every increment of 100° C. until the temperature reached 600° C. The temperature was then maintained at 600° C. for 180 minutes so that polymer inside the green part of HA/TCP scaffold can be fully removed.

After the debinding process, porous structures are formed at places where polymer is located. Since HA/TCP particles are sparsely arranged, the brown part of HA/TCP scaffold has insufficient strength to support external loads. Therefore, an additional sintering process is necessary in order to fuse HA/TCP particles together to improve the mechanical property of HA/TCP scaffold. Meanwhile, the shrinkage ratio and mechanical strength of HA/TCP scaffold are determined by the sintering temperature, as the sintering temperature has influence on the grain-boundary and volume diffusion of ceramic particles (Griffith et al, Song et al. (2106), Frisch et al.). Three different sintering temperatures (1050° C., 1150° C., 1250° C.) were tested to identify the optimal sintering temperature of HA/TCP scaffold for shrinkage ratio and mechanical stress. The GSL-1500 furnace (purchased from MTI Corp) was used to sinter HA/TCP brown parts in the normal air condition. One of the tested temperature curves used in the sintering process is shown in to FIG. 26(b). Specifically, the temperature was gradually increased to 1080° C. and held there for 30 mins. Afterwards, samples were heated up to the highest temperature (1250° C.) and maintained at the temperature for 180 mins. Finally samples were naturally cooled down to the room temperature before taking out.

Example 34. Characterization of 3D Printed Scaffold

XRD Testing.

To verify the change of composition, structure, and physical properties of HA/TCP scaffold after the debinding and sintering processes, the X-ray diffraction (XRD) test of the fabricated HA/TCP scaffolds was conducted after each step. The comparison of the original HA/TCP particles and the HA/TCP scaffold after each post-processing step is shown in to FIG. 37(c). After the debinding process, the scaffold shows similar integrated intensity as the original HA and TCP particle. However, after the higher temperature sintering process, both the peak counts and the peak values of the HA/TCP scaffolds increase because the crystalline size of HA/TCP particles is larger compared with the original HA/TCP powders.

Mechanical Testing.

Mechanical properties of the post-processed HA/TCP scaffold were studied using the compression machine (Instron 5492 dual column testing systems, Instron, Mass., USA). We built 2 mm×2 mm×2 mm HA/TCP solid cubes for the compression tests and three samples were prepared for each case. The compression test of each specimen was conducted by gradually increasing the load until the sample failed completely. The compressive strength of HA/TCP material was calculated based on the stress-strain curve.

Porosity Testing.

Gravimetric (Archimedes) method was applied to calculate the porosity of the final scaffold after post processing. The scaffold mass $M_d$ in the dry state was firstly measured. The HA/TCP scaffold was then merged into silicon oil and later put into vacuum to completely saturate pores with silicon oil. Following that the mass $M_{sat}$ of scaffold was further measured. Afterwards the scaffold was immersed into the water tank and mass $M_{sub}$ was measured. The porosity of 3D printed scaffold can then be calculated by the following Equation:

$$p\% = \frac{\rho_w(M_{sat} - M_d)}{\rho_{oil}(M_{sat} - M_{sub})} \qquad \text{Equation 1}$$

The porosity of HA/TCP scaffold, fabricated with 20 to 40 wt % concentration of HA/TCP particles, was measured based on the aforementioned method. Furthermore, Image J software was used to calculate the porosity distribution of HA/TCP scaffold by analyzing its scanning electron microscopy (SEM) image under large magnifications. For each case, three samples were tested at the same condition, and the results were averaged.

Example 35. Biocompatibility and Bioactivity

NIH3T3 cells were cultured in Dulbecco's Modified Eagle's Medium with 10% of fetal bovine serum. $1\times10^6$ cells were loaded on the surface of the gel-coated HA/TCP scaffold and incubated at 37° C. Cell viability was observed at different time points using live and dead staining assay following standard protocol. $1\times10^4$ cells were seeded in 96-well plate and allowed for 24 hrs for attachment. Scaffolds with different percentage of HA/TCP were cultured with cells to test their effect on cell proliferation activity. After 48 hrs of co-culture, cell proliferation was measured using MTT assay.

Example 36. In Vivo

Animals.

Male immunocompromised mice at 8-10 weeks old (athymic nude, nu/nu, The Jackson laboratory, Sacramento, Calif.) were used in the present study. All mouse experiments were conducted in accordance with protocols approved by the Department of Animal Resources and the Institutional Animal Care and Use Committee of the University of Southern California, USA.

Mouse Dental Pulp Cell Culture.

The dental pulp mesenchyme from the mandibular incisor of P3.5 mice was separated, minced and digested with solution containing 2 mg/ml collagenase type I (Worthington Biochemical) and 4 mg/ml dispase II (Roche Diagnostics) in PBS for 1 h at 37° C. A single-cell suspension was obtained by passing the cells through a 70 μm strainer (BD Biosciences) and was seeded in 10-cm plate culture dishes (Corning) with α-MEM supplemented with 20% FBS, 2 mm L-glutamine, 55 μm 2-mercaptoethanol, 100 U ml-1 penicillin and 100 μg/ml streptomycin (Life Science Technologies). The culture medium was changed after an initial incubation for 48 h.

Critical-Sized Defect Model.

Animals were placed in ventral recumbency with the left hind limb in extension. An anterolateral approach was used to expose the anterior surface of the femur. Briefly, after a lateral longitudinal cutaneous incision along the femur extending from the hip joint to the stifle joint, the fascia lata was incised to expose the full length of the femur preserving the sciatic nerve caudally and the articular capsule distally. An anterior PEEK microlocking plate (MouseFix plate; RISystem AG, Davos, Switzerland) was applied on the anterior femoral side. Next, four holes were drilled using a 0.3-mm drill bit (Drill bit 0.30 mm; RISystem AG, Davos, Switzerland) through the most proximal and most distal holes of the plate and four self-tapping locking screws (MouseFix screw 2 mm; RISystem AG, Davos, Switzerland) were inserted and locked to secure the plate. Gigli saws (0.22 mm; RISystem AG, Davos, Switzerland) were then inserted, one each in the two slots of the jig (Drill and saw guide; RISystem AG, Davos, Switzerland), and a 2-mm long mid-diaphyseal femoral ostectomy was subsequently performed. The defect was either left empty or filled with the HA/TCP scaffolds tested with or without cells.

Radiographic Analysis, Sample Collection and Histology.

Radiographs were taken every 2 weeks to evaluate the bone union process until 3 month after the surgery. Immediately after euthanasia, all the left femoral bones were excised. All overlaying muscle tissue was carefully removed. The femoral bones were fixed in 4% paraformaldehyde (pH 7.4) for overnight. The plate and screws were removed after paraformaldehyde fixation of the respective tissue specimens. The samples were then decalcified in 10% DEPC-treated EDTA (pH 7.4) for 4 weeks.

Example 37. Statistical Analysis

The statistical analysis theory was applied in all the experimental design and analysis in this study. The statistical computing of experimental data was executed in R software environment. The analysis of variance (ANOVA) was used to find out the significant parameters in each experiment, and all data presented here was with ±standard deviation (SD) (Tabachnick et al.).

Example 38. Curing Performance of HA/TCP Slurry

Nano and micro scale HA/TCP powders were mixed with photocurable polymer, which consists of monomers, oligomers, stabilizers, and photoinitiators, and the mixed slurry can be solidified by the exposure to electromagnetic radiation (Zissi et al, Jacobs et al.). Since the HA/TCP suspension is solidified layer by layer to form 3D shape, the resolution of the curing process in the Z direction is determined by curing depth ($C_d$) that light can penetrate in the HA/TCP suspension. Compared with pure polymer, the additional HA/TCP particles absorb and scatter light inside the HA/TCP suspension. Hence the photosensitivity of HA/TCP suspension is reduced with the increasing concentration of HA/TCP particles. Based on Jacobs and Griffith model (Jacobs et al., Griffith et al.), the cure depth of HA/TCP suspension can be quantitatively represented as the following equation:

$$C_d = k \frac{d}{\tilde{q}} \left(\frac{n_r}{n_p - n_r}\right)^2 \ln\left(\frac{E}{Ec}\right) \qquad \text{Equation 2}$$

where k is constant; d is the average particle size of HA/TCP; $\tilde{q}$ is the scattering efficient value; $n_r$ and $n_p$ are the refractive indexes of pure resin and HA/TCP slurry respectively; E is the projection light energy; and Ec is the critical energy required for the polymerization of material.

Figure 38:
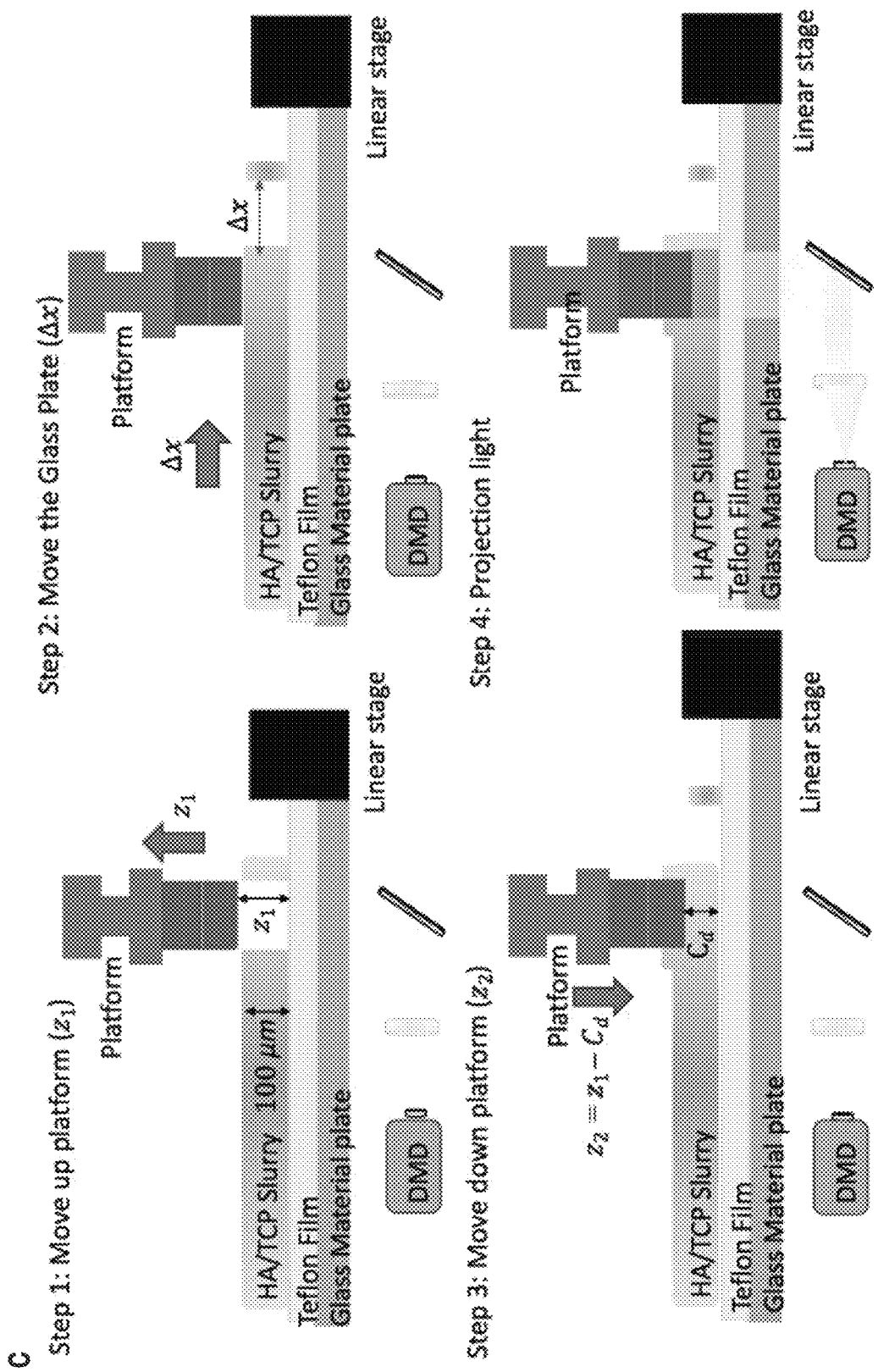
FIG. 38. The fabrication of HA/TCP scaffold using the slurry-based µMIP-SL. (a) The optical system in the slurry-based µMIP-SL system; (b) the hardware design for the circular movement process; (c) the slurry feeding process for the fabrication of highly viscous HA/TCP suspension; (d) the viscosity of HA/TCP suspension with different concentration of HA/TCP particles; (e) the exposure time of HA/TCP suspension with different concentration of light absorber; and (f) the cure depth of HA/TCP suspension with different concentrations of light absorber.
Figure 38:
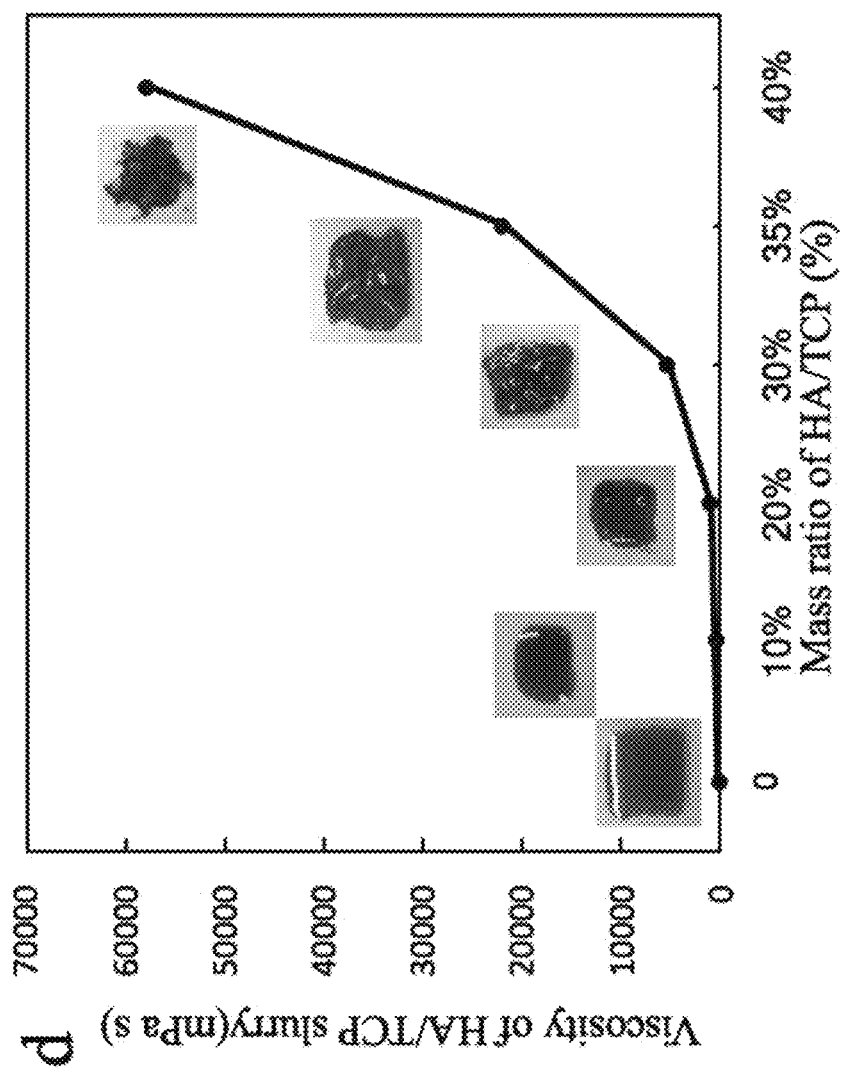
Figure 38:
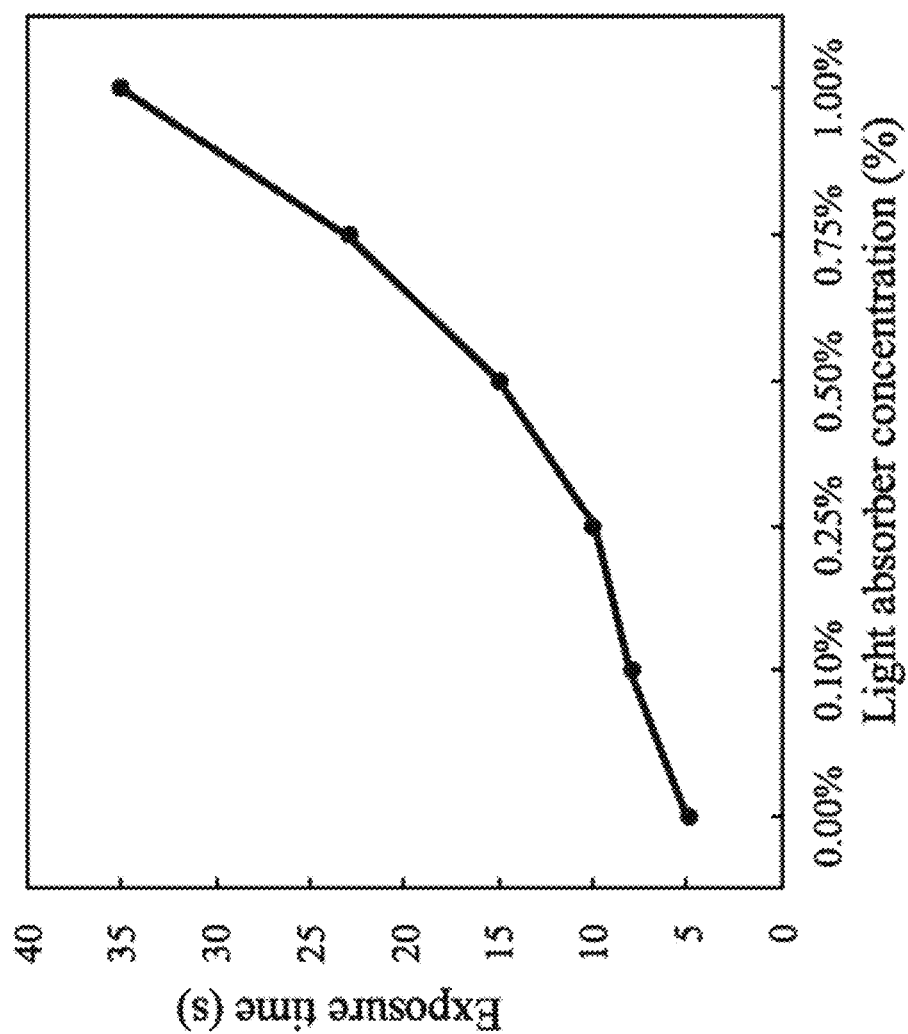
Figure 38:
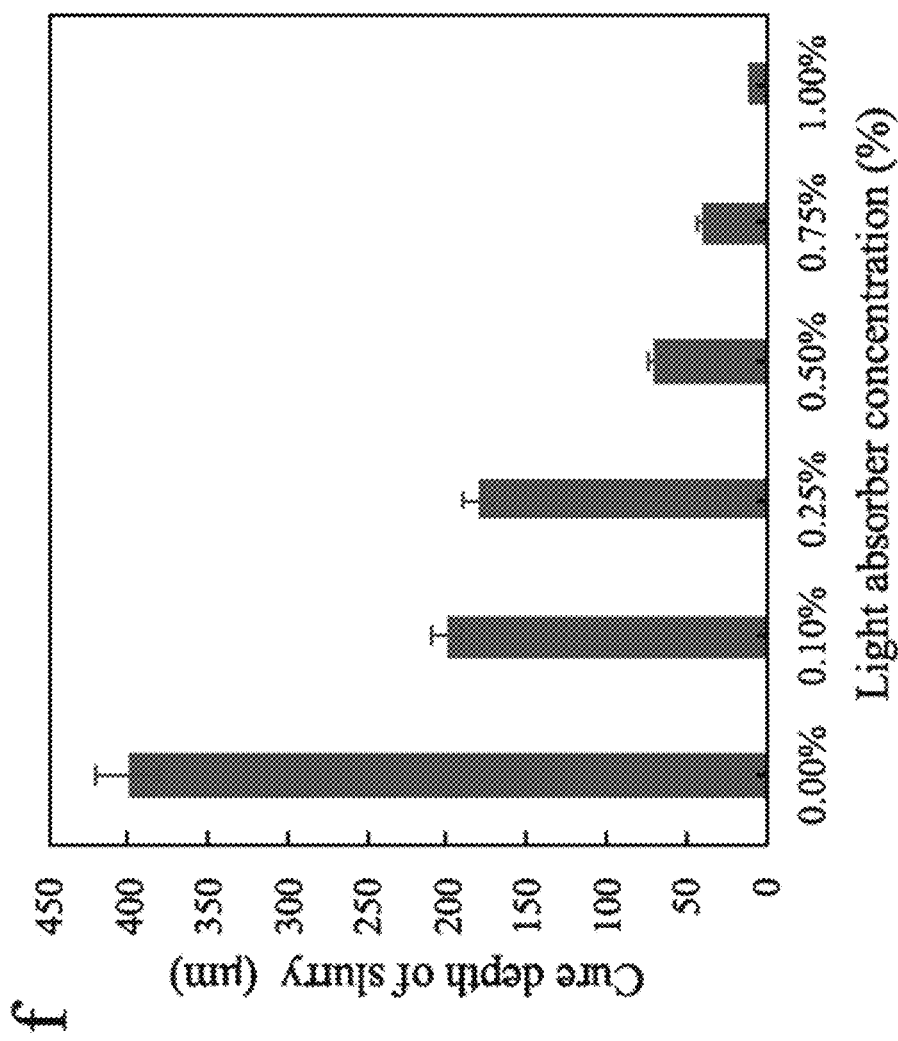

However, although the HA/TCP powders partially block light, the penetration depth of the HA/TCP suspension is still excessively large for micro-scale fabrication. Consequently, projection light not only solidifies the current layer of HA/TCP suspension in the Z direction, but also generates unexpected curing features at the previous layers. A large $C_d$ value brings difficulty in the fabrication of micro pores with dimensions smaller than 100 μm in the Z direction. To reduce the light penetration depth of HA/TCP suspension, different percentages of light absorber were added into 30% HA/TCP suspension, and the cure depth of each group is shown in to FIG. 38(f) and the table below.

TABLE 3

The effect of suspension concentration and the exposure time on the cure depth.

| Suspension Concentration | Exposure time(s) | Cure depth (μm) |
| --- | --- | --- |
| 15 wt % HA + 15 wt % TCP + 0 wt % oil red | 5 | 400 |
| 15 wt % HA + 15 wt % TCP + 0.1 wt % | 8 | 200 |
| 15 wt % HA + 15 wt % TCP + 0.25 wt % oil red | 10 | 180 |
| 15 wt % HA + 15 wt % TCP + 0.50 wt % oil red | 15 | 70 |
| 15 wt % HA + 15 wt % TCP + 0.75 wt % oil red | 23 | 40 |
| 15 wt % HA + 15 wt % TCP + 1 wt % oil red | 35 | 10 |

According to Bear's law, the light penetration depth of photo-curable material is inversely proportional to the percentage $P_d$ of light absorber (Li et al., Yang, Y. et al., Frisch et al.). After adding 1 wt % light absorber, the cure depth of 30 wt % HA/TCP suspension is reduced from 400 μm to only 20 μm. The cure depth Cd of HA/TCP suspension with light absorber can be represented as following Equation:

$$C_d = k' \frac{d}{P_d \tilde{q}} \left(\frac{n_r}{n_p - n_r}\right)^2 \ln\left(\frac{E}{Ec}\right) \qquad \text{Equation 3}$$

Meanwhile, the exposure time t is changed with the increase of light absorber concentration. Since the projection light energy E is the product of exposure time t and light intensity I, the exposure time t can be modified as:

$$t = \left(\frac{E_C}{I}\right) \exp\left(\frac{C_d P_d \tilde{q}(n_p - n_r)^2}{k' d n_r^2}\right) \qquad \text{Equation 4}$$

The exposure time increases exponentially as the growth of light absorber concentration (refer to FIG. 38(e)). It only takes 5 s to cure one layer of pure 30 wt % HA/TCP suspension, while it requires 35 s to cure one layer of 30 wt % HA/TCP with 1 wt % light absorber.

Example 39. Fabrication of HA/TCP Scaffold Via the Slurry-Based μMIP-SL

A green part of HA/TCP scaffold needs to be firstly fabricated based on the scaffold's computer-aided design (CAD) model (FIG. 36(b)). A slurry-based μMIP-SL process was used to selective cure the HA/TCP suspension into complex shape with hierarchical porous structures. In the slurry-based μMIP-SL process, thin layers of HA/TCP suspension are cured after sufficient exposure to focused light beam controlled by high-resolution projection images (FIG. 38(c)). Accordingly, the CAD model of 3D scaffold is sliced into a set of mask projection image with the slicing thickness smaller than the cure depth of HA/TCP suspension [35]. In order to achieve uniformed light intensity, the grayscale level of each pixel in the projection image needs to be adjusted based on a light intensity calibration database (refer to FIG. 36(e)) (Li et al., Yang, Y. et al., Zhou et al.).

In the bottom-up based micro MIP-SL process, the newly cured material is attached on the platform, and the bottom surface of the cured part is parallel to the surface of the glass plate coated with Teflon film. As the platform moving up, a gap between the platform and the glass plate is generated and liquid resin or slurry can flow into it if the viscosity is low. Driven by air pressure and self-gravity, photocurable material would flow back and refill the projection area. Since the material is incompressible liquid flow, and the viscosity of material is not subject to change in the filling process, the self-filling material satisfies the Navier-stokes momentum equation as following (Frisch et al.):

$$\frac{\partial(\rho v_i)}{\partial t} + \frac{\partial(\rho v_i v_j)}{\partial x_i} = -\frac{\partial P}{\partial x_i} + \frac{\partial}{\partial x_j}\left(\mu\left(\frac{\partial v_i}{\partial x_j} + \frac{\partial v_j}{3\partial x_i}\right)\right) \quad \text{Equation 5}$$

where P, v, ρ, μ is pressure, velocity, density, and viscosity of material, respectively.

Based on Eq. 5, the refilling speed v of material is subjected to its viscosity μ and pressure P. The viscosity of HA/TCP suspension exponentially grows as the increase of HA/TCP concentration (See in FIG. 38($d$)). The effect of HA/TCP concentration of the suspension on the viscosity of the suspension is shown in the following table.

TABLE 4

The effect of HA/TCP concentration of the suspension on the viscosity of the suspension.

| HA/TCP concentration of the Suspension | Viscosity of the Suspension |
|---|---|
| 0 | 180 cP |
| 5 wt % HA + 5 wt % TCP | 612.5 cP |
| 10 wt % HA + 10 wt % TCP | 1125 cP |
| 15 wt % HA + 15 wt % TCP | 5375 cP |
| 12.5 wt % HA + 12.5 wt % TCP | 22000 cP |
| 20 wt % HA + 20 wt % TCP | 57812 cP |

When the concentration of HA/TCP particles is smaller than 25 wt %, the HA/TCP suspension is still able to refill the fabrication area during the movement of the Z platform. Therefore, HA/TCP suspension, of which the HA/TCP concertation is from 0 to 25 wt %, can still be 3D printed with self-filling material using the traditional layer-based SL approach, where the platform directly moves up with certain distance after one layer curing. However, when the concentration of HA/TCP particles is higher than 25 wt %, the viscosity of HA/TCP suspension dramatically increases from hundreds of cPa to tens of thousands of cPa. The increased viscous resistance of HA/TCP suspension dramatically obstructs the material flow between the platform and the glass plate. Thus, the HA/TCP suspension, with particles concentration larger than 25 wt %, cannot refill the fabricate area if the flow is only driven by the air pressure and self-gravity.

To solve the refilling issue of HA/TCP suspension with HA/TCP particle concentration larger than 25 wt %, an automatic material feeding module with circular movement was integrated in the slurry-based μMIP-SL. Firstly, a thin layer of HA/TCP suspension at the thickness of 100 μm, was evenly recoated on the top surface of glass plate by using a doctor blade (refer to FIG. 36($c$) and FIG. 36($b$)). After curing one layer of HA/TCP suspension, the platform was firstly raised up by a distance that is larger than the thickness of the recoated HA/TCP layer; and meanwhile the glass plate coated with HA/TCP suspension is moved in the X direction (FIG. 38($c$)). Note the relative position of the projection light and the building platform remains unchanged. After the glass plate's movement in the X direction, a fresh layer of recoated HA/TCP suspension is transported to the light projection place. The platform is then slowly moved down until the distance between the pre-cured part surface and the glass plate is equal to the layer thickness set based on the cure depth of the slurry. With the aforementioned circular movement, a new layer of HA/TCP suspension is constantly fed to the location right below the platform within several seconds. During the building process, the circular movement is repeated until all the layers of the green part have been built on the platform Example 40. Porosity and Mechanical Performance The debinding and sintering procedures are conducted after the green part has been printed by the slurry-based μMIP-SL process. In the debinding process, photopolymer in the green part is removed after raising temperature to 600° C. and the brown part of HA/TCP scaffold is obtained. At this stage, the porosity ratio of HA/TCP scaffold reaches peak value. However, the brown part of HA/TCP scaffold is fragile due to loose arrangements of HA/TCP particles (refer to FIG. 39($a$)); hence the sinterting process is followed to improve bonding between HA/TCP particles.

Three different sintering temperatures (1050° C., 1150° C., 1250° C.) were tested in order to identify an appropriate sintering temperature and concentration of HA/TCP particles. Effects of sintering temperature $T_S$ and HA/TCP particles concentration S over the porosity and mechanical performance of scaffold were summarized in the following tables.

TABLE 5

The effect of the sintering temperature and HA/TCP concentration of the suspension on the mechanical (compressive) strength of the scaffold.

| Temperature | 10 wt % HA + 10 wt % TCP | 15 wt % HA + 15 wt % TCP | 20 wt % HA + 20 wt % TCP |
|---|---|---|---|
| 1050° C. | 0.01 MPa | 0.1367 MPa | 0.172 MPa |
| 1150° C. | 0.073 MPa | 0.46 MPa | 5.228 MPa |
| 1250° C. | 1.18 MPa | 4.32 MPa | 6.35 MPa |

TABLE 6

The effect of the suspension concentration and the sintering temperature on the porosity of the scaffold.

| Suspension Concentration | 1050° C. | 1150° C. | 1250° C. |
|---|---|---|---|
| 10 wt % HA + 10 wt % TCP | 27% | 23% | 20% |
| 15 wt % HA + 15 wt % TCP | 20.5% | 17.3% | 14.6% |
| 20 wt % HA + 20 wt % TCP | 10.4% | 8.7% | 5.9% |

Figure 39:
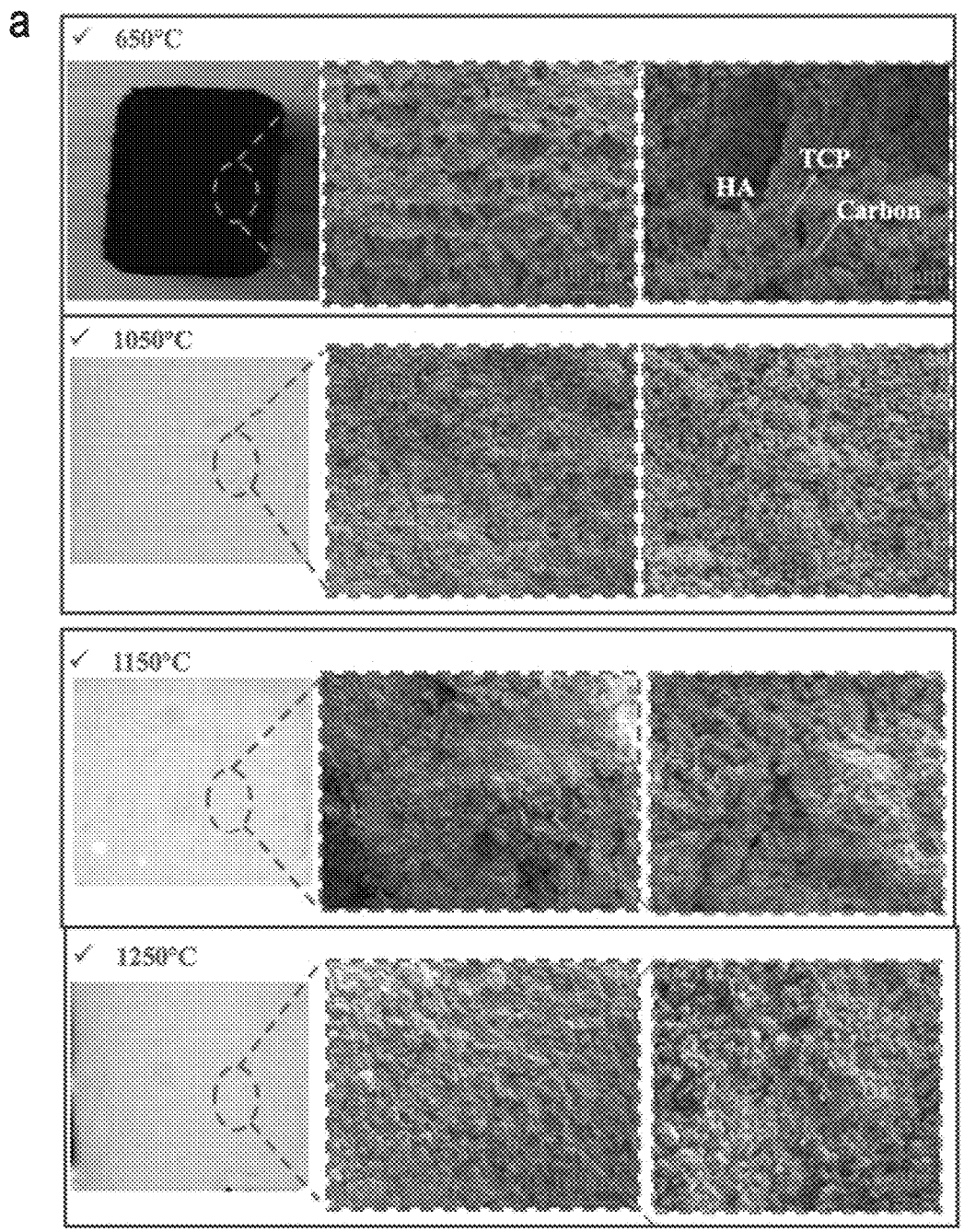
FIG. 39. The porosity and mechanical performance of HA/TCP scaffold sintered at different conditions. (a) The optical microscopic and SEM images of 30 wt % HA/TCP scaffold after post-processing under different temperatures; (b) the compressive strength of HA/TCP scaffold fabricated under different conditions; (c) the porosity of HA/TCP scaffold fabricated under different conditions; and (d) the optical microscope and SEM images of 30 wt % HA/TCP scaffold sintered at 1250° C.
Figure 39:
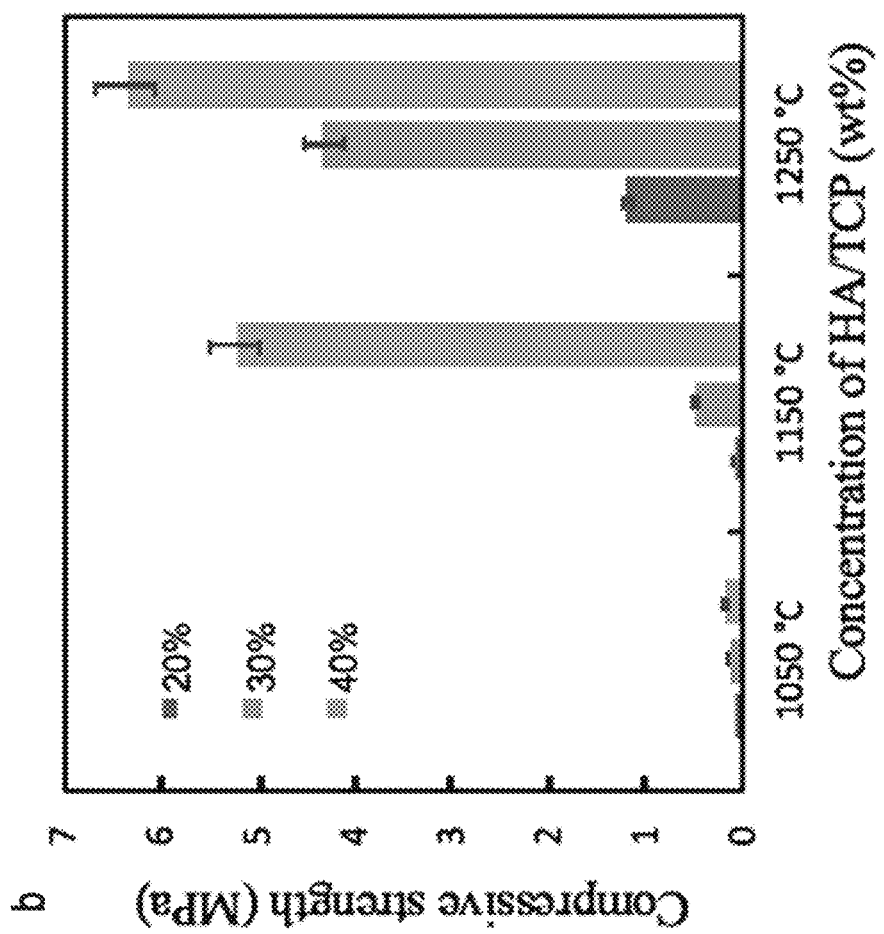
Figure 39:
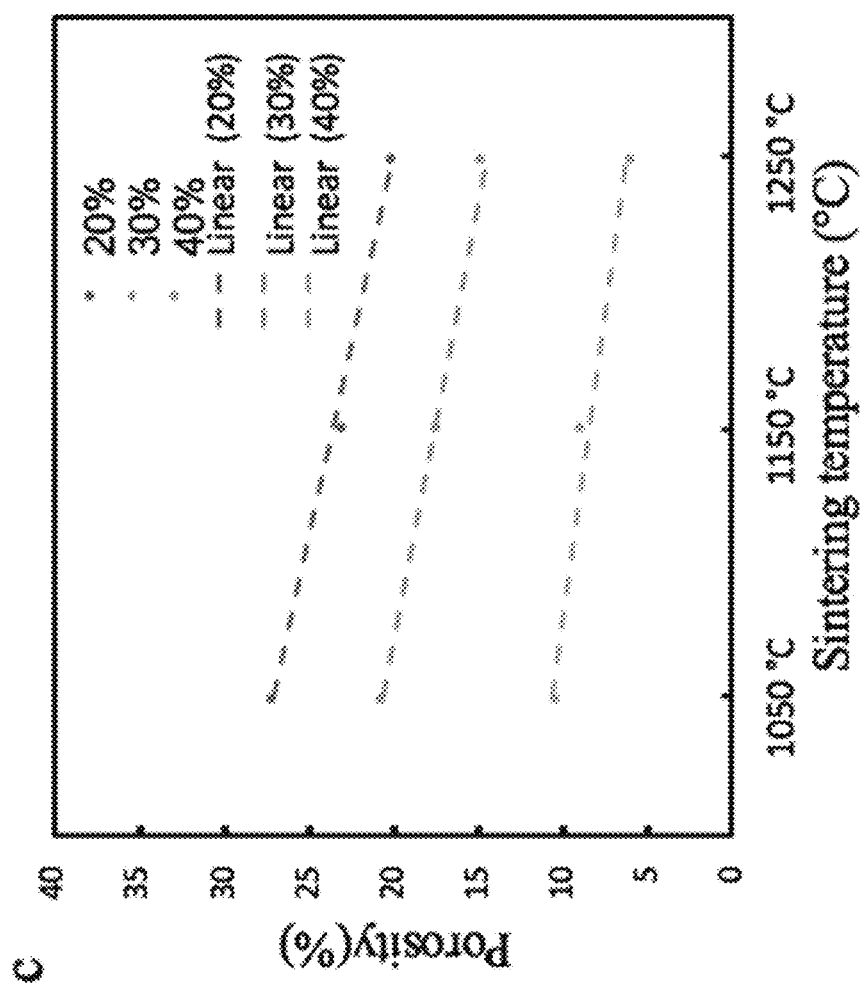
Figure 39:
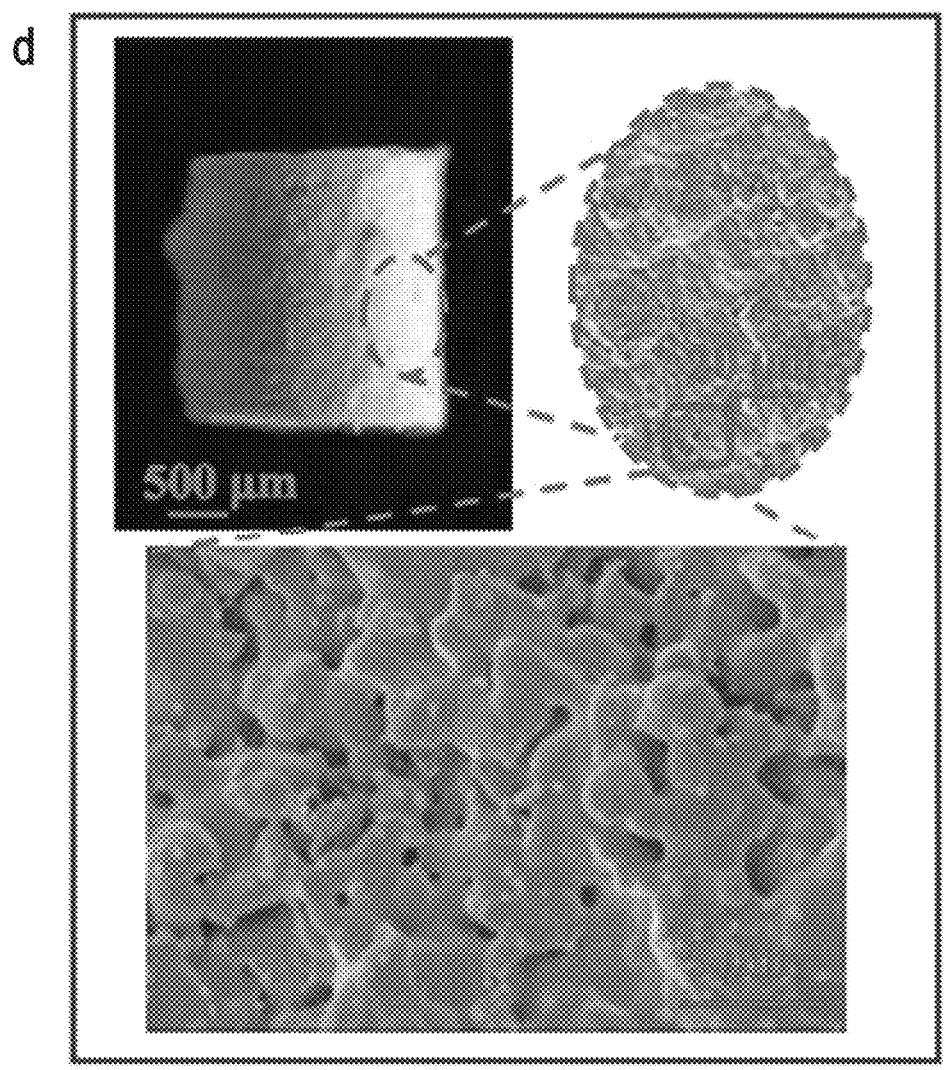

The porosity of HA/TCP scaffold is determined by the particle size 4), sintering temperature T, and the concentration of particle S (Deng et al., Jordan et al.). The porosity p of HA/TCP scaffold decreases linearly with the increase of sintering temperature (FIG. 39). For instance, the porosity p of 30 wt % HA/TCP scaffold is reduced by 6%, when the sintering temperature is raised from 1050° C. to 1250° C. Compared with sintering temperature T, the concentration of HA/TCP particles δ shows more significant impact on the porosity (FIG. 39($c$)). According to the result of pore size distribution, the pore size of the sintered HA/TCP scaffold is mainly in the range of nano-scale (FIG. 39($d$)). This is because the increase of main grain size of HA/TCP particles further reduces the space between each grain after sintering, and the grain of HA/TCP particle grows much larger at a higher temperature.

Meanwhile, the porosity p of HA/TCP scaffold is a significant factor that affects the mechanical performance of HA/TCP scaffold, and the mechanical strength can be expressed as below (Rice et al.):

$$\sigma = \sigma_0 \exp(-ap) \qquad \text{Equation 6}$$

where σ is strength of HA/TCP scaffold, $\sigma_0$ is the strength of fully HA/TCP without pores, and a is constant.

Although the porosity p of 20 wt % HA/TCP scaffold sintered at 1050° C. is at the largest, its mechanical strength is too weak to support compression load from the two sides of the bone. The compressive strength of HA/TCP scaffold can be improved by raising the sintering temperature T or increasing the particles concentration δ of HA/TCP suspension. For instance, the compressive strength of 30 wt % HA/TCP increases from 0.13 mPa to 4.32 mPa, when the sintering temperature is raised up from 1050° C. to 1250° C. Besides, the compressive strength of 20 wt % HA/TCP sintered at 1250° C. improves 5 times when the concentration of HA/TCP is increased from 20 wt % to 40 wt % (refer to FIG. 39(b)). Overall, 30 wt % HA/TCP scaffold sintered at 1250° C. showed advantages over other scaffolds when considering both porosity and mechanical performance.

However, for scaffolds made from 30 wt % HA/TCP, the pores are small after sintering at 1250° C. As shown in FIG. 39(d), the average pore size of 30 wt % HA/TCP scaffold sintered at 1250° C. is smaller than 5 μm. Even though the mechanical strength is acceptable, the nutrient and blood vessels are hard to pass through such dense HA/TCP scaffold. Note the porosity of scaffold plays an essential role in bone formation. The pore size directly correlates to the nutrient and oxygen diffusion and cell integration.

Example 41. Shrinkage Analysis

The shrinkage rates of the scaffolds after the sintering process are summarized in the following tables.

TABLE 7

The effect of the sintering temperature on the shrinkage of the scaffold in axial and radial directions.

| Temperature | Axial direction | Radial direction |
|---|---|---|
| 1050° C. | 17.75% | 15.45% |
| 1150° C. | 22.68% | 18.72% |
| 1250° C. | 35.5% | 28.19% |

TABLE 8

The effect of the suspension concentration on the the shrinkage of the scaffold in axial and radial directions at the sintering temperature of 1250° C.

| 1250° C. | Axial direction | Radial direction |
|---|---|---|
| 5 wt % HA + 5 wt % TCP | 64.06 | 54.4 |
| 10 wt % HA + 10 wt % TCP | 53.4 | 44.7 |
| 15 wt % HA + 15 wt % TCP | 35.5 | 28.19 |
| 20 wt % HA + 20 wt % TCP | 22.22 | 16.67 |

Since photocurable polymer is removed and HA/TCP particles are sintered together in post-processing, the total volume of the sintered HA/TCP scaffold is reduced from the green part fabricated by the μMIP-SL process. As shown in FIG. 40(c), the shrinkage in the Z direction ($r_{sz}$) and in the XY plane ($r_{sr}$) can be calculated, respectively:

$$\begin{cases} r_{sz} = \dfrac{H - H_s}{H} \\ r_{sr} = \dfrac{D - D_s}{D} \end{cases} \qquad \text{Equation 7}$$

The shrinkage ratio $r_s$ is closely related to the concentration of HA/TCP particles δ and the sintering temperature T (Heunisch et al., Boccaccini et al.). The shrinkage ratio $r_s$ of HA/TCP scaffold increases as the concentration of HA/TCP particles decreases as more internal polymer would be burned off (refer to FIG. 40(e)). Hence, With the concentration of HA/TCP particles ramping up from 10 wt % to 40 wt %, the axial shrinkage ratio $r_{sz}$ of HA/TCP scaffold sintered at 1150° C. declined from 45.25% to 17.8%. The same tendency can be observed when the sintering temperature T is increased (refer to FIG. 40(d)). This happens as the diffusion takes place with the increase of sintering temperature, and HA/TCP particles become closer to each other (Boccaccini et al., Hollister et al.). For example, 30 wt % HA/TCP scaffold sintered at 1050° C. shrinks only 17.75% in axial (Z) direction, but 30 wt % HA/TCP scaffold reduces 35.5% when the sintering temperature is increased to 1250° C.

The shrinkage ratio $r_s$ of HA/TCP scaffold is also affected by the geometric design. 30 wt % HA/TCP scaffolds with different densities of micro holes were fabricated as shown in FIG. 40(a)-(b). The volumetric shrinkage of HA/TCP scaffold is less when the scaffold is designed with larger density of micro holes. Furthermore, the shrinkage ratio $r_s$ of HA/TCP scaffold varies in the axial (Z) and radial (XY) directions. As shown in FIG. 40(d)-(e), the shrinkage ratio $r_{sz}$ in the axial direction is bigger than the shrinkage ratio $r_{sr}$ in the radial direction. Specifically, HA/TCP scaffold made by 30 wt % HA/TCP suspension reduces from 2 mm to only 1.29 mm in the axial direction after it was sintered at 1250° C., while the diameter of the scaffold just shrinks to 71.8% of the original value. This is because the part volume in the axial direction is more than that in the radial direction. Furthermore, the HA/TCP suspension is uniformly solidified under the light exposure in the XY direction, hence the stress is more isotropic in the radial plane. In contrast, the HA/TCP suspension is stacked layer by layer in the Z direction; hence the stress in the Z direction is not identical to that in the XY plane. Thus, the 3D printed HA/TCP scaffold shows anisotropic shrinkage behaviors.

Example 42. Complex Scaffold Fabrication with Hierarchical Porous Structures

As discussed above, HA/TCP scaffold presents shrinkage in both axial and radial directions after the sintering process. To achieve accurate shape control in the fabrication of HA/TCP scaffolds with micro-scale pores, the dimensional offset of an input CAD model needs to be applied in order to compensate for the fabrication shrinkage (Xu et al. 2017). Firstly, a series of rectangular, with 200 μm height and varying widths from 30 μm to 300 μm, were printed using 30 wt % HA/TCP suspension. The 3D printed parts and the sintered parts are shown in FIG. 41(a). After measuring the shape changing rate of the micro pores in the XY plane, the compensation factor $\varnothing_{xy}$ in the XY direction was obtained.

Figure 41:
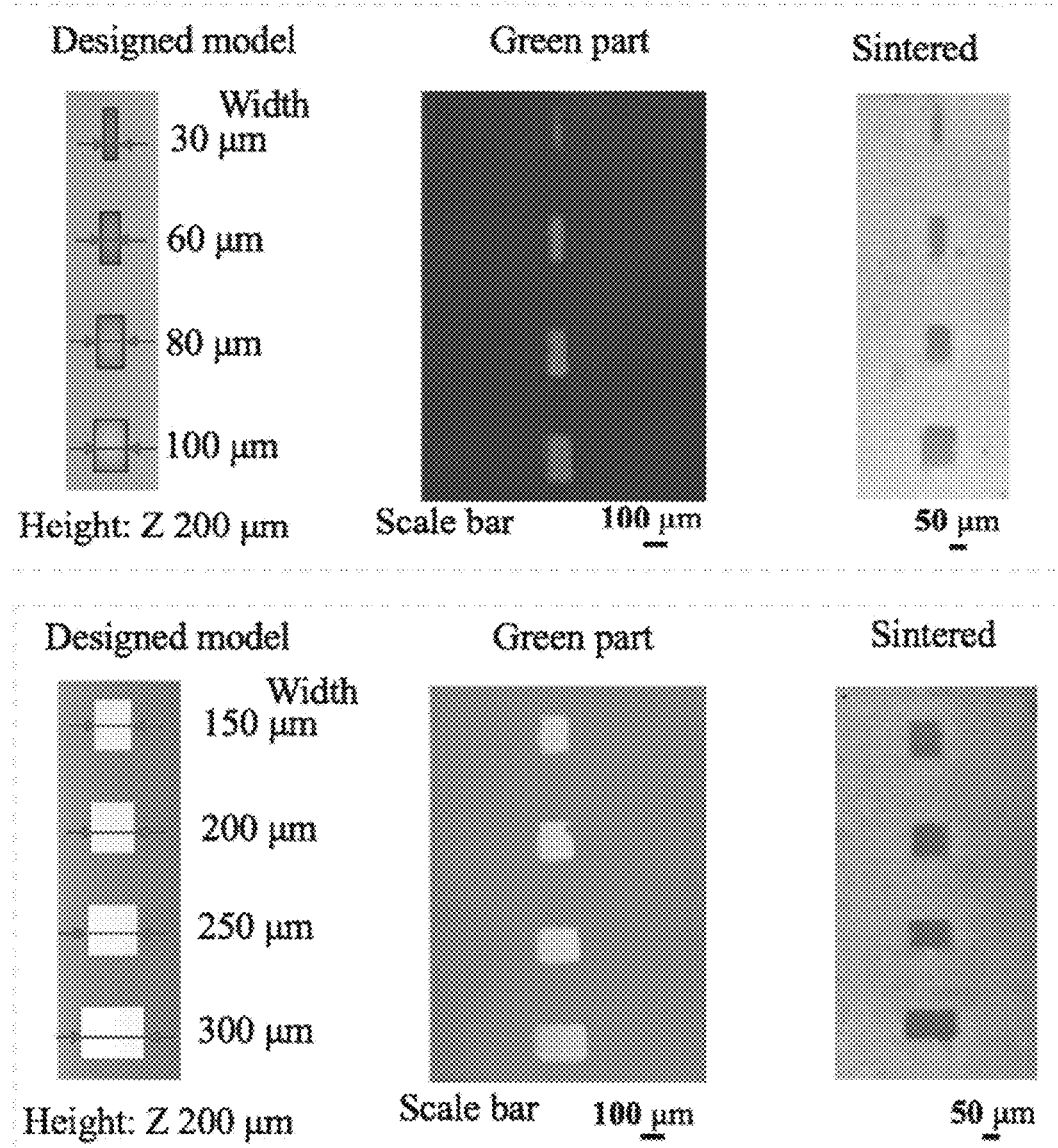
FIG. 41. Fabrication results of HA/TCP scaffold with hierarchical porous structures. (a) The printing capability of the developed slurry-based µMIP-SL in the XY direction; (b) the printing capability of the developed slurry-based µMIP-SL in the Z direction; (c) the offset operation of HA/TCP scaffold for shrinkage compensation; (d) the printed results of HA/TCP scaffolds before and after compensation; (e) and (f) the CAD model and fabrication results of HA/TCP scaffolds with micro-lattice structure and biomimetic bone structure, respectively.

Similarly, a series of squares, whose side lengths range from 30 µm to 350 µm, were 3D printed using the same HA/TCP suspension. The 3D printed results and the sintered parts are shown in FIG. 41(*b*). The compensation factor $\phi_z$ was investigated according to the shape changing rate of the micro squares in the Z direction. The dimensions of hierarchical micro-scale features were adjusted according to the compensations required in the axial and radial directions, respectively, based on the formula described as following:

$$\begin{cases} l_{dxy} = \phi_{xy} l_{oxy} \\ l_{dz} = \phi_z l_{oz} \end{cases} \qquad \text{Equation 8}$$

where $l_{dxy}$ and $l_{dz}$ are printing dimensions of microstructures in the axial and radial directions, respectively; $l_{oxy}$ and $l_{oz}$ are the ideal dimensions in the axial and radial directions, respectively; and $\phi_{xy}$ and $\phi_z$ are two constants, which are 1.39 and 1.55 for 30 wt % HA/TCP scaffold sintered at 1250° C.

The natural bone has hierarchical porous structures whose dimensions range from hundreds microns to certain nanometres (Basu et al.). With the fabrication shrinkage being compensated in the design phase, our process can accurately fabricate porous structures with the dimension of holes ranging from hundreds microns to tens of micros. In addition, the aforementioned post-processing procedures can create holes in the fabricated porous structures with the dimension range of a few microns to certain nanometres. In this study both micro-lattice structure and biomimetic bone structures were designed and fabricated using the developed slurry-based µMIP-SL process. The CAD models and 3D printing results of the HA/TCP scaffolds with micro-lattice structures and biomimetic bone structures are shown in FIGS. 41(*e*) and (*b*), respectively. The compressive strengths of the HA/TCP scaffolds designed with biomimetic bone structure and with micro-scale lattice structure are 9.5 MPa and 15.5 MPa respectively, showing satisfactory mechanical performance. More importantly, the scaffold porosity of both structural designs are greatly improved as hundreds of micro pores were added in the design and successfully fabricated by the developed 3D printing process, which is important for the cell regeneration afterwards.

Example 43. In Vitro Performance

Figure 42:
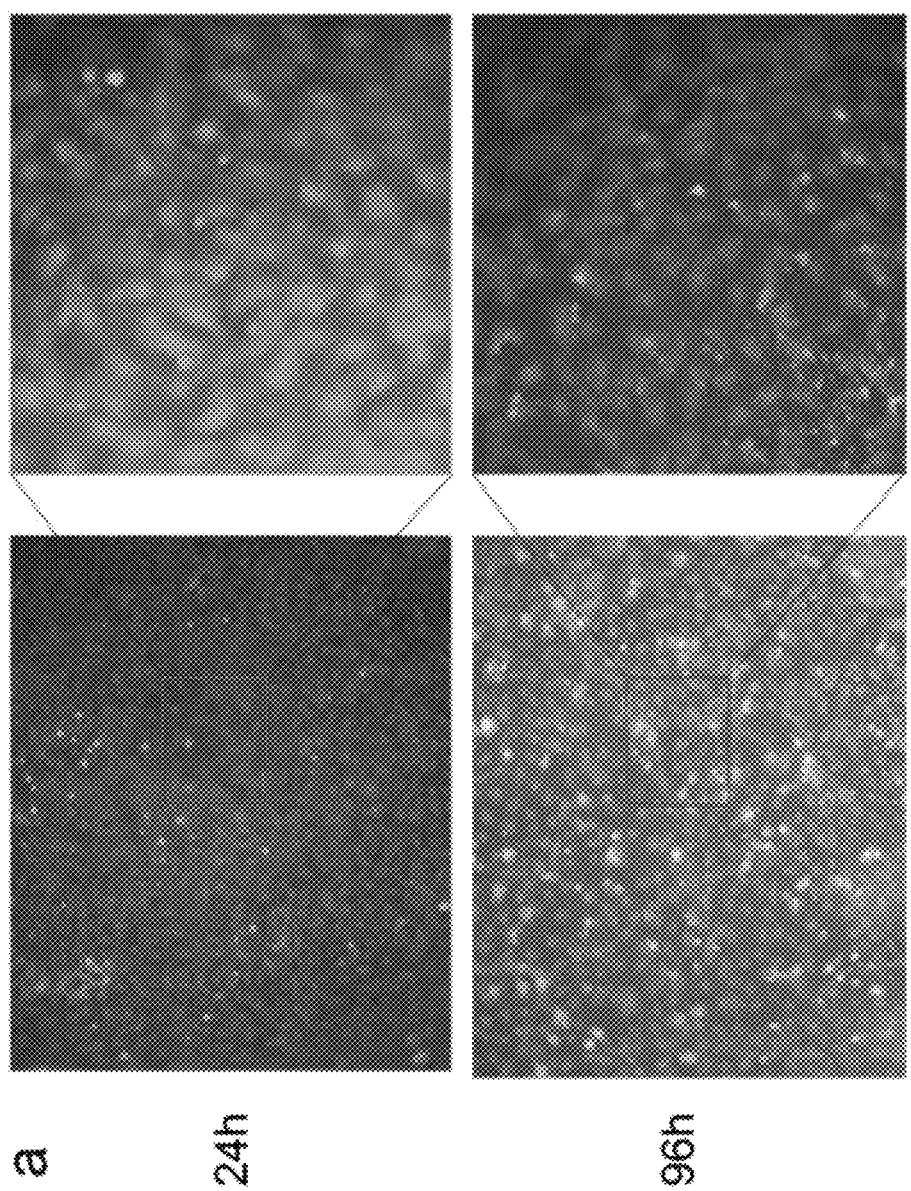
FIG. 42. The in vitro performance of HA/TCP scaffold printed at different conditions. (a) Cell viability of HA/TCP scaffold; and (b) the proliferation of cells cultured in the medium supplemented with HA/TCP scaffold printed with various concentrations.
Figure 42:
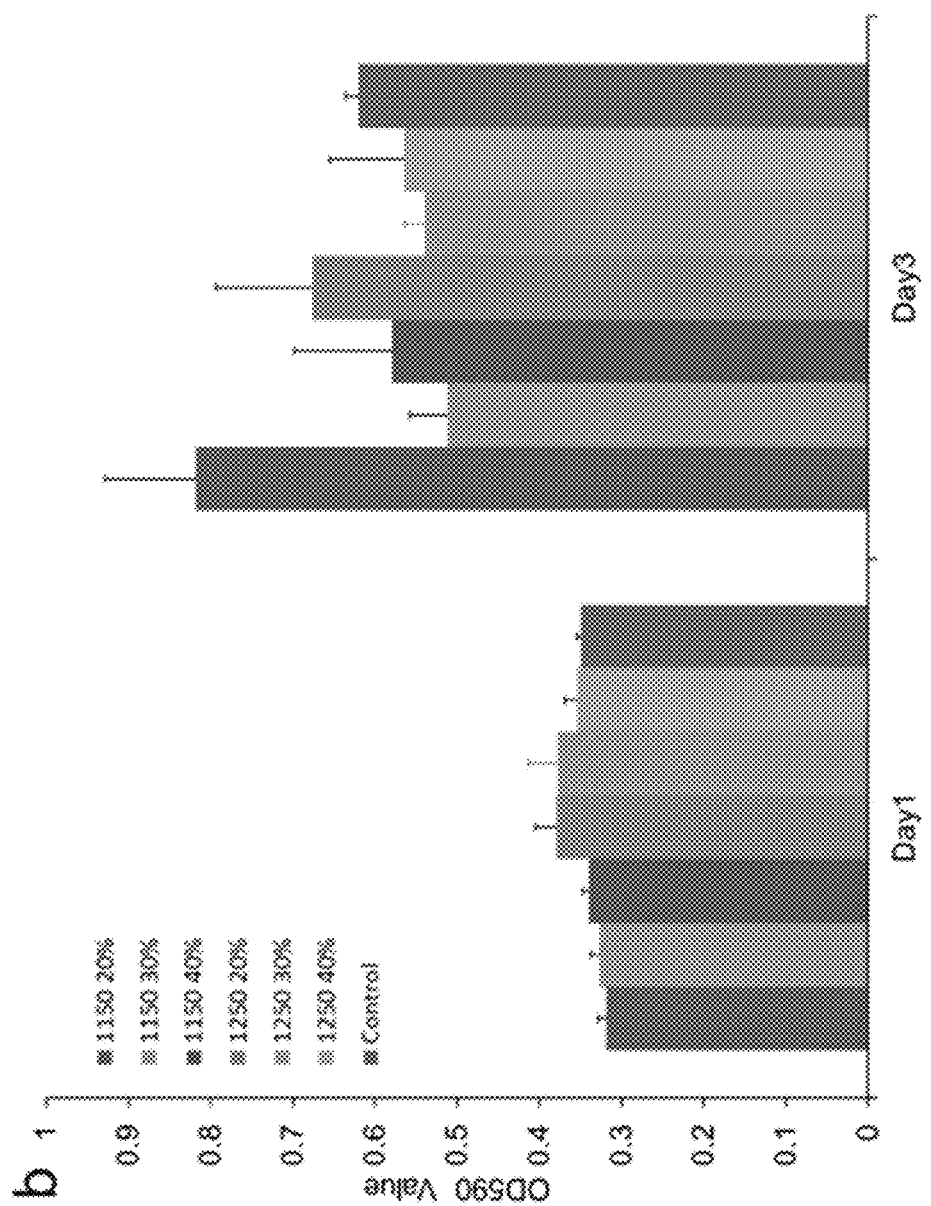

Next, we tested the biocompatibility of the HA/TCP-base scaffolds. Specifically, we first tested the cell viability when culturing the cell on the surface of the scaffolds with micro-lattice structures. After 24 hours of cell seeding, cells were able to attach to the scaffolds and showed normal spindle shaped morphology suggesting a healthy condition. We further performed live and dead staining at different time points. After 24 hours since seeding, we can barely see any dead cells indicating by red fluorescence. After 96 hours since seeding, we observed slight increase of dead cells; however, the dead cells are still less than 10% of the total cell population (refer to FIG. 42(*a*)). This may be due to an over confluency of cell number. We also investigated the effect of different concentration of HA/TCP particles in scaffolds on cell proliferation (FIG. 42(*b*)). After three days, cells cultured with HA/TCP scaffolds showed similar growth rate compared to the control group. However, we did not observe any significant difference between the scaffolds printed with different concentration of HA/TCP particles. Collectively, these data clearly suggest that HA/TCP-based scaffold is biocompatible.

Example 44. In Vivo Performance

Figure 43:
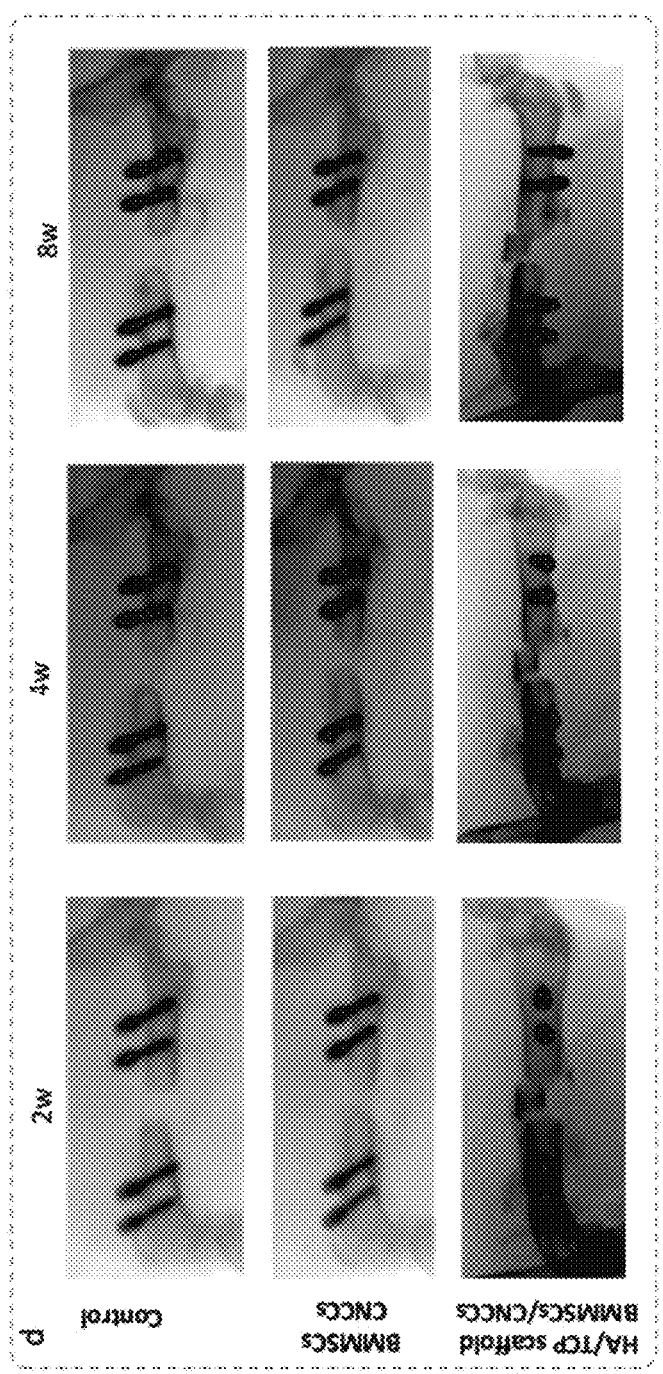
FIG. 43. The long bone critical defect healing of nude mice with the hierarchical porous HA/TCP scaffold printed by our developed method. (a) The long bone of live nude mice; (b) the 2 mm defect model of live nude mice; (c) the HA/TCP scaffold was implanted with BMMSCs at the 2 mm defect of live nude mice; and (d) the CT image of long bone healing results of 2 mm defect without CNCCs and BMMSCs, with CNCCs and BMMSCs, with CNCCs, BMMSCs and HA/TCP scaffold.

We further tested the stem cell based bone regeneration with the HA/TCP scaffolds. Mouse femur, as a bone regeneration model, has many advantages comparing to other bone tissues like calvaria, such as load bearing, manner of ossification, and less influence from the surrounding environment. However, the small size of mice increases the difficulty of mouse femur surgery. Recently, we have developed a surgical technique for femur defect using live nude mice (FIG. 43(*a*)-(*b*)). These mice can support bone regeneration up to three to four months following initial surgery and can therefore serve as a model for stem cell-mediated bone regeneration. In the control group, at 8 weeks after surgery, we did not observe bone union according to radiographic analysis, proving this defect indeed is a critical-sized defect (CSD) model. About one million bone marrow-derived mesenchymal stem cells were mixed either with or without the scaffold and loaded into the mouse's long bone CSD. As soon as two weeks after the surgery, we started to detect new bone formation in both groups with MSC treatment. Bone outgrowth in anteroposterior direction was significantly promoted compared to the control group. Meantime, we also found that the size of the scaffold is smaller based on the X-ray imaging, suggesting the degradation of the scaffolds during the bone regeneration process. After 8 weeks since the surgery, the bone regeneration was significantly improved in the treatment groups, and the mice in cells with scaffold group have smaller gap in the defect site compared to both control and cells alone groups. However, we still failed to observe the union of the cortical bone matrix (refer to FIG. 43(*d*)). Interestingly, we noticed that the HA/TCP scaffold was slightly pushed away from the injury site, suggesting that a faster degradation rate of the scaffold may further improve the healing outcome of the defect. Taking together, these data suggest that HA/TCP scaffold has an osteoinductive effect on bone regeneration in the mouse CSD model. In the future study, we will continue optimizing the constituents of HA/TCP based scaffold to manipulate the degradation of the scaffold to better facilitate the regeneration of long bone defect.

Applicable material and functional structure of scaffold are two essential factors to consider when dealing with the bone healing and cell regeneration problems. Biocompatible ceramic HA/TCP, with superior performance in promoting adhesions and proliferation of bone-forming cells, are widely used in bone tissue regeneration. HA/TCP itself, however, is considered to be difficult to form complex geometric shapes using current manufacturing methods. In this disclosure, we presented a slurry-based µMIP-SL process, which made it possible to use nano-scale HA/TCP particles to build HA/TCP scaffold with complex hierarchical porous structures. Firstly, the curing performance of HA/TCP suspension has been studied, and the process of our 3D printing method, featured with slurry feeding module, was introduced and demonstrated. The post-processing setting and suspension constituents of HA/TCP scaffold were systematically optimized in regard to structural porosity and mechanical properties. To improve the fabrication accuracy of hierarchical porous structures, a shape compensation scheme was developed based on the shrinkage behavior of the HA/TCP fabrication process. Meanwhile, to achieve high mechanical strength with sufficient porosity, HA/TCP scaffolds with biomimetic bone structure and micro lattice structure were designed and fabricated. Both the cell proliferation and vivo test of HA/TCP scaffold were conducted, and experimental results had shown that the HA/TCP scaffold with the BMMSCs can promote the bone healing in the long bone critical defect of mouse animal model. In future, nano-scale HA/TCP particles with other biodegradable polymer will be fabricated using our developed 3D printing method to speed up the degradation of HA/TCP scaffolds, and other bio-molecules like growth factor will be integrated with the 3D printed HA/TCP scaffold to further accelerate the bone healing.

Example 45. An Exemplary Preparation of a Bone Regeneration Product

Figure 18:
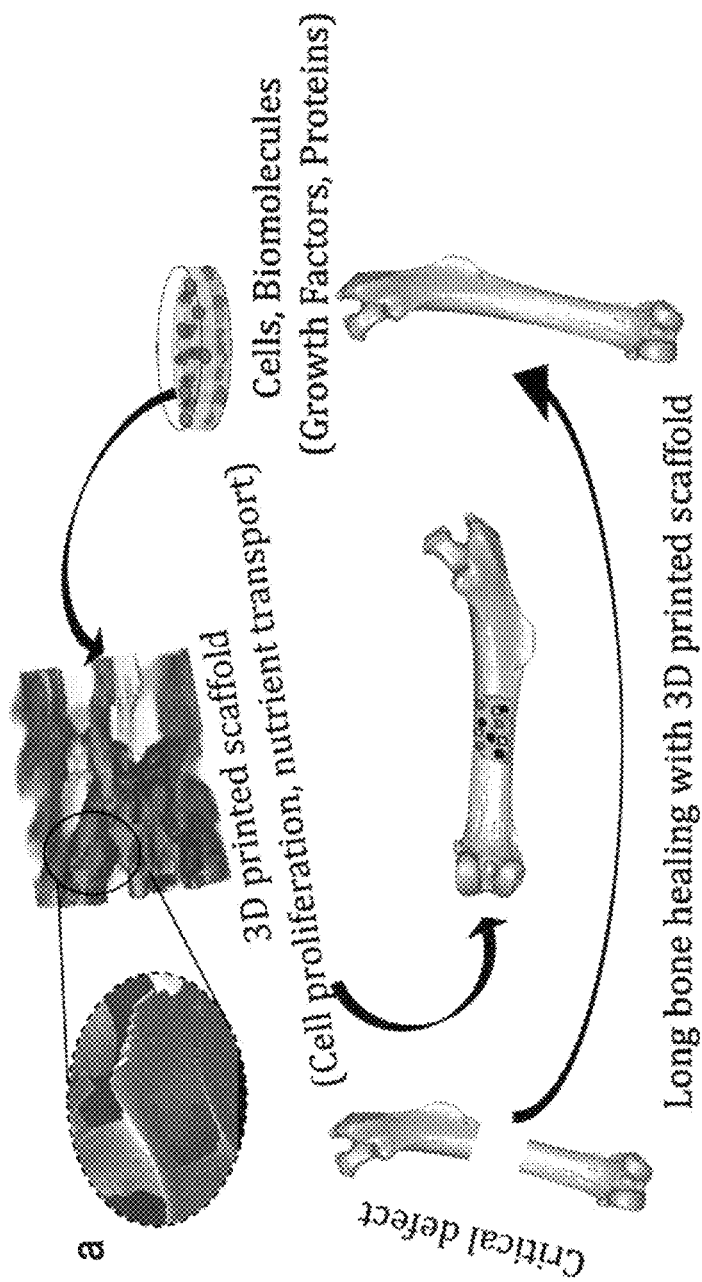
FIG. 18. The schematic diagram of bone tissue regeneration with 3D printed scaffold. (a) Critical defect in long bone healing using 3D printed scaffold; (b) Diagram of cranial defect regrowth using 3D printed scaffold.
Figure 18:
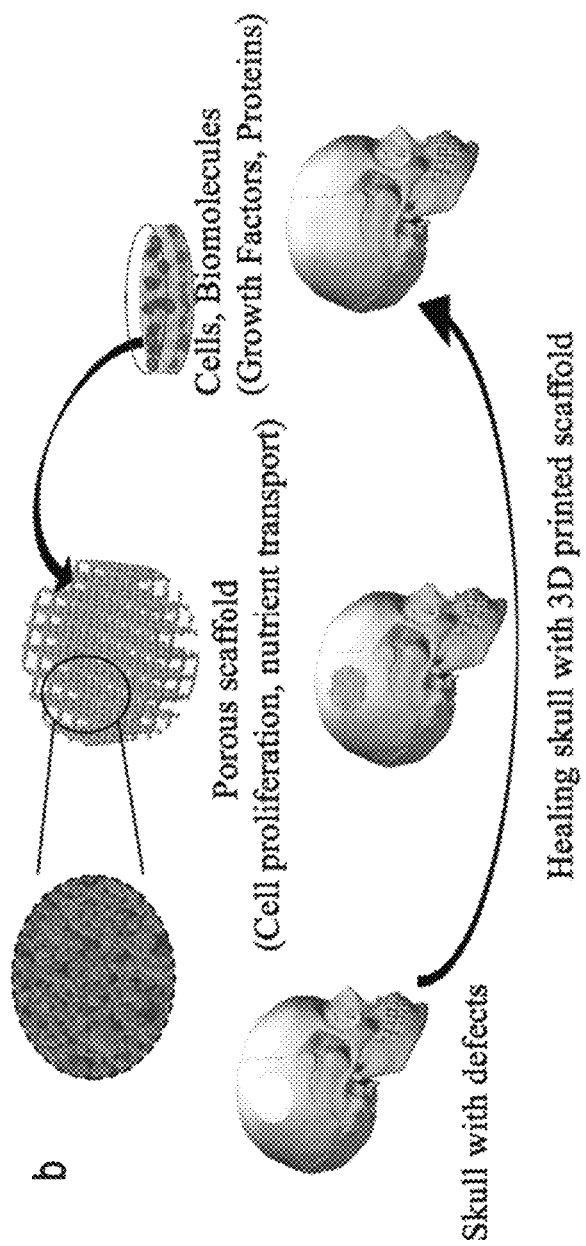

At first stage, we developed a process that can fabricate the scaffold with growth factors using biodegradable polymer and bone materials. As shown in FIG. 18, for long bone regeneration, the 3D porous scaffolds may be designed and built on which cells may easily be attached.

First, the damaged bone is scanned to obtain its detailed features across the damaged and the undamaged zones of the bone. A scaffold with a suitable porous structure may then be designed with a proper mechanical performance to host live cells. Micro-scale mask image projection based SLA process may then be applied to fabricate a porous scaffold comprising a polymer mixed with a growth factor and bio-ceramic compound (e.g. HA/TCP).

Cells may then be loaded and cultivated on surfaces of the 3D printed biodegradable scaffold for damaged zone regeneration. Similarly, 3D scaffolds may then designed and fabricated for cranial defects (an example is shown in FIG. 18). The model of cranial defect may be generated through scanning so that all detailed features of defects can be obtained. A customized porous scaffold is designed in accordance to the detail of cranial defect.

Finally, a bio-ceramic (HA/TCP) suspension is prepared to construct the porous 3D scaffold, and a HA/TCP scaffold designed for cranial critical defect may be fabricated by using mask image projection based stereolithography (MIP-SL) with circular movements.

We have developed a calvarial bone CSD model in swine and have successfully used autologous MSCs with a 3D-printed scaffold to regenerate calvarial bone in a CSD, forgoing the use of metal or plastic implants and bone grafts. We used DPNCCs from the craniofacial region, which are capable of producing dense cortical bone. To promote MSCs to differentiate into functional osteoblasts, we combined them with 3D printed osteoinductive scaffold fabricated using hydroxyapatite and tricalcium phosphate (HA/TCP), to which mesenchymal stem cells can adhere. We have created and tested a large animal model that has a head size similar to that of humans.

For bone tissues, most bone grafts are made by metal, high stress polymer or ceramic, which provide certain mechanical strength. Due to the limitation of geometrical shape, traditional bone grafts cannot totally serve the functionalities such as bone formation and acceleration of new growth fabrication methods. To overcome the challenges, three-dimensional scaffolds cultured with stem cells bring a promising solution of tissue regeneration, and both materials composition and geometric structure of scaffold play critical roles in the new bone regrowth.

Example 46. An Exemplary Bio-Degradable Scaffold

Regeneration of the bone tissue may be achieved by culturing patients' cells with bio-degradable scaffolds. During the biodegradation of the scaffold, the tissue may grow back to heal defects with bioactive cells.

In tissue engineering, the scaffold with complex three-dimensional (3D) structures provides support to the cells, and regulates cell growth and nutriention transportation. Many different techniques have been used to fabricate scaffolds, of which some include woven and nonwoven fiber-based fabrics, solvent casting, particulate leaching, phase separation, melt molding, high-pressure processing, forging, injection molding, and hot and cold pressing.

The 3D structures of the scaffold fabricated by these methods are regularly shaped. Due to the limitations of these structures, traditional bone grafts may not totally serve the functionalities such as bone formation and acceleration of new growth fabrication methods.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Example 47. Bone Regeneration Product Further Comprising Smurf1 Inhibitors

In this example, experiments were carried out in a manner described in connection with Examples disclosed above. HA/TCP powder form were used as a scaffold. CNCC: BMMSC ratio was 9:1. Phenamil amount was 300 μM and BMP2 amount was 2 μg.

Figure 44:
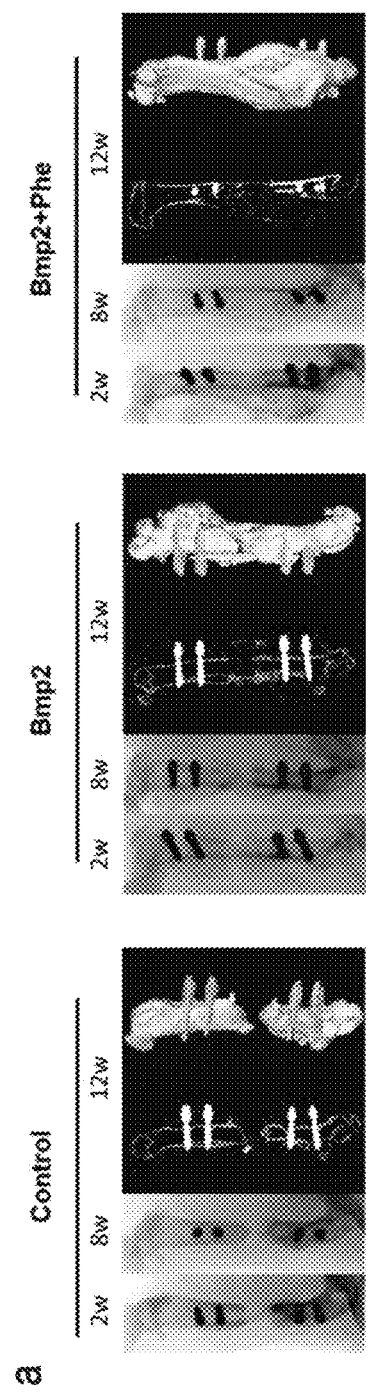
FIG. 44. Cortical bone union was achieved after a treatment of a mouse CSD by using a bone regeneration product of this invention, wherein the bone regeneration product comprises BMP2 and phenamil. (A) X-ray images were taken at 2, 4 and 8 weeks after femoral CSDs. (B) MicroCT image was taken after sample harvest at 12 weeks after surgery.
Figure 44:
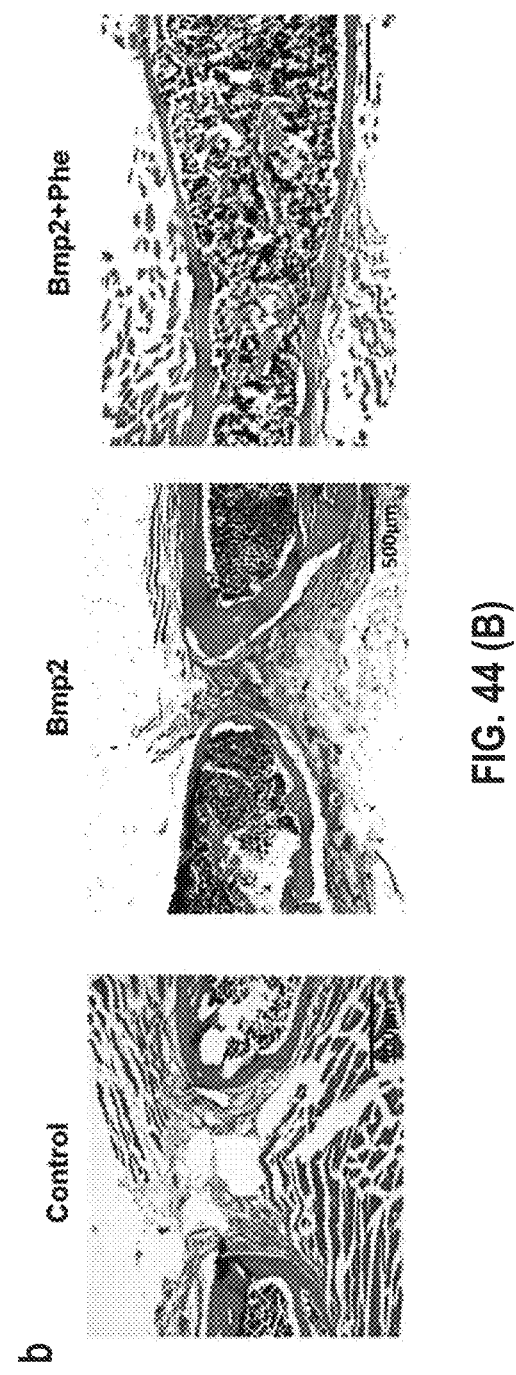

We detected callus formation in the defect site after four weeks, and bone outgrowth on the AP direction is significantly improved. The cortical bone union was observed (FIG. 44A), eight weeks after the surgery. Through histology, we found continuous cortical bone with only some trabecular structure remaining in the bone marrow space, suggesting not only a good bone union was achieved but also the remodeling process is progressing smoothly (FIG. 44B).

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Any combinations of above bone regeneration products, their features, their preparation methods, and/or their use in the treatment of bones with defects are within the scope of this disclosure.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A bone regeneration product, comprising a scaffold, wherein:
    the scaffold comprises at least one first chamber and at least one second chamber;
    the at least one first chamber holds a stem cell mixture comprising dense bone regenerating stem cells (DBR-SCs);
    the at least one second chamber holds a stem cell mixture comprising spongy bone regenerating stem cells (SBR-SCs);
    the DBR-SCs comprise cranial neural crest derived mesenchymal stem cells (CNCCs), dental pulp derived stem cells (DPSCs), or a mixture thereof; and
    the SBR-SCs comprise bone marrow derived mesenchymal stem cells (BMMSCs).

2. The bone regeneration product of claim 1, wherein a concentration of the DBR-SCs in the stem cell mixture, which is held by the at least one first chamber, is in a range of 60% to 100%; and wherein a concentration of the SBR-SCs of the stem cell mixture, which is held by the at least one second chamber, is in a range of 60% to 100%.

3. The bone regeneration product of claim 1, wherein concentration of the DBR-SCs in the stem cell mixture, which is held by the at least one first chamber, is in a range of 80% to 100%; and wherein a concentration of the SBR-SCs in the stem cell mixture, which is held by the at least one second chamber, is in a range of 80% to 100%.

4. The bone regeneration product of claim 1, wherein the scaffold comprises a growth factor; and wherein the growth factor comprises a bone morphogenic protein (BMP), vascular endothelial growth factor (VEGF), platelet derived growth factor (PDGF), phenamil, or a combination thereof.

5. The bone regeneration product of claim 3, wherein the scaffold comprises a growth factor; and wherein the growth factor comprises a BMP, VEGF, PDGF, phenamil, or a combination thereof.

6. The bone regeneration product of claim 1, wherein the at least one first chamber partially or substantially surrounds the at least one second chamber.

7. The bone regeneration product of claim 1, wherein:
    the at least one first chamber and the at least one second chamber each comprises an opening;
    the opening has a characteristic length; and
    the characteristic length of the at least one first chamber's opening is smaller than a particular size such that each stem cell can be kept confined in the at least one first chamber, and/or the characteristic length of the at least one second chamber's opening is smaller than a particular size such that each stem cell can be kept confined in the at least one second chamber.

8. The bone regeneration product of claim 1, wherein a compressive strength of the scaffold is in a range of 0.1 MPa to 10 MPa; and a porosity of the scaffold is in a range of 1% to 40%.

9. The bone regeneration product of claim 1, wherein a compressive strength of the scaffold is in a range of 5 MPa to 10 MPa; and a porosity of the scaffold is in a range of 3% to 10%.

10. The bone regeneration product of claim 1, wherein the scaffold comprises an article; wherein the article is produced from a mixture comprising hydroxyapatite (HA) and tricalcium phosphate (TCP); and wherein the mixture's HA concentration is in a range of 10 weight % to 20 weight %, and the mixture's TCP concentration is in a range of 10 weight % to 20 weight %.

11. The bone regeneration product of claim 3, wherein:
    the scaffold comprises a growth factor; wherein the growth factor comprises a BMP, VEGF, PDGF, phenamil, or a combination thereof; and
    a compressive strength of the scaffold is in a range of 0.1 MPa to 10 MPa; and porosity of the scaffold is in a range of 1% to 40%.

12. The bone regeneration product of claim 11, wherein the scaffold's compressive strength is in the range of 5 MPa to 10 MPa; and the scaffold's porosity is in the range of 3% to 10%.

13. The bone regeneration product of claim 11, wherein the at least one first chamber partially or substantially surrounds the at least one second chamber.

14. The bone regeneration product of claim 11, wherein:
    the at least one first chamber and the at least one second chamber each comprises an opening;
    the opening has a characteristic length; and
    the characteristic length of the at least one first chamber's opening is smaller than a particular size such that each stem cell can be kept confined in the at least one first chamber, and/or the characteristic length of the at least one second chamber's opening is smaller than a particular size such that each stem cell can be kept confined in the at least one second chamber.

15. A bone regeneration product, comprising a scaffold; wherein:
- the scaffold comprises an article produced from a formulation comprising:
  - (i) a photo-curable polymer comprising polycaprolactone (PCL), polycaprolactone dimethacrylate (PCL-DA), gelatin methacryloyl (GelMA), or a mixture thereof; and/or
  - (ii) a photo-curable polymer prepared by polymerizing a photo-curable monomer comprising a monomer of polycaprolactone (PCL), a monomer of polycaprolactone dimethacrylate (PCL-DA), or a mixture thereof; and
- wherein the scaffold has a compressive strength in a range of 0.1 MPa to 10 MPa; and
- wherein the scaffold has a porosity in a range of 1% to 40%.

16. The bone regeneration product of claim 15, wherein the scaffold comprises a growth factor; wherein the growth factor comprises a BMP, VEGF, PDGF, phenamil, or a combination thereof.

17. The bone regeneration product of claim 15, the formulation further comprising calcium phosphate, HA, TCP, or a mixture thereof.

18. The bone regeneration product of claim 17, the scaffold further comprising a growth factor; wherein the growth factor comprises a BMP, VEGF, PDGF, phenamil, or a combination thereof.

19. The bone regeneration product of claim 17, wherein the scaffold's compressive strength is in the range of 5 MPa to 10 MPa; and the scaffold's porosity is in the range of 3% to 10%.

20. The bone regeneration product of claim 15, wherein the formulation further comprises HA and TCP; and wherein the formulation's HA concentration is in a range of 10 weight % to 20 weight %, and the formulation's TCP concentration is in a range of 10 weight % to 20 weight %.

21. The bone regeneration product of claim 16, wherein the formulation further comprises HA and TCP; and wherein the formulation's HA concentration is in a range of 10 weight % to 20 weight %, and the formulation's TCP concentration is in a range of 10 weight % to 20 weight %.

* * * * *